(12) United States Patent
Laird et al.

(10) Patent No.: US 7,491,829 B2
(45) Date of Patent: Feb. 17, 2009

(54) RAF INHIBITOR COMPOUNDS AND METHODS

(75) Inventors: Ellen Laird, Longmont, CO (US); Joseph P. Lyssikatos, Superior, CO (US); Mike Welch, Westminster, CO (US); Jonas Grina, Superior, CO (US); Josh Hansen, Longmont, CO (US); Brad Newhouse, Broomfield, CO (US); Alan Olivero, Half Moon Bay, CA (US); George Topalov, Superior, CO (US)

(73) Assignees: Array Biopharma Inc., Boulder, CO (US); Genentech, Inc., South San Francisco, CA (US)

( * ) Notice: Subject to any disclaimer, the term of this patent is extended or adjusted under 35 U.S.C. 154(b) by 0 days.

(21) Appl. No.: 11/345,828

(22) Filed: Feb. 2, 2006

(65) Prior Publication Data
US 2006/0189627 A1   Aug. 24, 2006

Related U.S. Application Data

(60) Provisional application No. 60/650,050, filed on Feb. 4, 2005.

(51) Int. Cl.
C07D 231/14 (2006.01)
A61K 31/4155 (2006.01)
A61K 31/416 (2006.01)
(52) U.S. Cl. ................................. 548/364.1; 514/406
(58) Field of Classification Search ............... 548/364.1; 514/406
See application file for complete search history.

(56) References Cited

U.S. PATENT DOCUMENTS

| | | | |
|---|---|---|---|
| 4,000,281 A | 12/1976 | Beiler et al. | |
| 5,356,897 A | 10/1994 | Oku et al. | |
| 5,486,534 A | 1/1996 | Lee et al. | |
| 5,707,997 A | 1/1998 | Shoji et al. | |
| 5,843,951 A | 12/1998 | Inoue et al. | |
| 5,932,576 A | 8/1999 | Anantanarayan et al. | |
| 6,028,072 A | 2/2000 | Lee et al. | |
| 6,423,713 B1 | 7/2002 | Anantanarayan et al. | |
| 6,514,977 B1 | 2/2003 | Anantanarayan et al. | |
| 6,525,059 B1 | 2/2003 | Anantanarayan et al. | |
| 6,528,509 B1 | 3/2003 | Hale et al. | |
| 6,750,239 B2 | 6/2004 | Hale et al. | |
| 6,784,195 B2 | 8/2004 | Hale et al. | |
| 6,849,267 B2 | 2/2005 | Bemis et al. | |
| 6,949,580 B2 | 9/2005 | Hale et al. | |
| 2003/0078277 A1 | 4/2003 | Hibi et al. | |
| 2003/0139452 A1 | 7/2003 | Tang et al. | |
| 2003/0153588 A1 | 8/2003 | Steadman et al. | |
| 2004/0038964 A1 | 2/2004 | Dean et al. | |
| 2004/0048868 A1 | 3/2004 | Edwards et al. | |
| 2004/0058918 A1 | 3/2004 | Dominguez et al | |
| 2004/0072833 A1 | 4/2004 | Nakai et al. | |
| 2004/0116474 A1 | 6/2004 | Munchhof et al. | |
| 2004/0127496 A1 | 7/2004 | Dean et al. | |
| 2004/0147525 A1 | 7/2004 | Kimura et al. | |
| 2004/0157838 A1 | 8/2004 | Griffith | |
| 2004/0209883 A1 | 10/2004 | Bamford et al. | |
| 2004/0235843 A1 | 11/2004 | Bamford | |
| 2005/0026963 A1* | 2/2005 | Cosford et al. ............... 514/341 |
| 2005/0222230 A1 | 10/2005 | Drysdale | |
| 2005/0245520 A1 | 11/2005 | Dodic et al. | |
| 2006/0058329 A1 | 3/2006 | Gellibert | |

FOREIGN PATENT DOCUMENTS

EP   1382603 A1   1/2004

(Continued)

OTHER PUBLICATIONS

Vippagunta, et al. Advanced Drug Delivery Reviews 48 (2001) 3-26.*

(Continued)

*Primary Examiner*—Kamal A Saeed
*Assistant Examiner*—Shawquia Young
(74) *Attorney, Agent, or Firm*—Viksnins Harris & Padys PLLP

(57) ABSTRACT

Pyrazolyl compounds of Formulas Ia and Ib are useful for inhibiting Raf kinase and for treating disorders mediated thereby. Methods of using pyrazolyl compounds for in vitro, in situ, and in vivo diagnosis, prevention or treatment of such disorders in mammalian cells, or associated pathological conditions are disclosed.

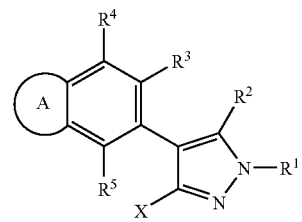

Ia

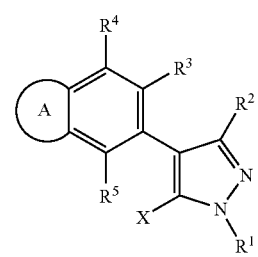

Ib

49 Claims, No Drawings

FOREIGN PATENT DOCUMENTS

| | | |
|---|---|---|
| GB | 1245283 | 9/1971 |
| JP | 05017470 | 1/1993 |
| JP | 05125079 | 5/1993 |
| JP | 10101671 | 4/1998 |
| JP | 10101672 | 4/1998 |
| JP | 2000153671 | 6/2000 |
| WO | WO 00/64422 | 11/2000 |
| WO | WO 02/072576 A1 | 9/2002 |
| WO | WO 02/094808 A1 | 11/2002 |
| WO | WO 02/094833 | 11/2002 |
| WO | WO 03/051358 A1 | 6/2003 |
| WO | WO 03/055860 A1 | 7/2003 |
| WO | WO 03/095455 A2 | 11/2003 |
| WO | WO 2004/014900 | 2/2004 |
| WO | WO 2004/022055 A1 | 3/2004 |
| WO | WO 2004/026302 A1 | 4/2004 |
| WO | WO 2004/026871 | 4/2004 |
| WO | WO 2004/050659 | 6/2004 |
| WO | WO 2004/072033 A2 | 8/2004 |

OTHER PUBLICATIONS

Almansa et al., "Synthesis and SAR of a new series of COX-2-selective inhibitors: pyrazolo [1,5-a]pyrimidines" *J Med Chem.* 44(3):350-361 (Feb. 1, 2001).

Bellec et al., "Deaminative electrochemical reduction of pyrazolo [1,5-a]pyrimidine-7amines" *Can.J. Chem.* 59(19):2826-2832 (1981).

Comrie, A. M., "3,4,5-Triarylpyrazoles" *Journal of the Chemical Society, Perkin Transactions 1* (Database *Caplus [Online]*; STN accession No. 1972:153662; Database accession No. 76:153662; RN: 36141-11-4; RN 36141-12-5), Letchworth:Gbchemical Society vol. 9-10:1193 (1972).

de Laszlo et al., "Pyrroles and other heterocycles as inhibitors of p38 kinase" *Bioorg Med Chem Lett.* 8(19):2689-2694 (Oct. 6, 1998).

Dombroski et al., "Benzimidazolone p38 inhibitors" *Bioorg Med Chem Lett.* 14:919-923 (Feb. 23, 2004).

Fray et al., "Novel antagonists of platelet-activating factor. 2. Synthesis and structure-activity relationships of potent and long-acting heterofused[1,5]benzodiazepine and [1,4]diazepine derivatives of 2-methyl-1-phenylimidazo[4,5-c]pyridine" *J Med Chem.* 38(18):3524-3535 (Sep. 1, 1995).

Khilya et al., "Synthetic And Modified Isoflavonoids XV. Interaction of Synthetic Analogs of Isoflavones With Hydrazine Hydrate And Its Derivatives" *Chemistry of Natural Compounds* 30(5):580-583 (1994).

Olivera et al., "A combination of tandem amine-exchange/ heterocyclization and biaryl coupling reactions for the straightforward preparation of phenanthro[9,10-d]pyrazoles" *J Org Chem.* 65(21):7010-7019 (Oct. 20, 2000).

Penning et al., "3,4-Diarylpyrazoles: Potent and selective inhibitors of Cyclooxygenase-2" *Bioorganic & medicinal chemistry letters* 7(16):2121-2124.

Sawyer et al., "Synthesis and activity of new aryl- and heteroaryl-substituted pyrazole inhibitors of the transforming growth factor-beta type I receptor kinase domain" *J Med Chem.* 46(19):3953-3956 (Sep. 11, 2003).

Complete International Search Report for International Patent Application No. PCT/US2006/003654, mailed Aug. 24, 2006.

Hansen, Joshua et al., "Potent and Selective Pyrazole-Based Inhibitors of B-Raf Kinase," *Bioorganic & Medicinal Chemistry Letter*, pp. 4692-4695, 2008.

\* cited by examiner

RAF INHIBITOR COMPOUNDS AND METHODS

CROSS-REFERENCE TO RELATED APPLICATIONS

This non-provisional application filed under 37 CFR §1.53 (b), claims the benefit under 35 USC §119(e) of U.S. Provisional Application Ser. No. 60/650,050 filed on Feb. 4, 2005, which is incorporated by reference in entirety.

FIELD OF THE INVENTION

In one aspect, the invention relates to novel pyrazolyl compounds which are inhibitors of Raf kinase, as well as compositions containing these compounds and methods of use. The pyrazolyl compounds are useful for inhibiting Raf kinase and for treating disorders mediated thereby. The invention also relates to methods of using pyrazolyl compounds for in vitro, in situ, and in vivo diagnosis or treatment of mammalian cells, or associated pathological conditions.

BACKGROUND OF THE INVENTION

The Raf/MEK/ERK (extracellular signal-regulated kinase) kinase cascade is pivotal in transmitting signals from membrane receptors to transcription factors that control gene expression culminating in the regulation of cell cycle progression (Robinson, M J and Cobb, M H (1997) Curr. Opin. Cell Biol. 9:180-186). This cascade can prevent cell death through ERK2 and p90(Rsk) activation and phosphorylation of apoptotic and cell cycle regulatory proteins (Shelton J G et al (2003) Oncogene. 22(16):2478-92). The PI3K/Akt kinase cascade also controls apoptosis and can phosphorylate many apoptotic and cell cycle regulatory proteins. These pathways are interwoven as Akt can phosphorylate Raf (Rapidly growing Fibrosarcoma) and result in its inactivation, and Raf can be required for the anti-apoptotic effects of Akt. Raf is a key serine-threonine protein kinase which participates in the transmission of growth, anti-apoptotic and differentiation messages. These signals can be initiated after receptor ligation and are transmitted to members of the MAP kinase cascade that subsequently activate transcription factors controlling gene expression. Raf is a multigene family which expresses oncoprotein kinases: Raf-1, A-Raf and B-Raf (McCubrey J A. et al (1998) Leukemia. 12(12):1903-1929; Ikawa et al (1988) Mol. and Cell. Biol. 8(6):2651-2654; Sithanandam et al (1990) Oncogene 5:1775-1780; Konishi et al (1995) Biochem. and Biophys. Res. Comm. 216(2):526-534). All three Raf kinases are functionally present in certain human hematopoietic cells, and their aberrant expression can result in abrogation of cytokine dependency. Their regulatory mechanisms differ because C-Raf and A-Raf require additional serine and tyrosine phosphorylation within the N region of the kinase domain for full activity (Mason et al (1999) EMBO J. 18:2137-2148), and B-Raf has a much higher basal kinase activity than either A-Raf or C-Raf. The three Raf oncoproteins play critical roles in the transmission of mitogenic and anti-apoptotic signals. B-Raf has recently been shown to be frequently mutated in various human cancers (Wan et al (2004) Cell 116:855-867). Development of specific Raf inhibitors may prove efficacious in cancer therapy. The cytoplasmic serine/threonine kinase B-Raf and receptor tyrosine kinases of the platelet-derived growth factor receptor (PDGFR) family are frequently activated in cancer by mutations of an equivalent amino acid. Structural studies have provided important insights into why these very different kinases share similar oncogenic hot spots and why the PDGFR juxtamembrane region is also a frequent oncogenic target (Dibb N J (2004) Nature Reviews. Cancer. 4(9):718-27).

Transformation of normal melanocytes into melanoma cells is accomplished by the activation of growth stimulatory pathways, typically leading to cellular proliferation, and the inactivation of apoptotic and tumor suppressor pathways. Small molecule inhibitors of proteins in the growth stimulatory pathways are under active investigation, and their application to melanoma patients would represent a new treatment strategy to inhibit cell proliferation or induce cell death (Polsky D. (2003) Oncogene, 22(20):3087-91; Konopleva, M et al. (2003) Blood, 102(11):625a).

B-Raf encodes a Ras-regulated kinase that mediates cell growth and malignant transformation kinase pathway activation that controls cell growth and survival. Activation of the Ras/Raf/MEK pathway results in a cascade of events from the cell surface to the nucleus ultimately affecting cellular proliferation, apoptosis, differentiation and transformation. Raf is a downstream effector enzyme of Ras. When activated, Raf goes on to activate MEK1 and MEK2 kinases which in turn phosphorylate and activate ERK1 and ERK2 which translocate to the nucleus where they stimulate pathways required for translation initiation and transcription activation leading to proliferation (Sorbera et al. (2002) Drugs of the Future 27(12):1141-1147). Activating B-Raf mutations have been identified in 66% of melanomas and a smaller percentage of many other human cancers. B-Raf mutations also account for the MAP kinase pathway activation common in non-small cell lung carcinomas (NSCLCs), including V600E and other mutations identified as novel, altering residues important in AKT-mediated B-Raf phosphorylation which suggest that disruption of AKT-induced B-Raf inhibition can play a role in malignant transformation. Although >90% of B-Raf mutations in melanoma involve codon 600 (57 of 60), 8 of 9 B-Raf mutations reported to date in NSCLC are non-V600 (89%; P<10(-7)), strongly suggesting that B-Raf mutations in NSCLC are qualitatively different from those in melanoma; thus, there may be therapeutic differences between lung cancer and melanoma in response to Raf inhibitors (Karasarides et al. (2004) Oncogene 23(37):6292-6298; Bollag et al. (2003) Current Opinion in Invest. Drugs 4(12):1436-1441). Although uncommon, B-Raf mutations in human lung cancers may identify a subset of tumors sensitive to targeted therapy (Brose M S et al. (2002) Cancer Research 62(23): 6997-7000; US 2005/267060).

Raf protein kinases are key components of signal transduction pathways by which specific extracellular stimuli elicit precise cellular responses in mammalian cells. Activated cell surface receptors activate ras/rap proteins at the inner aspect of the plasma membrane which in turn recruit and activate Raf proteins. Activated Raf proteins phosphorylate and activate the intracellular protein kinases MEK1 and MEK2. In turn, activated MEKs catalyze phosphorylation and activation of p42/p44 mitogen-activated protein kinase (MAPK). A variety of cytoplasmic and nuclear substrates of activated MAPK are known which directly or indirectly contribute to the cellular response to environmental change. In fact, B-Raf mutation has been shown to predict sensitivity to pharmacological MEK inhibition by small molecule inhibitors by limiting tumor growth in B-Raf mutant xenografts (Solit et al (2005) Nature Letters to Editor 6 Nov. 2005, doi:10.1038). Three distinct genes have been identified in mammals that encode Raf proteins; A-Raf, B-Raf and C-Raf (also known as Raf-1) and isoformic variants that result from differential splicing of mRNA are known. In particular, it has been suggested that B-Raf is the major Raf isoform activated by the neurotrophin, nerve growth factor (NGF), for NGF induced extracellular signaling by kinase activation (York et al. (2000) Mol. and Cell. Biol. 20(21):8069-8083).

Cancer chemotherapy drugs typically have a narrow therapeutic index, and often the responses produced are only just palliative as well as unpredictable. In contrast, targeted therapy that has been introduced in recent years is directed against cancer-specific molecules and signaling pathways and thus has more limited nonspecific toxicities. Tyrosine kinases are an esp. important target because they play an important role in the modulation of growth factor signaling (Arora et al. (2005) Jour. of Pharm. and Exp. Ther. 315(3): 971-979). Small molecule inhibitors of tyrosine kinase compete with the ATP binding site of the catalytic domain of several oncogenic tyrosine kinases (Fabian et al. (2005) Nature Biotechnology 23(3):329-336). Several tyrosine kinase inhibitors (TKIs) have been found to have effective antitumor activity and have been approved or are in clinical trials, including imatinib mesylate (STI571; Gleevec), gefitinib (Iressa), erlotinib (OSI-1774; Tarceva), lapatinib (GW-572016), canertinib (CI-1033), semaxinib (SU5416), vatalanib (PTK787/ZK222584), sorafenib (BAY 43-9006), sutent (SU11248), and leflunomide (SU101). TKIs are thus an important new class of targeted therapy that interfere with specific cell signaling pathways and thus allow target-specific therapy for selected malignancies. The Raf/MEK/ERK pathway is the focus of intense drug discovery efforts (Thompson et al. (2005) Current Opinion in Pharmacology 5(4):350-356; Sridhar et al (2005) Molecular Cancer Therapeutics 4(4):677-685).

Inhibitors of Raf kinases have been suggested for use in disruption of tumor cell growth and hence in the treatment of cancers, e.g. histiocytic lymphoma, lung adenocarcinoma, small cell lung cancer and pancreatic and breast carcinoma; and also in the treatment and/or prophylaxis of disorders associated with neuronal degeneration resulting from ischemic events, including cerebral ischemia after cardiac arrest, stroke and multi-infarct dementia and also after cerebral ischemic events such as those resulting from head injury, surgery and/or during childbirth (Strumberg et al. (2005) Onkologie 28(2):101-107). Sorafenib (NEXAVAR™; BAY-43-9006; Bayer and Onyx) is an oral cytostatic pan-kinase inhibitor, approved by the FDA for advanced renal cell carcinoma, and is being developed for the potential treatment of additional, various cancers (Ahmad et al. (2004) Clinical Cancer Res. 10(18, Pt. 2):6388S-6392S; Lee et al. (2003) Current Opinion in Invest. Drugs 4(6):757-763). Sorafenib prevents tumor growth by inhibition of tumor cell proliferation and tumor angiogenesis (Clark et al. (2005) Clinical Cancer Res. 11(15):5472-5480; Yu et al. (2005) Oncogene 24(46):6861-6869; Wilhelm et al. (2004) Cancer Res. 64(19): 7099-7109).

Use of these targeted therapies is not without limitations such as the development of resistance and the lack of tumor response in the general population. The availability of newer inhibitors and improved patient selection will help overcome these problems in the future. There remains a significant need to develop Raf kinase inhibitors for the treatment of solid tumors

SUMMARY OF THE INVENTION

In one aspect, the invention relates to a group of novel compounds that are inhibitors of Raf kinases, in particular inhibitors of B-Raf kinase. The compounds of the invention can be used in the treatment of hyperproliferative disorders such as cancer. Certain hyperproliferative disorders are characterized by the overactivation of Raf kinase function, for example by mutations or overexpression of the protein. Compounds of the invention are useful in the treatment of melanoma and other cancers of the skin, and at various stages of progression of the disease.

In one aspect, the compounds of the invention include a group of novel pyrazole compounds having Formulas Ia and Ib.

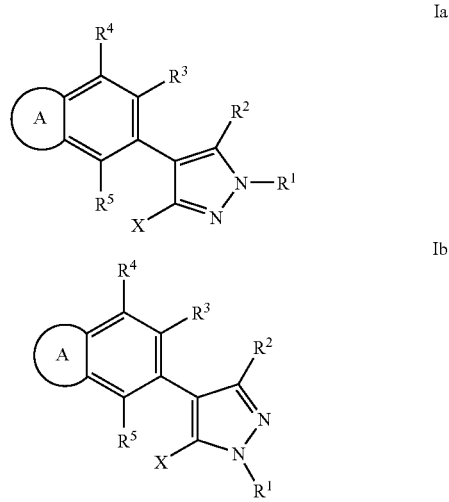

and stereoisomers, tautomers, solvates and pharmaceutically acceptable salts thereof, wherein:

the A-ring is: (i) a 5 or 6 membered heterocyclic ring having one or two heteroatoms independently selected from O, N, and S, (ii) a 5 or 6 membered carbocyclic ring optionally fused to a 5 or 6 membered heterocycle, or (iii) a phenyl ring, wherein said heterocyclic, carbocyclic and phenyl rings are optionally substituted with one or more groups independently selected from F, Cl, Br, I, —C(=Y)R$^{20}$, —C(=Y)OR$^{20}$, —C(=Y)NR$^{20}$R$^{21}$, NR$^{20}$R$^{21}$, —NR$^{20}$C(=Y)R$^{21}$, —NR$^{20}$C(=Y)OR$^{21}$, —NR$^{23}$C(=Y)NR$^{20}$R$^{21}$, =NOR$^{20}$, =NR$^{20}$, =N+(O)OR$^{20}$, =NNR$^{20}$R$^{21}$, =O, —OR$^{20}$, —OC(=Y)R$^{20}$, —OC(=Y)OR$^{20}$, —OC(=Y)NR$^{20}$R$^{21}$, —OS(O)$_2$(OR$^{20}$), —OP(=Y)(OR$^{20}$)(OR$^{21}$), —OP(OR$^{20}$)(OR$^{21}$), —P(=Y)(OR$^{20}$)(OR$^{21}$), —P(=Y)(OR)NR$^{20}$R$^{21}$, =S, —SR$^{20}$, —S(O)R$^{20}$, —S(O)$_2$R$^{20}$, —S(O)$_2$NR$^{20}$R$^{21}$, —S(O)(OR$^{20}$), —S(O)$_2$(OR$^{20}$), —SC(=Y)R$^{20}$, —SC(=Y)OR$^{20}$, —SC(=Y)NR$^{20}$R$^{21}$, C$_1$-C$_8$ alkyl, C$_2$-C$_8$ alkenyl, C$_2$-C$_8$ alkynyl, C$_6$-C$_{20}$ aryl, C$_3$-C$_{12}$ carbocyclyl, C$_2$-C$_{20}$ heterocyclyl, and a protecting group, and wherein said alkyl, alkenyl, alkynyl, aryl, carbocyclyl and heterocyclyl are optionally and independently substituted with one or more groups independently selected from F, Cl, Br, I, —C(=Y)R$^{20}$, —C(=Y)OR$^{20}$, —C(=Y)NR$^{20}$R$^{21}$, —NR$^{20}$R$^{21}$, —NR$^{20}$C(=Y)R$^{21}$, —NR$^{20}$C(=Y)OR$^{21}$, —NR$^{23}$C(=Y)NR$^{20}$R$^{21}$, —OR$^{20}$, —OC(=Y)R$^{20}$, —OC(=Y)OR$^{20}$, —OC(=Y)NR$^{20}$R$^{21}$, —OS(O)$_2$(OR$^{20}$), —OP(=Y)(OR$^{20}$)(OR$^{21}$), —OP(OR$^{20}$)(OR$^{21}$), —P(=Y)(OR$^{20}$)(OR$^{21}$), —P(=Y)(OR)NR$^{20}$R$^{21}$, —SR$^{20}$, —S(O)R$^{20}$, —S(O)$_2$R$^{20}$, —S(O)$_2$NR$^{20}$R$^{21}$, —S(O)(OR$^{21}$), —S(O)$_2$(OR$^{20}$), —SC(=Y)R$^{20}$, —SC(=Y)OR$^{20}$, —SC(=Y)NR$^{20}$R$^{21}$, C$_1$-C$_8$ alkyl, C$_2$-C$_8$ alkenyl, C$_2$-C$_8$ alkynyl, C$_6$-C$_{20}$ aryl, C$_3$-C$_{12}$ carbocyclyl, and C$_2$-C$_{20}$ heterocyclyl;

X is selected from a C$_2$-C$_{20}$ heterocyclyl, a C$_3$-C$_{12}$ carbocyclyl, and a C$_6$-C$_{20}$ aryl, wherein said heterocycle, carbocyclyl and aryl are optionally substituted with one or more groups independently selected from F, Cl, Br, I, —C(=Y)R$^{20}$, —C(=Y)OR$^{20}$, —C(=Y)NR$^{20}$R$^{21}$, —NR$^{20}$R$^{21}$, —NR$^{20}$C(=Y)R$^{21}$, —NR$^{20}$C(=Y)OR$^{21}$, —NR$^{23}$C(=Y)NR$^{20}$R$^{21}$, —OR$^{20}$, —OC(=Y)R$^{20}$, —OC(=Y)OR$^{20}$, —OC(=Y)NR$^{20}$R$^{21}$, —OS(O)$_2$(R$^{20}$), —OP(=Y)(OR$^{20}$)(OR$^{21}$), —OP(OR$^{20}$)(OR$^{21}$), —P(=Y)(OR$^{20}$)(OR$^{21}$), —P(=Y)(OR$^{23}$)NR$^{20}$R$^{21}$, —SR$^{20}$, —S(O)R$^{20}$, —S(O)$_2$R$^{20}$, —S(O)$_2$NR$^{20}$R$^{21}$, —S(O)(OR$^{20}$), —S(O)$_2$(OR$^{20}$), —SC(=Y)R$^{20}$, —SC(=Y)OR$^{20}$, —SC(=Y)NR$^{20}$R$^{21}$, 5-7 membered ring lactam, 5-7 membered ring lactone, 5-7 membered ring sultam, C$_1$-C$_8$ alkyl, C$_2$-C$_8$ alkenyl, C$_2$-C$_8$ alkynyl, C$_3$-C$_{12}$ carbocyclyl, C$_6$-C$_{20}$ aryl, and C$_2$-C$_{20}$ heterocyclyl, wherein said alkyl, alkenyl, alkynyl, carbocyclyl, more groups independently selected from F, Cl, Br, I, OR$^{20}$, NR$^{20}$R$^{21}$ —SR$^{20}$, -aryl, and heterocyclyl are optionally substituted with one or S(O)R$^{20}$, —S(O)$_2$R$^{20}$, alkyl, alkenyl, alkynyl, carbocyclyl, aryl, and heterocyclyl;

R$^1$ is selected from H, C$_1$-C$_8$ alkyl, C$_2$-C$_8$ alkenyl, C$_2$-C$_8$ alkynyl, (C$_1$-C$_8$alkyl)NR$^{20}$R$^{21}$, C$_2$-C$_{20}$ heterocyclyl, C$_3$-C$_{12}$ carbocyclyl, and C$_6$-C$_{20}$ aryl, wherein said alkyl, alkenyl, alkynyl, heterocycle, carbocyclyl and aryl are optionally substituted with one or more groups independently selected from F, Cl, Br, I, —C(=Y)R$^{20}$, —C(=Y)OR$^{20}$, —C(=Y)NR$^{20}$R$^{21}$, —NR$^{20}$R$^{21}$, OR$^{20}$, CN, C(=O)NR$^{20}$R$^{21}$, C(=O)OR$^{20}$, alkyl, (C$_1$-C$_8$alkyl)NR$^{20}$R$^{21}$, and heterocyclyl;

R$^2$ is selected from H, F, Cl, Br, I, —C(=Y)R$^{20}$, —C(=Y)OR$^{20}$, —C(=Y)NR$^{20}$R$^{21}$, —OR$^{20}$, —OC(=Y)R$^{20}$, —OC(=Y)OR$^{20}$, —OC(=Y)NR$^{20}$R$^{21}$, —OS(O)$_2$(OR$^{20}$), —OP(=Y)(OR$^{20}$)(OR$^{21}$), —OP(OR$^{20}$)(OR$^{21}$), —P(=Y)(OR$^{20}$)(OR$^{21}$), —P(=Y)(OR)NR$^{20}$R$^{21}$, —SR$^{20}$, —S(O)R$^{20}$, —S(O)$_2$R$^{20}$, —S(O)$_2$NR$^{20}$R$^{21}$, —S(O)(OR$^{20}$), —S(O)$_2$(OR$^{20}$), —SC(=Y)R$^{20}$, —SC(=Y)OR$^{20}$, —SC(=Y)NR$^{20}$R$^{21}$, 5-7 membered ring lactam, 5-7 membered ring lactone, 5-7 membered ring sultam, C$_1$-C$_8$ alkyl, C$_2$-C$_8$ alkenyl, C$_2$-C$_8$ alkynyl, C$_3$-C$_{12}$ carbocyclyl, C$_6$-C$_{20}$ aryl, and C$_2$-C$_{20}$ heterocyclyl, wherein said alkyl, alkenyl, alkynyl, carbocyclyl, aryl, and heterocyclyl are optionally substituted with one or more groups independently selected from F, Cl, Br, I, OR$^{20}$, NR$^{20}$R$^{21}$ —SR$^{20}$, —S(O)R$^{20}$, —S(O)$_2$R$^{20}$, alkyl, alkenyl, alkynyl, carbocyclyl, aryl, and heterocyclyl, or R$^1$ and R$^2$ of Formula Ia together with the atoms to which they are attached optionally form a saturated, partially unsaturated or aromatic 5 or 6 membered fused heterocycle ring having at least two heteroatoms independently selected from O, N and S, wherein said heterocycle ring is optionally substituted with one or more groups independently selected from F, Cl, Br, I, —C(=Y)R$^{20}$, —C(=Y)OR$^{20}$, —C(=Y)NR$^{20}$R$^{21}$, —NR$^{20}$R$^{21}$, —NR$^{20}$C(=Y)R$^{21}$, —NR$^{20}$C(=Y)OR$^{21}$, —NR$^{23}$C(=Y)NR$^{20}$R$^{21}$, —OR$^{20}$, —OC(=Y)R$^{20}$, —OC(=Y)OR$^{20}$, —OC(=Y)NR$^{20}$R$^{21}$, —OS(O)$_2$(OR$^{20}$), —OP(=Y)(OR$^{20}$)(OR$^{21}$), —OP(OR$^{20}$)(OR$^{21}$), —P(=Y)(OR$^{20}$)(OR$^{21}$), —P(=Y)(OR$^{23}$)NR$^{20}$R$^{21}$, —SR$^{20}$, —S(O)R$^{20}$, —S(O)$_2$R$^{20}$, —S(O)$_2$NR$^{20}$R$^{21}$, —S(O)(OR$^{20}$), —S(O)$_2$(OR$^{20}$), —SC(=Y)R$^{20}$, —SC(=Y)OR$^{20}$, —SC(=Y)NR$^{20}$R$^{21}$, 5-7 membered ring lactam, 5-7 membered ring lactone, 5-7 membered ring sultam, C$_1$-C$_8$ alkyl, C$_2$-C$_8$ alkenyl, C$_2$-C$_8$ alkynyl, C$_3$-C$_{12}$ carbocyclyl, C$_6$-C$_{20}$ aryl, and C$_2$-C$_{20}$ heterocyclyl, wherein said alkyl, alkenyl, alkynyl, carbocyclyl, aryl, and heterocyclyl are optionally substituted with one or more groups independently selected from F, Cl, Br, I, OR$^{20}$, NR$^{20}$R$^{21}$ —SR$^{20}$, —S(O)R$^{20}$, —S(O)$_2$R$^{20}$, alkyl, alkenyl, alkynyl, carbocyclyl, aryl, and heterocyclyl;

R$^3$, R$^4$, and R$^5$ are independently selected from H, F, Cl, Br, I, —C(=Y)R$^{20}$, —C(=Y)OR$^{20}$, —C(=Y)NR$^{20}$R$^{21}$, —NR$^{20}$R$^{21}$, —NR$^{20}$C(=Y)R$^{21}$, —NR$^{20}$C(=Y)OR$^{21}$, —NR$^{23}$C(=Y)NR$^{20}$R$^{21}$, —OR$^{20}$, —OC(=Y)R$^{20}$, —OC(=Y)OR$^{20}$, —OC(=Y)NR$^{20}$R$^{21}$, —OS(O)$_2$(OR$^{20}$), —OP(=Y)(OR$^{20}$)(OR$^{21}$), —OP(OR$^{20}$)(OR$^{21}$), —P(=Y)(OR$^{20}$)(OR$^{21}$), —P(=Y)(OR$^{23}$)NR$^{20}$R$^{21}$, —SR$^{20}$, —S(O)R$^{20}$, —S(O)$_2$R$^{20}$, —S(O)$_2$NR$^{20}$R$^{21}$, —S(O)(OR$^{20}$), —S(O)$_2$(OR$^{20}$), —SC(=Y)R$^{20}$, —SC(=Y)OR$^{20}$, —SC(=Y)NR$^{20}$R$^{21}$, 5-7 membered ring lactam, 5-7 membered ring lactone, 5-7 membered ring sultam, C$_1$-C$_8$ alkyl, C$_2$-C$_8$ alkenyl, C$_2$-C$_8$ alkynyl, C$_3$-C$_{12}$ carbocyclyl, C$_6$-C$_{20}$ aryl, and C$_2$-C$_{20}$ heterocyclyl, wherein said alkyl, alkenyl, alkynyl, carbocyclyl, aryl, and heterocyclyl are optionally substituted with one or more groups independently selected from F, Cl, Br, I, OR$^{20}$, NR$^{20}$R$^{21}$ —SR$^{20}$, —S(O)R$^{20}$, —S(O)$_2$R$^{20}$, alkyl, alkenyl, alkynyl, carbocyclyl, aryl, and heterocyclyl;

R$^{20}$ and R$^{21}$ are independently selected from H, C$_1$-C$_8$ alkyl, C$_2$-C$_8$ alkenyl, C$_2$-C$_8$ alkynyl, C$_6$-C$_{20}$ aryl, C$_2$-C$_{20}$ heterocyclyl, and a protecting group, wherein said alkyl, alkenyl, alkynyl, aryl, and heterocyclyl are optionally and independently substituted with one or more groups independently selected from F, Cl, Br, I, —C(=Y)R$^a$, —C(=Y)OR$^a$, —C(=Y)NR$^a$R$^b$, —OR$^a$, —OC(=Y)R$^a$, —OC(=Y)OR$^a$, —OC(=Y)NR$^a$R$^b$, —OS(O)$_2$(OR$^a$), —OP(=Y)(OR$^a$)(OR$^b$), —OP(OR$^a$)(OR$^b$), —P(=Y)(OR$^a$)(OR$^b$), —P(=Y)(OR)NR$^a$R$^b$, —SR$^a$, —S(O)R$^a$, —S(O)$_2$R$^a$, —S(O)$_2$NR$^a$R$^b$, —S(O)(OR$^a$), —S(O)$_2$(OR$^a$), —SC(=Y)R$^a$, —SC(=Y)OR$^a$, and —SC(=Y)NR$^a$R$^b$, or R$^{20}$ and R$^{21}$ together with the atoms to which they are attached form a heterocyclic ring, wherein said heterocyclic ring is optionally substituted with one or more groups independently selected from F, Cl, Br, I, alkyl, alkenyl and alkynyl;

R$^{23}$ is H, C$_1$-C$_8$ alkyl, C$_2$-C$_8$ alkenyl, C$_2$-C$_8$ alkynyl, C$_6$-C$_{20}$ aryl, C$_2$-C$_{20}$ heterocyclyl, or a protecting group;

R$^a$ and R$^b$ are independently H, C$_1$-C$_8$ alkyl, C$_2$-C$_8$ alkenyl, C$_2$-C$_8$ alkynyl, C$_6$-C$_{20}$ aryl, or C$_2$-C$_{20}$ heterocyclyl;

Y is independently O, S, NR$^{20}$, $^+$N(O)R$^{20}$, N(OR$^{20}$), $^+$N(O)(OR$^{20}$), or N—NR$^{20}$R$^{21}$; and protecting group is selected from trialkylsilyl, dialkylphenylsilyl, benzoate, benzyl, benzyloxymethyl, methyl, methoxymethyl, triarylmethyl, phthalimido, t-butoxycarbonyl (BOC), benzyloxycarbonyl (CBz), 9-fluorenylmethylenoxycarbonyl (Fmoc), and tetrahydropyranyl.

One aspect of the invention is to provide methods of inhibiting Raf kinase activity by contacting these enzymes with an effective inhibitory amount of the novel inhibitors of the present invention, or a composition containing these compounds.

Another aspect of the invention are methods of treating such as, but not limited to, a hyperproliferative disorder (e.g., cancer), cardiovascular disease, neurodegenerative disease, or inflammatory disease, by administering to a mammal in need of such treatment an effective amount of one or more compounds of the invention, or a composition containing the compound and a carrier or excipient.

Another aspect of the invention are methods of treating cancer by administering to a mammal in need of such treatment an effective amount of one or more compounds of the invention in combination with one or more additional compounds having anti-cancer properties.

This invention also provides a compound of this invention for use in treating a disease or disorder such as, but not limited to, a hyperproliferative disorder (e.g., cancer), cardiovascular disease, neurodegenerative disease, or inflammatory disease.

An additional aspect of the invention is the use of a compound of this invention in the preparation of a medicament for the treatment or prevention of a disease or disorder such as, but not limited to, a hyperproliferative disorder (e.g., cancer), cardiovascular disease, neurodegenerative disease, or inflammatory disease.

Another aspect of the invention includes articles of manufacture, i.e. kits, comprising a pyrazolyl compound of Formulas Ia or Ib, a container, and a package insert or label indicating a treatment.

Another aspect of the invention includes methods of preparing, methods of synthesis, methods of separation, and methods of purification of the pyrazolyl compounds of Formula Ia and Ib. In addition, the invention includes novel intermediates for preparing the pyrazolyl compounds of Formula Ia and Ib.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

Definitions

Unless stated otherwise, the following terms and phrases as used herein are intended to have the following meanings:

The term "alkyl" as used herein refers to a saturated linear or branched-chain monovalent hydrocarbon radical of one to eighteen carbon atoms, wherein the alkyl radical may be optionally substituted independently with one or more substituents described below. Examples of alkyl groups include $C_1$-$C_8$ hydrocarbon moieties such as methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, cyclopropyl, cyclobutyl, cyclopentyl, cyclohexyl, cycloheptyl, and cyclooctyl. Alkyl groups are optionally substituted independently with one or more substituents described herein.

The term "alkenyl" refers to linear or branched-chain monovalent hydrocarbon radical of two to eighteen carbon atoms with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH═$CH_2$), allyl (—$CH_2$CH═$CH_2$), 1-cyclopent-1-enyl, 1-cyclopent-2-enyl, 1-cyclopent-3-enyl, 5-hexenyl, 1-cyclohex-1-enyl, 1-cyclohex-2-enyl, and 1-cyclohex-3-enyl. Alkenyl groups are optionally substituted independently with one or more substituents described herein.

The term "alkynyl" refers to a linear or branched monovalent hydrocarbon radical of two to eighteen carbon atoms with at least one site of unsaturation, i.e., a carbon-carbon, sp triple bond, wherein the alkynyl radical may be optionally substituted independently with one or more substituents described herein. Examples include, but are not limited to, ethynyl (—C≡CH) and propynyl (propargyl, —$CH_2$C≡CH). Alkynyl groups are optionally substituted independently with one or more substituents described herein.

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to, methylene (—$CH_2$—) 1,2-ethyl (—$CH_2CH_2$—), 1,3-propyl (—$CH_2CH_2CH_2$—), 1,4-butyl (—$CH_2CH_2CH_2CH_2$—), and the like. Alkylene groups are optionally substituted independently with one or more substituents described herein.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to, 1,2-ethylene (—CH═CH—). Alkenylene groups are optionally substituted independently with one or more substituents described herein.

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to, acetylene (—C≡C—), propargyl (—$CH_2$C≡C—), and 4-pentynyl (—$CH_2CH_2CH_2$C≡C—). Alkynylene groups are optionally substituted independently with one or more substituents described herein.

"Aryl" means a monovalent aromatic hydrocarbon radical of 6-20 carbon atoms derived by the removal of one hydrogen atom from a single carbon atom of a parent aromatic ring system. Some aryl groups are represented in the exemplary structures as "Ar". Aryl includes a bicyclic radical comprising an aromatic ring with a fused non-aromatic or partially saturated ring. Typical aryl groups include, but are not limited to, radicals derived from benzene, substituted benzene, naphthalene, anthracene, biphenyl, indenyl, indanyl, 1,2-dihydronapthalene, 1,2,3,4-tetrahydronapthyl, and the like. Aryl groups are optionally substituted independently with one or more substituents described herein.

The terms "heterocycle," "heterocyclyl", "heterocyclic ring" and "heteroaryl" refer to a saturated, a partially unsaturated (i.e., having one or more double and/or triple bonds within the ring), or aromatic carbocyclic radical of 3 to 20 ring atoms in which at least one ring atom is a heteroatom independently selected from nitrogen, oxygen and sulfur, the remaining ring atoms being carbon, where one or more ring atoms is optionally substituted independently with one or more substituents described below. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566. The heterocyclyl may be a carbon-linked radical or heteroatom-linked radical. The term "heterocycle" includes heterocycloalkoxy. "Heterocyclyl" also includes radicals where heterocycle radicals are fused with a carbocyclic, heterocyclic, aromatic or heteroaromatic ring. Examples of heterocyclic radicals include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco [3.1.0]hexanyl, 3-azabicyclo[4.1.0]heptanyl, azabicyclo [2.2.2]hexanyl, 3H-indolyl quinolizinyl and N-pyridyl ureas. Spiro moieties are also included within the scope of this definition. Examples of a heterocyclic group wherein 2 ring carbon atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" includes 1) monocyclic aromatic 5-, 6-, and 7-membered rings containing one or more heteroatoms independently selected from nitrogen, oxygen, and sulfur, and 2) fused ring systems of 8 to 20 atoms wherein at least one aromatic ring contains one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle may be C-attached or N-attached where such is possible. By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. (2-pyridyl, 3-pyridyl, 4-pyridyl, 5-pyridyl, 6-pyridyl).

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

"Carbocycle", "carbocyclyl" and "cycloalkyl" mean a non-aromatic, saturated or unsaturated ring having 3 to 12 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system, or as bridged systems such as bicyclo [2.2.1]heptane, bicyclo[2.2.2]octane, and bicyclo[3.2.2] nonane. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl.

"Substituted alkyl", "substituted aryl", "substituted heterocyclyl", and "substituted carbocyclyl" mean alkyl, aryl, heterocyclyl and carbocyclyl respectively, in which one or more hydrogen atoms are each independently replaced with a substituent. Typical substituents include, but are not limited to, X, R, O⁻, —OR, —SR, —NR$_2$, —NR$_3$, =NR, =N—OR, =O, —CX$_3$, —CN, —OCN, —SCN, —N=C=O, —NCS, —NO, —NO$_2$, =N$_2$, —N$_3$, NC(=O)R, —C(=O)R, —C(=O)NR$_2$, —SO$_3$⁻, —SO$_3$H, —S(=O)$_2$R, —OS(=O)$_2$OR, —S(=O)$_2$NR, —S(=O)R, —OP(=O)(OR)$_2$, —P(=O)(OR)$_2$, —PO$_3$, —PO$_3$H$_2$, —C(=O)R, —C(=O)X, —C(=S)R, —CO$_2$R, —CO$_2$⁻, —C(=S)OR, —C(=O)SR, —C(=S)SR, —C(=O)NR$_2$, —C(=S)NR$_2$, and —C(=NR)NR$_2$, where each X is independently a halogen (F, Cl, Br, or I), and each R is independently H, C$_1$-C$_{18}$ alkyl, C$_6$-C$_{20}$ aryl, C$_3$-C$_{14}$ heterocycle, protecting group or prodrug moiety. Alkylene, alkenylene, and alkynylene groups as described above may also be similarly substituted.

The terms "treat" or "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The term "prodrug" as used in this application refers to a precursor or derivative form of a pharmaceutically active substance that is less cytotoxic to tumor cells compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "liposome" is a small vesicle composed of various types of lipids, phospholipids and/or surfactant which is useful for delivery of a drug (such as the Raf inhibitors disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The phrase "pharmaceutically acceptable salt," as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" or "Pg" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, phthalimido, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups include acetyl, trialkylsilyl, dialkylphenylsilyl, benzoyl, benzyl, benzyloxymethyl, methyl, methoxymethyl, triarylmethyl, and tetrahydropyranyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitroethyl and the like. For a general description of protecting groups and their use, see T. W. Greene and P. Wuts, Protective Groups in Organic Synthesis, Third Ed., John Wiley & Sons, New York, 1999; and P. Kocienski, Protecting Groups, Third Ed., Verlag, 2003.

The term "animal" refers to humans (male or female), companion animals (e.g., dogs, cats and horses), food-source animals, zoo animals, marine animals, birds and other similar animal species.

The phrase "pharmaceutically acceptable" indicates that the substance or composition must be compatible chemically and/or toxicologically, with the other ingredients comprising a formulation, and/or the mammal being treated therewith.

Pyrazolyl RAF Inhibitor Compounds

The present invention provides compounds having Formulas Ia and Ib, and pharmaceutical formulations thereof, that are potentially useful in the treatment of diseases, conditions and/or disorders modulated by Raf kinases. Formula Ia and Ib compounds include:

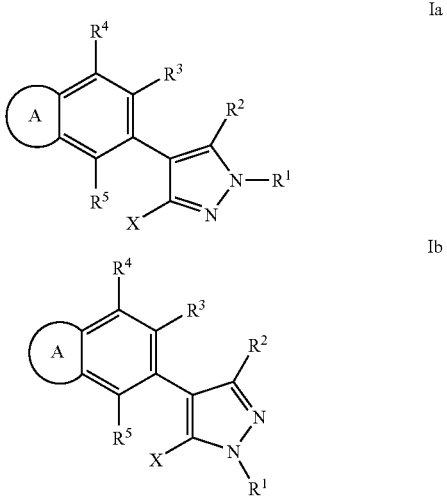

and stereoisomers, tautomers, solvates and pharmaceutically acceptable salts thereof, wherein:

the A-ring is: (i) a 5 or 6 membered heterocyclic ring having one or two heteroatoms independently selected from O, N, and S, (ii) a 5 or 6 membered carbocyclic ring optionally fused to a 5 or 6 membered heterocycle, or (iii) a phenyl ring, wherein said heterocyclic, carbocyclic and phenyl rings are optionally substituted with one or more groups independently selected from F, Cl, Br, I, —$C(=Y)R^{20}$, —$C(=Y)OR^{20}$, —$C(=Y)NR^{20}R^{21}$, $NR^{20}R^{21}$, —$NR^{20}C(=Y)R^{21}$, —$NR^{20}C(=Y)OR^{21}$, —$NR^{23}C(=Y)NR^{20}R^{21}$, =$NOR^{20}$, =$NR^{20}$, =$N+(O)OR^{20}$, =$NNR^{20}R^{21}$, =O, —$OR^{20}$, —$OC(=Y)R^{20}$, —$OC(=Y)OR^{21}$, —$OC(=Y)NR^{20}R^{21}$, —$OS(O)_2(OR^{21})$, —$OP(=Y)(OR^{20})(OR^{21})$, —$OP(OR^{20})(OR^{21})$, —$P(=Y)(OR^{20})(OR^{21})$, —$P(=Y)(OR)NR^{20}R^{21}$, =S, —$SR^{20}$, —$S(O)R^{20}$, —$S(O)_2R^{20}$, —$S(O)_2NR^{20}R^{21}$, —$S(O)(OR^{20})$, —$S(O)_2(OR^{20})$, —$SC(=Y)R^{20}$, —$SC(=Y)OR^{20}$, —$SC(=Y)NR^{20}R^{21}$, $C_1$-$C_8$ alkyl, $C_2$-$C_8$ alkenyl, $C_2$-$C_8$ alkynyl, $C_6$-$C_{20}$ aryl, $C_3$-$C_{12}$ carbocyclyl, $C_2$-$C_{20}$ heterocyclyl, and a protecting group, and wherein said alkyl, alkenyl, alkynyl, aryl, carbocyclyl and heterocyclyl are optionally and independently substituted with one or more groups independently selected from F, Cl, Br, I, —$C(=Y)R^{20}$, —$C(=Y)OR^{20}$, —$C(=Y)NR^{20}R^{21}$, $NR^{20}R^{21}$, —$NR^{20}C(=Y)R^{21}$, —$NR^{20}C(=Y)OR^{21}$, —$NR^{23}C(=Y)NR^{20}R^{21}$, —$OR^{20}$, —$OC(=Y)R^{20}$, —$OC(=Y)OR^{20}$, —$OC(=Y)NR^{20}R^{21}$, —$OS(O)_2(OR^{20})$, —$OP(=Y)(OR^{20})(OR^{21})$, —$OP(OR^{20})(OR^{21})$, —$P(=Y)(OR^{20})(O^{21})$, —$P(=Y)(OR)NR^{20}R^{21}$, —$SR^{20}$, —$S(O)R^{20}$, —$S(O)_2R^{20}$, —$S(O)_2NR^{20}R^{21}$, —$S(O)(OR^{20})$, —$S(O)_2(OR^{20})$, —$SC(=Y)R^{20}$, —$SC(=Y)OR^{20}$, —$SC(=Y)NR^{20}R^{21}$, $C_1$-$C_8$ alkyl, $C_2$-$C_8$ alkenyl, $C_2$-$C_8$ alkynyl, $C_6$-$C_{20}$ aryl, $C_3$-$C_{12}$ carbocyclyl and $C_2$-$C_{20}$ heterocyclyl;

X is selected from a $C_2$-$C_{20}$ heterocyclyl, a $C_3$-$C_{12}$ carbocyclyl, and a $C_6$-$C_{20}$ aryl, wherein said heterocycle, carbocyclyl and aryl are optionally substituted with one or more groups independently selected from F, Cl, Br, I, —$C(=Y)R^{20}$, —$C(=Y)OR^{20}$, —$C(=Y)NR^{20}R^{21}$, —$NR^{20}R^{21}$, —$NR^{20}C(=Y)R^{21}$, —$NR^{20}C(=Y)OR^{21}$, —$NR^{23}C(=Y)NR^{20}R^{21}$, —$OR^{20}$, —$OC(=Y)R^{20}$, —$OC(=Y)OR^{20}$, —$OC(=Y)NR^{20}R^{21}$, —$OS(O)_2(OR^{20})$, —$OP(=Y)(OR^{20})(OR^{21})$, —$OP(OR^{20})(OR^{21})$, —$P(=Y)(OR^{20})(OR^{21})$, —$P(=Y)(OR^{23})NR^{20}R^{21}$, —$SR^{20}$, —$S(O)R^{20}$, —$S(O)_2R^{20}$, —$S(O)_2NR^{20}R^{21}$, —$S(O)(OR^{20})$, —$S(O)_2(OR^{20})$, —SC(=Y)R$^{20}$, —SC(=Y)OR$^{20}$, —SC(=Y)NR$^{20}$R$^{21}$, 5-7 membered ring lactam, 5-7 membered ring lactone, 5-7 membered ring sultam, C$_1$-C$_8$ alkyl, C$_2$-C$_8$ alkenyl, C$_2$-C$_8$ alkynyl, C$_3$-C$_{12}$ carbocyclyl, C$_6$-C$_{20}$ aryl, and C$_2$-C$_{20}$ heterocyclyl, wherein said alkyl, alkenyl, alkynyl, carbocyclyl, aryl, and heterocyclyl are optionally substituted with one or more groups independently selected from F, Cl, Br, I, OR$^{20}$, NR$^{20}$R$^{21}$ —SR$^{20}$, —S(O)R$^{20}$, —S(O)$_2$R$^{20}$, alkyl, alkenyl, alkynyl, carbocyclyl, aryl, and heterocyclyl;

R$^1$ is selected from H, C$_1$-C$_8$ alkyl, C$_2$-C$_8$ alkenyl, C$_2$-C$_8$ alkynyl, (C$_1$-C$_8$-alkyl)NR$^{20}$R$^{21}$, C$_2$-C$_{20}$ heterocyclyl, C$_3$-C$_{12}$ carbocyclyl, and C$_6$-C$_{20}$ aryl, wherein said alkyl, alkenyl, alkynyl, heterocycle, carbocyclyl and aryl are optionally substituted with one or more groups independently selected from F, Cl, Br, I, —C(=Y)R$^{20}$, —C(=Y)OR$^{20}$, —C(=Y)NR$^{20}$R$^{21}$, —NR$^{20}$R$^{21}$, OR$^{20}$, CN, C(=O)NR$^{20}$R$^{21}$, C(=O)R$^{20}$, alkyl, (C$_1$-C$_8$-alkyl)NR$^{20}$R$^{21}$, and heterocyclyl;

R$^2$ is selected from H, F, Cl, Br, I, —C(=Y)R$^{20}$, —C(=Y)OR$^{20}$, —C(=Y)NR$^{20}$R$^{21}$, —OR$^{20}$, —OC(=Y)R$^{20}$, —OC(=Y)OR$^{20}$, —OC(=Y)NR$^{20}$R$^{21}$, —OS(O)$_2$(OR$^{20}$), —OP(=Y)(OR$^{20}$)(OR$^{21}$), —OP(OR$^{20}$)(OR$^{21}$), —P(=Y)(OR$^{20}$)(OR$^{21}$), —P(=Y)(OR)NR$^{20}$R$^{21}$, —SR$^{20}$, —S(O)R$^{20}$, —S(O)$_2$R$^{20}$, —S(O)$_2$NR$^{20}$R$^{21}$, —S(O)(OR$^{20}$), —S(O)$_2$(OR$^{20}$), —SC(=Y)R$^{20}$, —SC(=Y)OR$^{20}$, —SC(=Y)NR$^{20}$R$^{21}$, 5-7 membered ring lactam, 5-7 membered ring lactone, 5-7 membered ring sultam, C$_1$-C$_8$ alkyl, C$_2$-C$_8$ alkenyl, C$_2$-C$_8$ alkynyl, C$_3$-C$_{12}$ carbocyclyl, C$_6$-C$_{20}$ aryl, and C$_2$-C$_{20}$ heterocyclyl, wherein said alkyl, alkenyl, alkynyl, carbocyclyl, aryl, and heterocyclyl are optionally substituted with one or more groups independently selected from F, Cl, Br, I, OR$^{20}$, NR$^{20}$R$^{21}$ —SR$^{20}$, —S(O)R$^{20}$, —S(O)$_2$R$^{20}$, alkyl, alkenyl, alkynyl, carbocyclyl, aryl, and heterocyclyl, or R$^1$ and R$^2$ of Formula Ia together with the atoms to which they are attached optionally form a saturated, partially unsaturated or aromatic 5 or 6 membered fused heterocycle ring having at least two heteroatoms independently selected from O, N and S, wherein said heterocycle ring is optionally substituted with one or more groups independently selected from F, Cl, Br, I, —C(=Y)R$^{20}$, —C(=Y)OR$^{20}$, —C(=Y)NR$^{20}$R$^{21}$, —NR$^{20}$R$^{21}$, —NR$^{20}$C(=Y)R$^{21}$, —NR$^{20}$C(=Y)OR$^{21}$, —NR$^{23}$C(=Y)NR$^{20}$R$^{21}$, —OR$^{20}$, —OC(=Y)R$^{20}$, —OC(=Y)OR$^{20}$, —OC(=Y)NR$^{21}$R$^{21}$, —OS(O)$_2$(OR$^{20}$), —OP(=Y)(OR$^{20}$)(OR$^{21}$), —OP(OR$^{20}$)(OR$^{21}$), —P(=Y)(OR$^{20}$)(OR$^{21}$), —P(=Y)(OR$^{23}$)NR$^{20}$R$^{21}$, —SR$^{20}$, —S(O)R$^{20}$, —S(O)$_2$R$^{20}$, —S(O)$_2$NR$^{20}$R$^{21}$, —S(O)(OR$^{20}$), —S(O)$_2$(OR$^{20}$), —SC(=Y)R$^{20}$, —SC(=Y)OR$^{20}$, —SC(=Y)NR$^{20}$R$^{21}$, 5-7 membered ring lactam, 5-7 membered ring lactone, 5-7 membered ring sultam, C$_1$-C$_8$ alkyl, C$_2$-C$_8$ alkenyl, C$_2$-C$_8$ alkynyl, C$_3$-C$_{12}$ carbocyclyl, C$_6$-C$_{20}$ aryl, and C$_2$-C$_{20}$ heterocyclyl, wherein said alkyl, alkenyl, alkynyl, carbocyclyl, aryl, and heterocyclyl are optionally substituted with, one or more groups independently selected from F, Cl, Br, I, OR$^{20}$, NR$^{20}$R$^{21}$ —SR$^{20}$, —S(O)R$^{20}$, —S(O)$_2$R$^{20}$, alkyl, alkenyl, alkynyl, carbocyclyl, aryl, and heterocyclyl;

R$^3$, R$^4$, and R$^5$ are independently selected from H, F, Cl, Br, I, —C(=Y)R$^{20}$, —C(=Y)OR$^{20}$, —C(=Y)NR$^{20}$R$^{21}$, —NR$^{20}$R$^{21}$, —NR$^{20}$C(=Y)R$^{21}$, —NR$^{20}$C(=Y)OR$^{21}$, —NR$^{23}$C(=Y)NR$^{20}$R$^{21}$, —OR$^{20}$, —OC(=Y)R$^{20}$, —OC(=Y)OR$^{20}$, —OC(=Y)NR$^{20}$R$^{21}$, —OS(O)$_2$(OR$^{20}$), —OP(=Y)(OR$^{20}$)(OR$^{21}$), —OP(OR$^{20}$)(OR$^{21}$), —P(=Y)(OR$^{20}$)(OR$^{21}$), —P(=Y)(OR$^{23}$)NR$^{20}$R$^{21}$, —SR$^{20}$, —S(O)R$^{20}$, —S(O)$_2$R$^{20}$, —S(O)$_2$NR$^{20}$R$^{21}$, —S(O)(OR$^{20}$), —S(O)$_2$(OR$^{20}$), —SC(=Y)R$^{20}$, —SC(=Y)OR$^{20}$, —SC(=Y)NR$^{20}$R$^{21}$, 5-7 membered ring lactam, 5-7 membered ring lactone, 5-7 membered ring sultam, C$_1$-C$_8$ alkyl, C$_2$-C$_8$ alkenyl, C$_2$-C$_8$ alkynyl, C$_3$-C$_{12}$ carbocyclyl, C$_6$-C$_{20}$ aryl, and C$_2$-C$_{20}$ heterocyclyl, wherein said alkyl, alkenyl, alkynyl, carbocyclyl, aryl, and heterocyclyl are optionally substituted with one or more groups independently selected from F, Cl, Br, I, OR$^{20}$, NR$^{20}$R$^{21}$ —SR$^{20}$, —S(O)R$^{20}$, —S(O)$_2$R$^{20}$, alkyl, alkenyl, alkynyl, carbocyclyl, aryl, and heterocyclyl;

R$^{20}$ and R$^{21}$ are independently selected from H, C$_1$-C$_8$ alkyl, C$_2$-C$_8$ alkenyl, C$_2$-C$_8$ alkynyl, C$_6$-C$_{20}$ aryl, C$_2$-C$_{20}$ heterocyclyl, and a protecting group, wherein said alkyl, alkenyl, alkynyl, aryl, and heterocyclyl are optionally and independently substituted with one or more groups independently selected from F, Cl, Br, I, —C(=Y)R$^a$, —C(=Y)OR$^a$, —C(=Y)NR$^a$R$^b$, —OR$^a$, —OC(=Y)R$^a$, —OC(=Y)OR$^a$, —OC(=Y)NR$^a$R$^b$, —OS(O)$_2$(OR$^a$), —OP(=Y)(OR$^a$)(OR$^b$), —OP(OR$^a$)(OR$^b$), —P(=Y)(OR$^a$)(OR$^b$), —P(=Y)(OR)NR$^a$R$^b$, —SR$^a$, —S(O)R$^a$, —S(O)$_2$R$^a$, —S(O)$_2$NR$^a$R$^b$, —S(O)(OR$^a$), —S(O)$_2$(OR$^a$), —SC(=Y)R$^a$, —SC(=Y)OR$^a$, and —SC(=Y)NR$^a$R$^b$, or R$^{20}$ and R$^{21}$ together with the atoms to which they are attached form a saturated or partially unsaturated heterocyclic ring, wherein said heterocyclic ring is optionally substituted with one or more groups independently selected from F, Cl, Br, I, alkyl, alkenyl and alkynyl;

R$^{23}$ is H, C$_1$-C$_8$ alkyl, C$_2$-C$_8$ alkenyl, C$_2$-C$_8$ alkynyl, C$_6$-C$_{20}$ aryl, C$_2$-C$_{20}$ heterocyclyl, or a protecting group;

R$^a$ and R$^b$ are independently H, C$_1$-C$_8$ alkyl, C$_2$-C$_8$ alkenyl, C$_2$-C$_8$ alkynyl, C$_6$-C$_{20}$ aryl, or C$_2$-C$_{20}$ heterocyclyl;

Y is independently O, S, NR$^{20}$, $^+$N(O)R$^{20}$, N(OR$^{20}$), $^+$N(O)(OR$^{20}$), or N—NR$^{20}$R$^{21}$; and protecting group is selected from trialkylsilyl, dialkylphenylsilyl, benzoate, benzyl, benzyloxymethyl, methyl, methoxymethyl, triarylmethyl, phthalimido, t-butoxycarbonyl (BOC), benzyloxycarbonyl (CBz), 9-fluorenylmethylenoxycarbonyl (Fmoc), and tetrahydropyranyl.

In another embodiment, Formula Ia and Ib compounds include where:

A forms: (i) a 5 or 6 membered fused heterocyclic ring having one or two heteroatoms independently selected from O, N, and S, (ii) a 5 or 6 membered carbocyclic ring, or (iii) a phenyl ring;

X is selected from a C$_2$-C$_{20}$ heterocycle, a C$_3$-C$_{12}$ carbocycle, and a C$_6$-C$_{20}$ aryl;

R$^1$ is selected from H, C$_1$-C$_8$ alkyl, C$_1$-C$_8$ alkenyl, C$_1$-C$_8$ alkynyl, a C$_2$-C$_{20}$ heterocycle, a C$_3$-C$_{12}$ carbocycle, and a C$_6$-C$_{20}$ aryl;

R$^2$ is selected from H, F, Cl, Br, I, —C(=Y)R, —C(=Y)OR, —C(=Y)NR$_2$, —OR, —OC(=Y)R, —OC(=Y)OR, —OC(=Y)(N(R)$_2$), —OS(O)$_2$(OR), —OP(=Y)(OR)$_2$, —OP(OR)$_2$, —P(=Y)(OR)$_2$, —P(=Y)(OR)NR$_2$, —SR, —S(O)R, —S(O)$_2$R, —S(O)$_2$NR, —S(O)(OR), —S(O)$_2$(OR), —SC(=Y)R, —SC(=Y)OR, —SC(=Y)NR$_2$, C$_1$-C$_8$ alkylhalide, C$_1$-C$_8$ alkylsulfonate, C$_1$-C$_8$ alkylamino, C$_1$-C$_8$ alkylhydroxyl, C$_1$-C$_8$ alkylthiol, 5-7 membered ring lactam, 5-7 membered ring lactone, 5-7 membered ring sultam, C$_1$-C$_8$ alkyl, C$_1$-C$_8$ alkenyl, C$_1$-C$_8$ alkynyl, C$_6$-C$_{20}$ aryl, and C$_2$-C$_{20}$ heterocycle;

R$^1$ and R$^2$ of Formula Ia optionally form a 5 or 6 membered fused heterocycle ring having at least two heteroatoms selected from O, N and S;

R$^3$, R$^4$, and R$^5$ are independently selected from H, F, Cl, Br, I, —C(=Y)R, —C(=Y)OR, —C(=Y)NR$_2$, —NR$_2$, —$^+$NR$_3$, —N(R)C(=Y)R, —N(R)C(=Y)OR, —N(R)C(=Y)NR$_2$, —OR, —OC(=Y)R, —OC(=Y)OR, —OC(=Y)(N(R)$_2$), —OS(O)$_2$(OR), —OP(=Y)(OR)$_2$, —OP(OR)$_2$, —P(=Y)(OR)$_2$, —P(=Y)(OR)NR$_2$, —SR, —S(O)R, —S(O)$_2$R, —S(O)$_2$NR, —S(O)(OR), —S(O)$_2$(OR), —SC(=Y)R, —SC(=Y)OR, —SC(=Y)NR$_2$, C$_1$-C$_8$ alkylhalide, C$_1$-C$_8$ alkylsulfonate, C$_1$-C$_8$ alkylamino, C$_1$-C$_8$ alkylhydroxyl, C$_1$-C$_8$ alkylthiol, 5-7 membered ring lactam, 5-7 membered ring lactone, 5-7 membered ring sultam, $C_1$-$C_8$ alkyl, $C_1$-$C_8$ alkenyl, $C_1$-$C_8$ alkynyl, $C_6$-$C_{20}$ aryl, and $C_2$-$C_{20}$ heterocycle;

R is H, $C_1$-$C_8$ alkyl, $C_1$-$C_8$ alkenyl, $C_1$-$C_8$ alkynyl, $C_6$-$C_{20}$ aryl, $C_2$-$C_{20}$ heterocycle, or a protecting group; and Y is independently O, S, NR, $^+$N(O)(R), N(OR), $^+$N(O)(OR), or N—NR$_2$;

each alkyl, alkenyl, alkynyl, aryl, carbocycle, and heterocycle is optionally and independently substituted with one or more substituents selected from F, Cl, Br, I, OH, OR, R, —C(=Y)R, —C(=Y)OR, —C(=Y)N(R)$_2$, —N(R)$_2$, —$^+$N(R)$_3$, —N(R)C(=Y)R, —N(R)C(=Y)OR, —N(R)C(=Y)N(R)$_2$, —SR, —OC(=Y)R, —OC(=Y)OR, —OC(=Y)(N(R)$_2$), —OS(O)$_2$(OR), —OP(=Y)(OR)$_2$, —OP(OR)$_2$, —P(=Y)(OR)$_2$, —P(=Y)(OR)NR$_2$, —S(O)R, —S(O)$_2$R, —S(O)$_2$NR, —S(O)(OR), —S(O)$_2$(OR), —SC(=Y)R, —SC(=Y)OR, =Y, and —SC(=Y)(N(R)$_2$).

Formula Ia and Ib compounds are regioisomers, differing by the attachment of R$^1$ at the non-equivalent nitrogen atoms of the pyrazole ring. Formula Ia and Ib compounds include stereoisomers, tautomers, solvates and pharmaceutically acceptable salts thereof, wherein:

In certain embodiments, R$^{20}$ and R$^{21}$ are optionally and independently a protecting group such as, but not limited to, trialkylsilyl, dialkylphenylsilyl, benzoate, benzyl, benzyloxymethyl, methyl, methoxymethyl, a triarylmethyl, phthalimido, t-butoxycarbonyl (BOC), benzyloxycarbonyl (CBz) and 9-fluorenylmethylenoxycarbonyl (Fmoc), or tetrahydropyranyl.

Exemplary embodiments of the A-ring include an optionally substituted a 5 or 6 membered fused heterocyclic ring having one or two heteroatoms independently selected from O, N, and S, such as tetrahydrofuranyl, dioxolanyl, tetrahydropyranyl, tetrahydropyridyl, piperazinyl, pyrrolidinyl, pyridyl, pyrimidinyl, dihydrothiophenyl, thiophenyl, imidazolyl, thiazolyl, oxazolyl, isoxazolyl, and pyrazolyl, including exemplary structures:

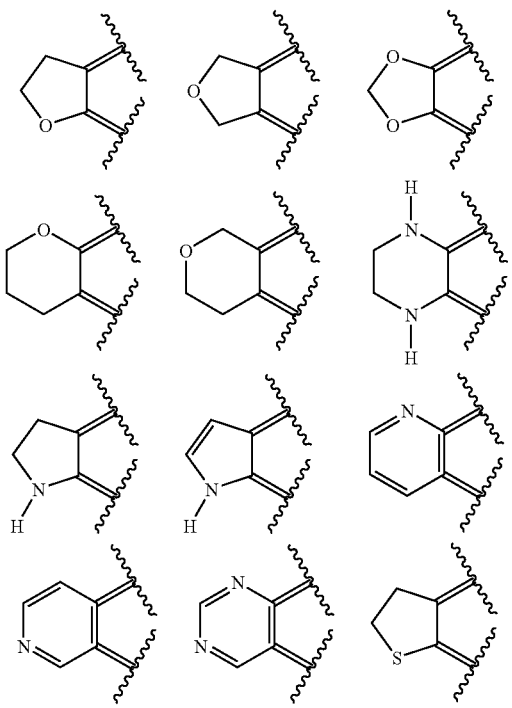
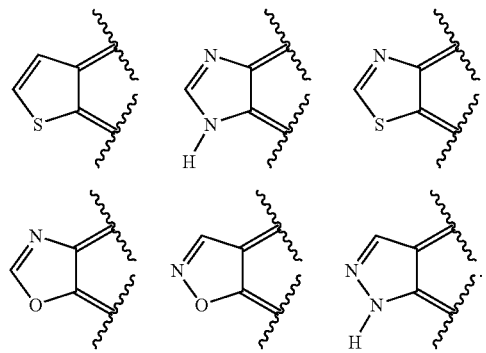

-continued

The A-ring may be an optionally substituted, fused saturated or partially unsaturated 5 or 6 membered carbocyclic ring, such as cyclopentyl, cyclopentenyl, cyclohexyl, cyclohexenyl, and substituted forms thereof, including exemplary structures:

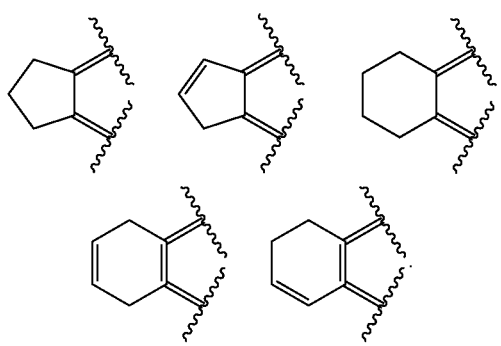

The A-ring may be an optionally substituted ring selected from phenyl. For example, the A-ring may be:

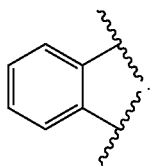

and substituted forms thereof.

Exemplary embodiments of X include 2-pyridyl, 3-pyridyl, 4-pyridyl, 2-imidazolyl, 4-imidazolyl, 3-pyrazolyl, 4-pyrazolyl, 2-thiazolyl, 4-thiazolyl, 5-thiazolyl, 3-pyridazinyl, 4-pyrimidinyl, 5-pyrimidinyl, 2-pyrimidinyl, 5-pyrimidinyl, 6-pyrimidinyl, 2-pyrazinyl, 2-oxazolyl, 4-oxazolyl, 5-oxazolyl, and substituted forms thereof, and shown as:

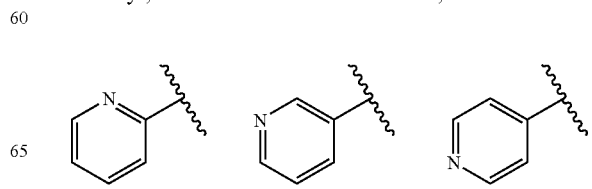

-continued
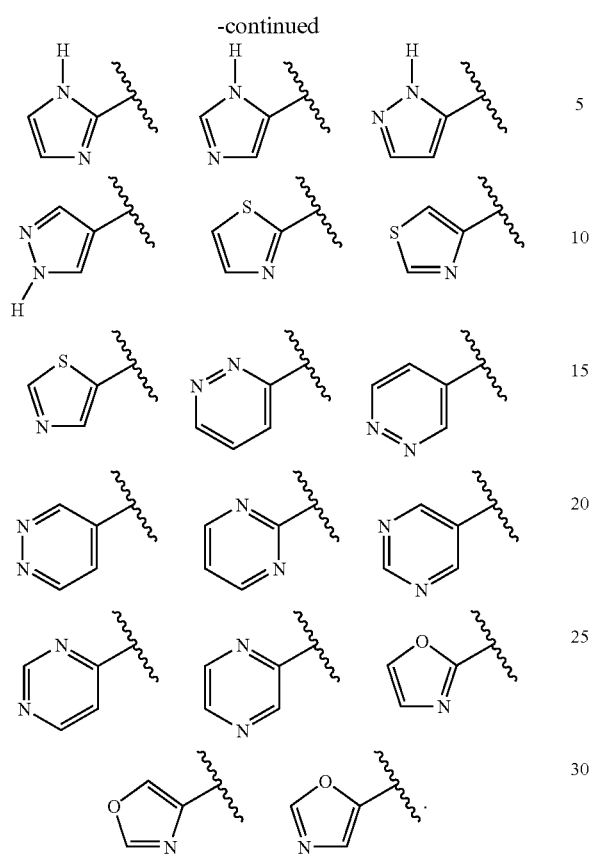
Exemplary embodiments of 5-7 membered ring lactams, 5-7 membered ring lactones, and 5-7 membered ring sultams include the structures:
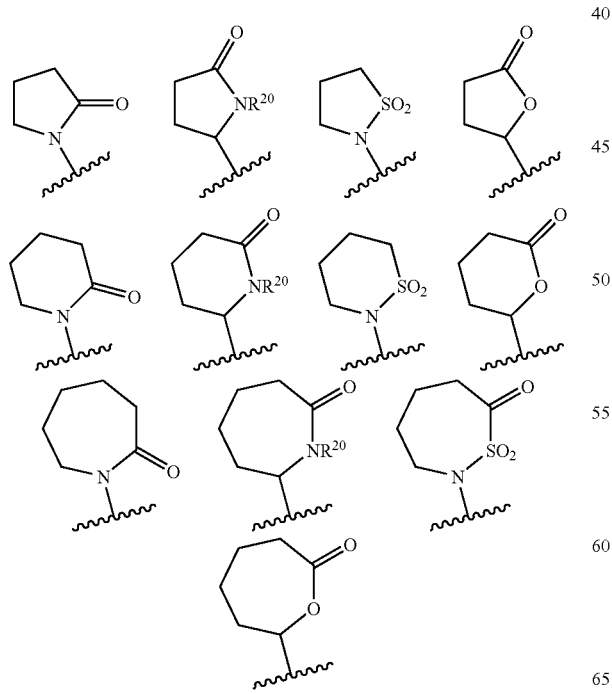
Exemplary embodiments of Formulas Ia and Ib compounds include compounds of Formulas IIa-h and IIIa-f:
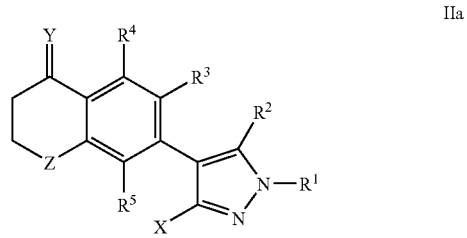
IIa
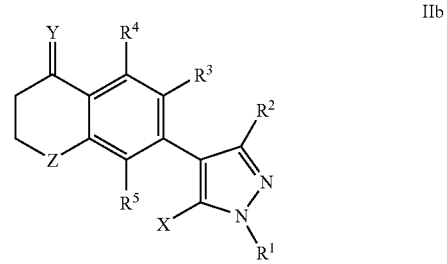
IIb
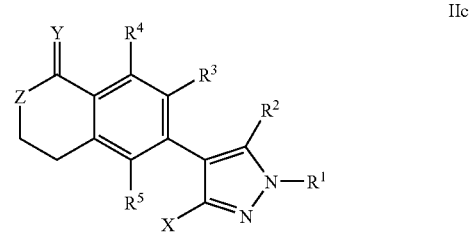
IIc
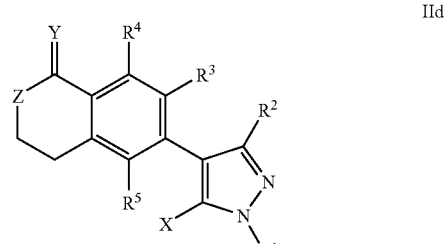
IId
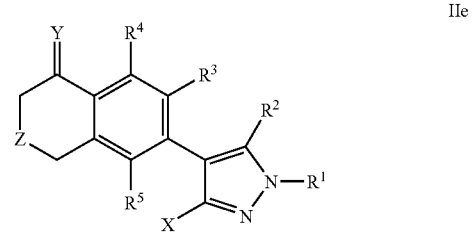
IIe
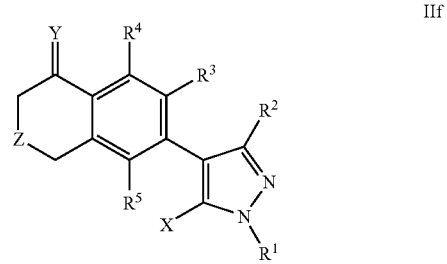
IIf -continued
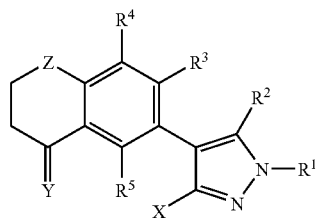
IIg
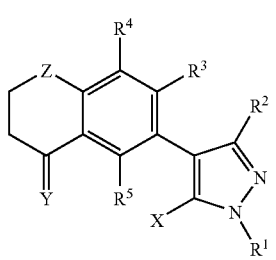
IIh
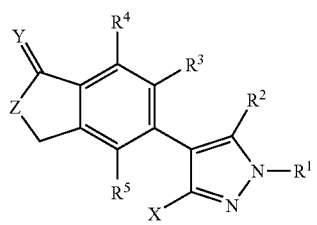
IIIa
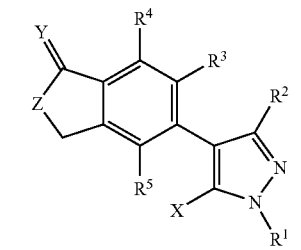
IIIb
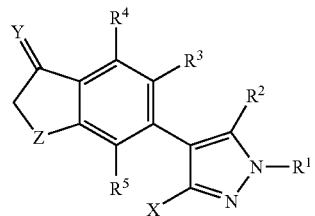
IIIc
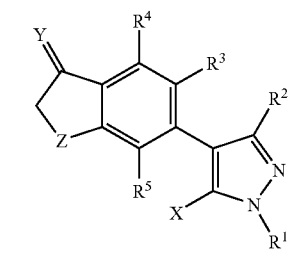
IIId
-continued
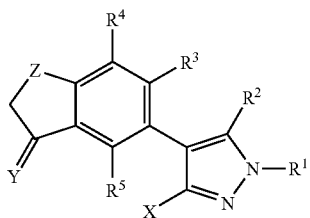
IIIe
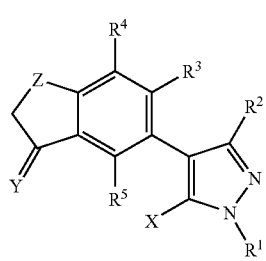
IIIf
wherein Z is selected from $CR^{20}R^{21}$, $C(=Y)$, $NR^{20}$, O, and S.
Exemplary embodiments of Formulas Ia and Ib compounds also include compounds of Formulas IVa, IVb, Va and Vb:
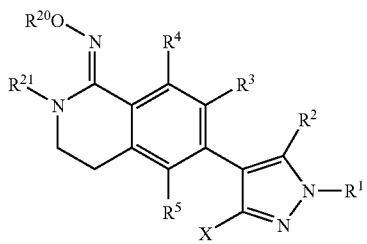
IVa
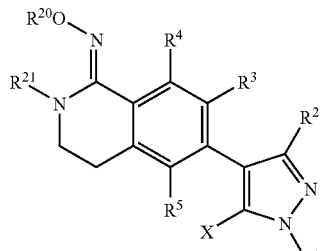
IVb
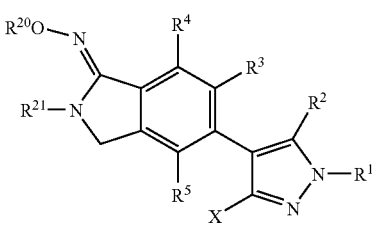
Va -continued

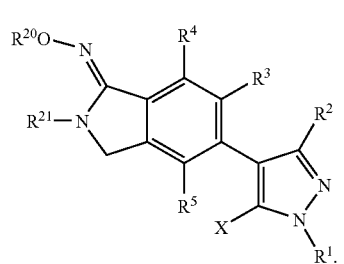

Vb

Exemplary embodiments of Formulas Ia and Ib compounds also include compounds of Formulas VIa, VIb, VIIa and VIIb:

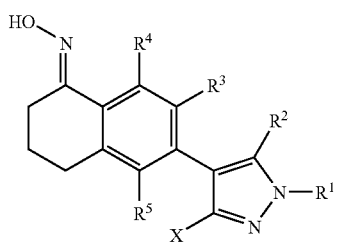

VIa

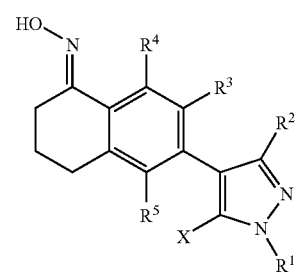

VIb

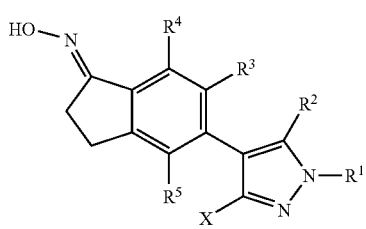

VIIa

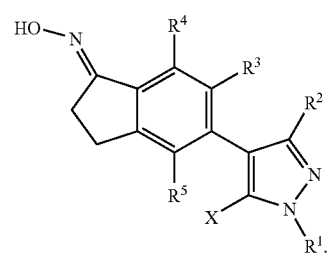

VIIb

Exemplary embodiments of Formulas Ia and Ib compounds also include Formulas VIIIa, VIIIb, IXa and IXb:

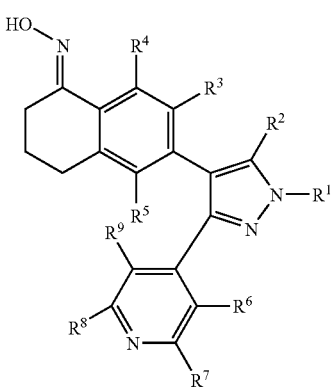

VIIIa

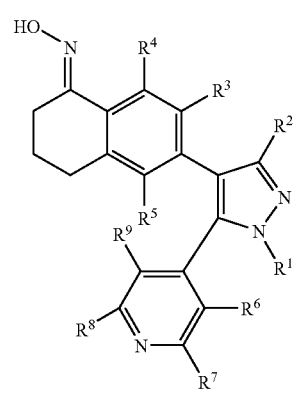

VIIIb

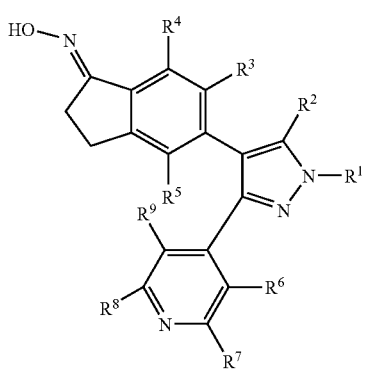

IXa

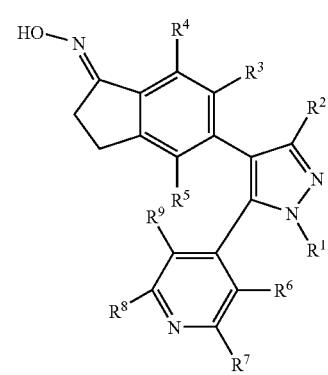

IXb wherein $R^6$, $R^7$, $R^8$, and $R^9$ are independently selected from H, F, Cl, Br, I, —$OR^{20}$, —$C(=Y)R^{20}$, —$C(=Y)OR^{20}$, —$C(=Y)NR^{20}R^{21}$, —$NR^{20}R^{21}$, —$NR^{20}C(=Y)R^{21}$, —$NR^{20}C(=Y)OR^{21}$, —$NR^{23}C(=Y)NR^{20}R^{21}$, —$OC(=Y)R^{20}$, —$OC(=Y)OR^{20}$, —$OC(=Y)NR^{20}R^{21}$, —$OS(O)_2$ (OR²⁰), —OP(=Y)(OR²⁰)(OR²¹), —OP(OR²⁰)(OR²¹), —P(=Y)(OR²⁰)(OR²¹), —P(=Y)(OR²³)NR²⁰R²¹, —SR²⁰, —S(O)R²⁰, —S(O)₂R²¹, —S(O)₂NR²⁰R²¹, —S(O)(OR²⁰), —S(O)₂(OR²⁰), —SC(=Y)R²⁰, —SC(=Y)OR²⁰, —SC(=Y)NR²⁰R²¹, 5-7 membered ring lactam, 5-7 membered ring lactone, 5-7 membered ring sultam, C₁-C₈ alkyl, C₂-C₈ alkenyl, C₂-C₈ alkynyl, C₃-C₁₂ carbocyclyl, C₆-C₂₀ aryl, and C₂-C₂₀ heterocyclyl, wherein said alkyl, alkenyl, alkynyl, carbocyclyl, aryl, and heterocycle are optionally substituted with one or more groups independently selected from F, Cl, Br, I, OR²⁰, NR²⁰R²¹—SR²⁰, —S(O)R²⁰, —S(O)₂ R²⁰, alkyl, alkenyl, alkynyl, carbocyclyl, aryl, and heterocyclyl.

Exemplary embodiments of Formulas Ia and Ib compounds also include compounds of Formulas Xa, Xb, XIa and XIb:

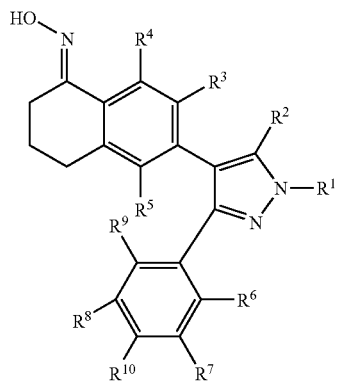

Xa

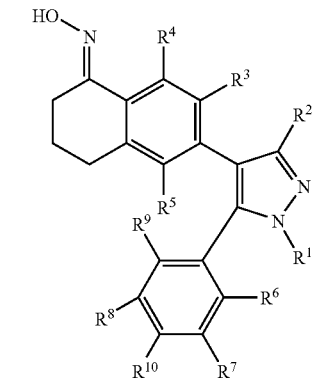

Xb

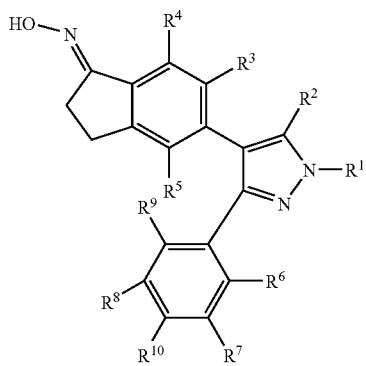

XIa

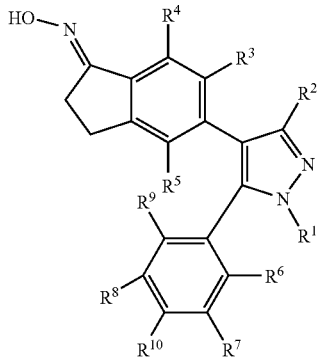

XIb wherein R⁶, R⁷, R⁸, R⁹, and R¹⁰ are independently selected from H, F, Cl, Br, I, —OR²⁰, —C(=Y)R²⁰, —C(=Y)OR²⁰, —C(=Y)NR²⁰R²¹, —NR²⁰R²¹, —NR²⁰C(=Y)R²¹, —NR²⁰C(=Y)OR²¹, —NR²³C(=Y)NR²⁰R²¹, —OC(=Y)R²⁰, —OC(=Y)OR²⁰, —OC(=Y)NR²⁰R²¹, —OS(O)₂(OR²⁰), —OP(=Y)(OR²⁰)(OR²¹), —OP(OR²⁰)(OR²¹), —P(=Y)(OR²⁰)(OR²¹), —P(=Y)(OR²³)NR²⁰R²¹, —SR²⁰, —S(O)R²⁰, —S(O)₂R²⁰, —S(O)₂NR²⁰R²¹, —S(O)(OR²⁰), —S(O)₂(OR²⁰), —SC(=Y)R²⁰, —SC(=Y)OR²⁰, —SC(=Y)NR²⁰R²¹, 5-7 membered ring lactam, 5-7 membered ring lactone, 5-7 membered ring sultam, C₁-C₈ alkyl, C₂-C₈ alkenyl, C₂-C₈ alkynyl, C₃-C₁₂ carbocyclyl, C₆-C₂₀ aryl, and C₂-C₂₀ heterocyclyl, wherein said alkyl, alkenyl, alkynyl, carbocyclyl, aryl, and heterocyclyl are optionally substituted with one or more groups independently selected from F, Cl, Br, I, OR²⁰, NR²⁰R²¹ —SR²⁰, —S(O)R²⁰, —S(O)₂ R²⁰, alkyl, alkenyl, alkynyl, carbocyclyl, aryl, and heterocyclyl.

Exemplary embodiments of Formulas Ia and Ib compounds also include Formulas XIIa-d and XIIa-j:

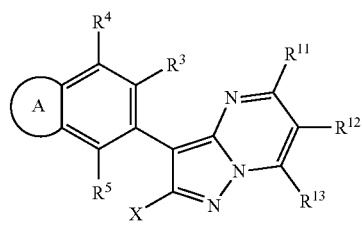

XIIa

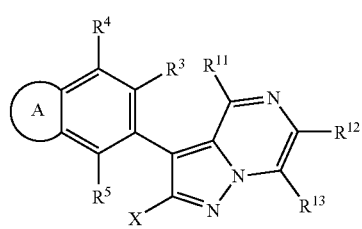

XIIb

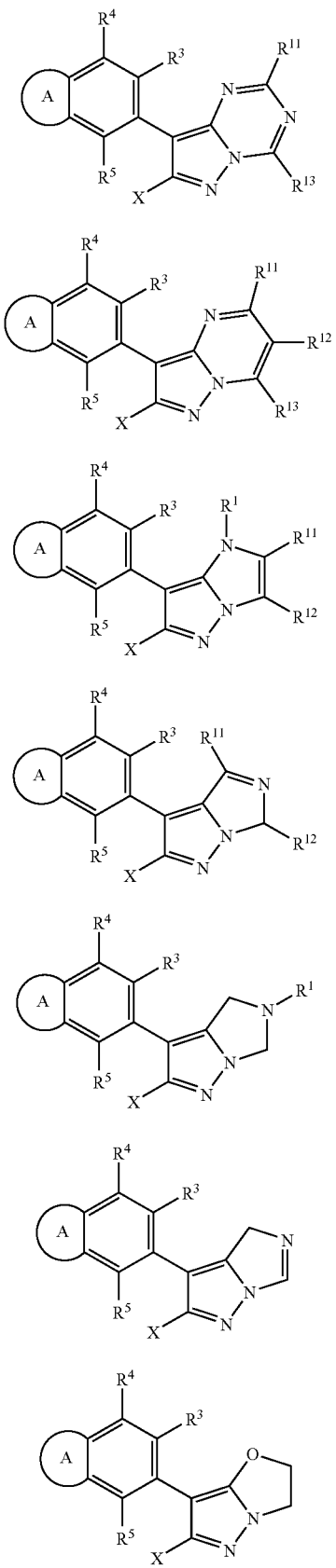
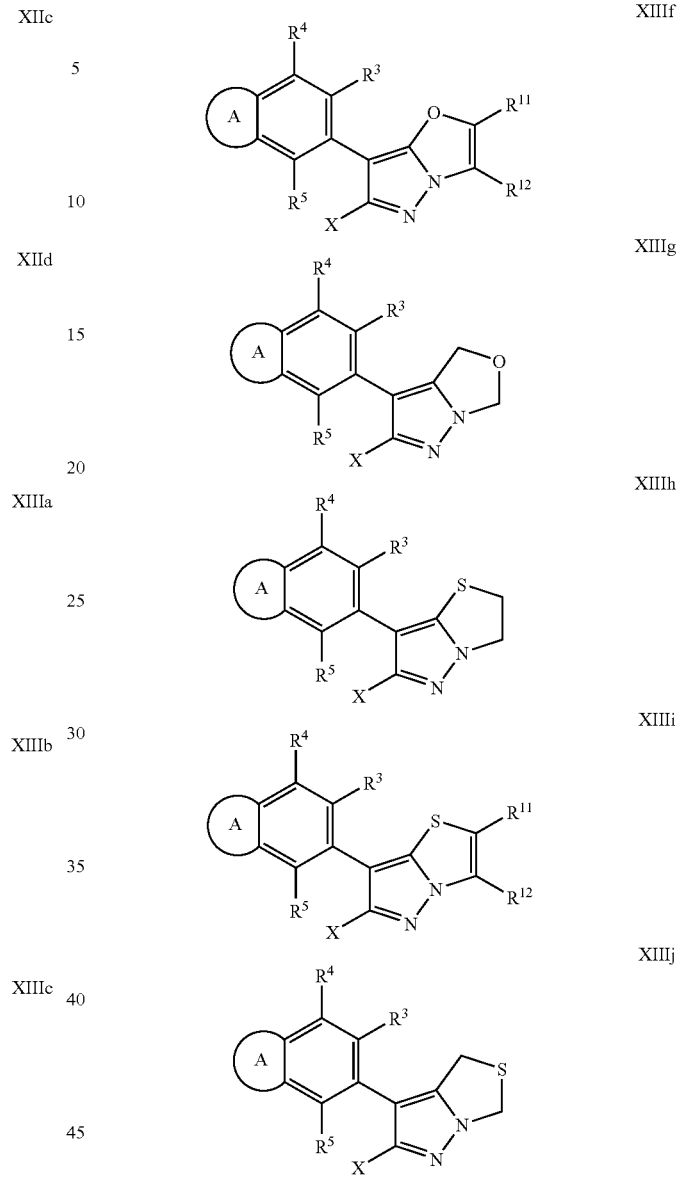

wherein $R^{11}$, $R^{12}$, and $R^{13}$ are independently selected from H, F, Cl, Br, I, —OR$^{20}$, —C(=Y)R$^{20}$, —C(=Y)OR$^{20}$, —C(=Y)NR$^{20}$R$^{21}$, —NR$^{20}$R$^{21}$, —NR$^{20}$C(=Y)R$^{21}$, —NR$^{20}$C(=Y)OR$^{21}$, —NR$^{23}$C(=Y)NR$^{20}$R$^{21}$, —OC(=Y)R$^{20}$, —OC(=Y)OR$^{20}$, —OC(=Y)NR$^{20}$R$^{21}$, —OS(O)$_2$(OR$^{20}$), —OP(=Y)(OR$^{20}$)(OR$^{21}$), —OP(OR$^{20}$)(OR$^{21}$), —P(=Y)(OR$^{20}$)(OR$^{21}$), —P(=Y)(OR$^{23}$)NR$^{20}$R$^{21}$, —SR$^{20}$, —S(O)R$^{20}$, —S(O)$_2$R$^{20}$, —S(O)$_2$NR$^{20}$R$^{21}$, —S(O)(OR$^{20}$), —S(O)$_2$(OR$^{20}$), —SC(=Y)R$^{20}$, —SC(=Y)OR$^{20}$, —SC(=Y)NR$^{20}$R$^{21}$, 5-7 membered ring lactam, 5-7-membered ring lactone, 5-7 membered ring sultam, $C_1$-$C_8$ alkyl, $C_2$-$C_8$ alkenyl, $C_2$-$C_8$ alkynyl, $C_3$-$C_{12}$ carbocyclyl, $C_6$-$C_{20}$ aryl, and $C_2$-$C_{20}$ heterocycle, wherein said alkyl, alkenyl, alkynyl, carbocyclyl, aryl, and heterocyclyl are optionally substituted with one or more groups independently selected from F, Cl, Br, I, OR$^{20}$, NR$^{20}$R$^{21}$ —SR$^{20}$, —S(O)R$^{20}$, —S(O)$_2$ R$^{20}$, alkyl, alkenyl, alkynyl, carbocyclyl, aryl, and heterocyclyl.

Exemplary embodiments of Formulas Ia and Ib compounds also include Formulas XIVa-d:
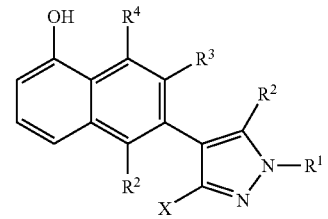
XIVa
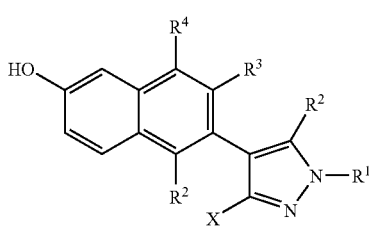
XIVb
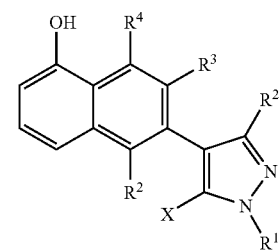
XIVc
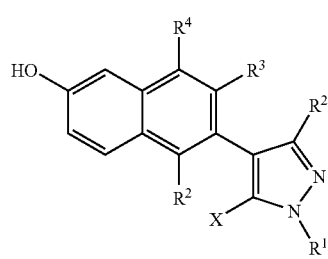
XIVd
Exemplary embodiments of Formulas Ia and Ib compounds also include Formulas XVa-d:
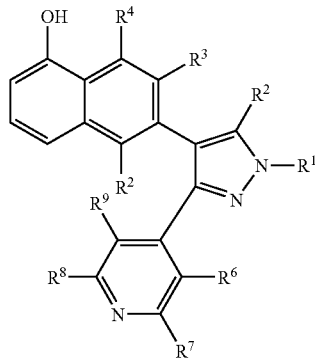
XVa
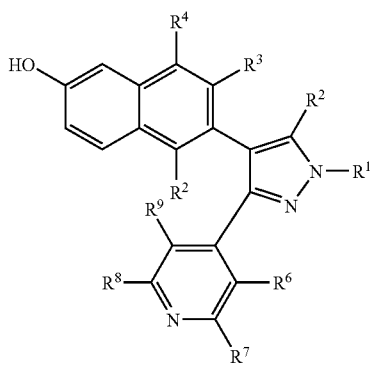
XVb
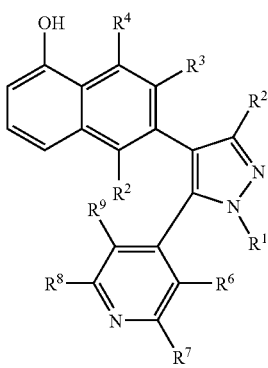
XVc
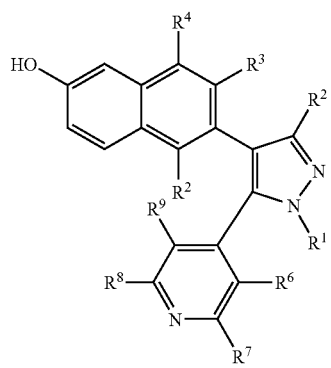
XVd
Compounds 101-160 listed in Table 1 were prepared, characterized, and assayed for B-Raf binding activity and in vitro activity against tumor cells.

TABLE 1

| No. | Structure | Name |
| --- | --- | --- |
| 101 | 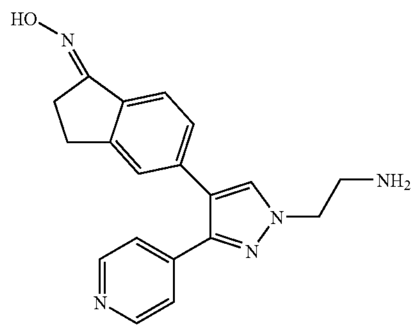 | 5-(1-(2-aminoethyl)-3-pyridin-4-yl-1H-pyrazol-4-yl)-2,3-dihydroinden-1-one oxime |
| 102 | 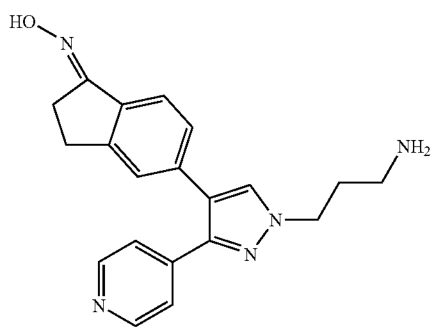 | 5-(1-(3-aminopropyl)-3-pyridin-4-yl-1H-pyrazol-4-yl)-2,3-dihydroinden-1-one oxime |
| 103 | 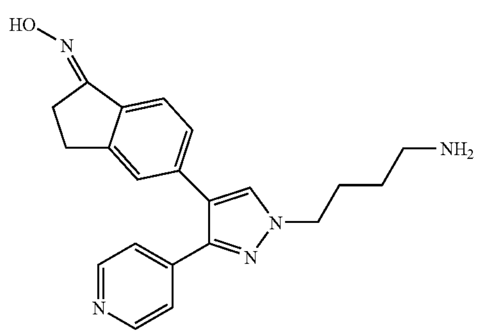 | 5-(1-(4-aminobutyl)-3-pyridin-4-yl-1H-pyrazol-4-yl)-2,3-dihydroinden-1-one oxime |
| 104 | 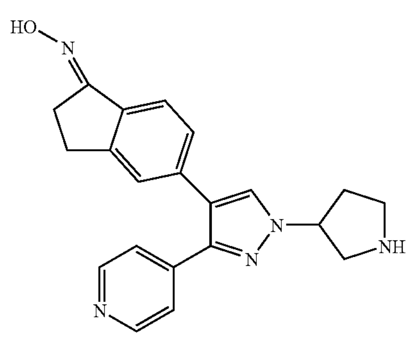 | 5-(1-(pyrrolidin-3-yl)-3-pyridin-4-yl-1H-pyrazol-4-yl)-2,3-dihydroinden-1-one oxime |

TABLE 1-continued

| No. | Structure | Name |
| --- | --- | --- |
| 105 | 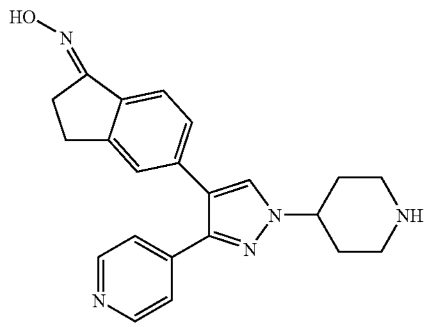 | 5-(1-(piperidin-4-yl)-3-pyridin-4-yl-1H-pyrazol-4-yl)-2,3-dihydroinden-1-one oxime |
| 106 | 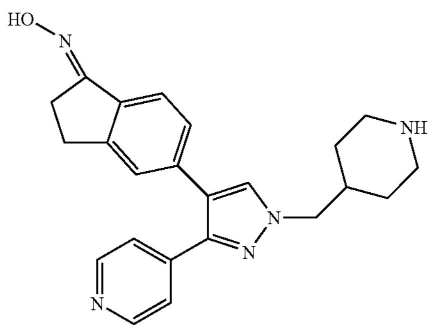 | 5-(1-(4-methylpiperidinyl)-3-pyridin-4-yl-1H-pyrazol-4-yl)-2,3-dihydroinden-1-one oxime |
| 107 | 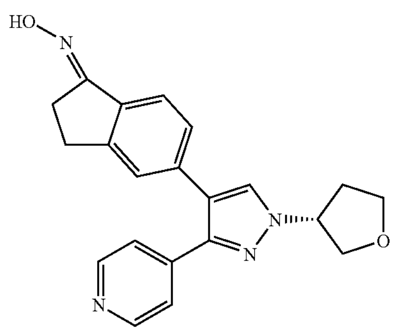 | 5-(1-(3R-tetrahydrofuranyl)-3-pyridin-4-yl-1H-pyrazol-4-yl)-2,3-dihydroinden-1-one oxime |
| 108 | 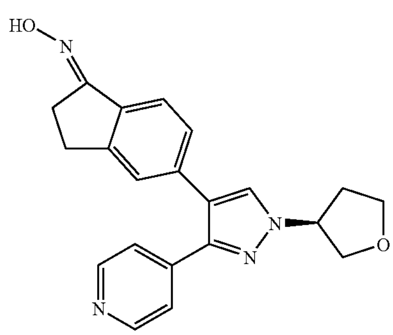 | 5-(1-(3S-tetrahydrofuranyl)-3-pyridin-4-yl-1H-pyrazol-4-yl)-2,3-dihydroinden-1-one oxime |

TABLE 1-continued

| No. | Structure | Name |
|---|---|---|
| 109 | 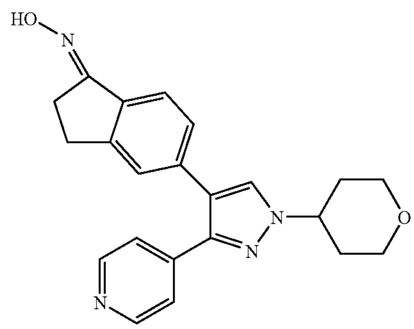 | 5-(1-(4-tetrahydropyranyl)-3-pyridin-4-yl-1H-pyrazol-4-yl)-2,3-dihydroinden-1-one oxime |
| 110 | 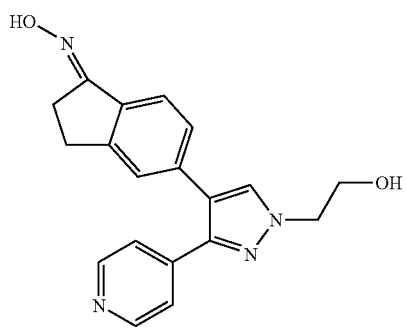 | 5-(1-(2-hydroxyethyl)-3-pyridin-4-yl-1H-pyrazol-4-yl)-2,3-dihydroinden-1-one oxime |
| 111 | 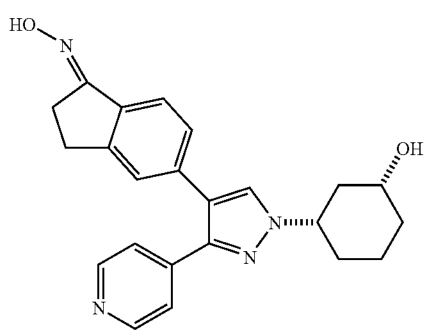 | 5-(1-(3S-(1R-hydroxy)cyclohexyl)-3-pyridin-4-yl-1H-pyrazol-4-yl)-2,3-dihydroinden-1-one oxime |
| 112 | 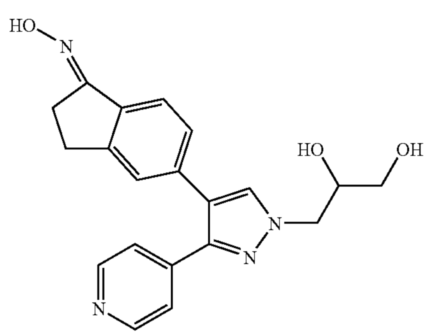 | 5-(1-(2,3 dihydroxypropyl)-3-pyridin-4-yl-1H-pyrazol-4-yl)-2,3-dihydroinden-1-one oxime |

TABLE 1-continued

| No. | Structure | Name |
| --- | --- | --- |
| 113 | 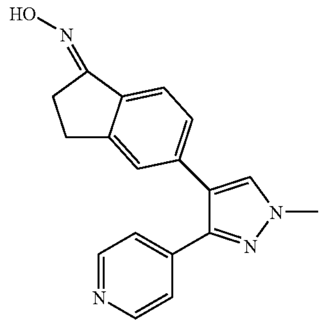 | 5-(1-methyl-3-pyridin-4-yl-1H-pyrazol-4-yl)-2,3-dihydroinden-1-one oxime |
| 114 | 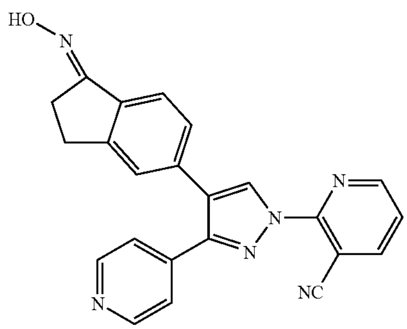 | 5-(1-(3-cyano-pyridin-2-yl)-3-pyridin-4-yl-1H-pyrazol-4-yl)-2,3-dihydroinden-1-one oxime |
| 115 | 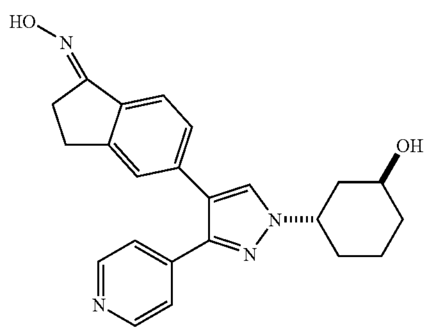 | 5-(1-(3S-(1S-hydroxy)cyclohexyl)-3-pyridin-4-yl-1H-pyrazol-4-yl)-2,3-dihydroinden-1-one oxime |
| 116 | 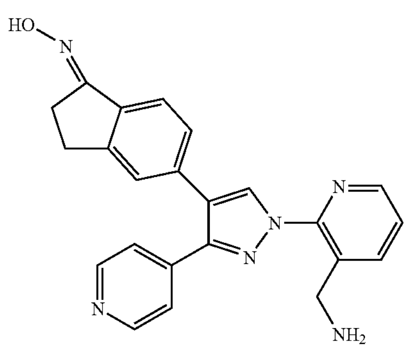 | 5-(1-(3-aminomethyl-pyridin-2-yl)-3-pyridin-4-yl-1H-pyrazol-4-yl)-2,3-dihydroinden-1-one oxime |

TABLE 1-continued

| No. | Structure | Name |
|---|---|---|
| 117 | 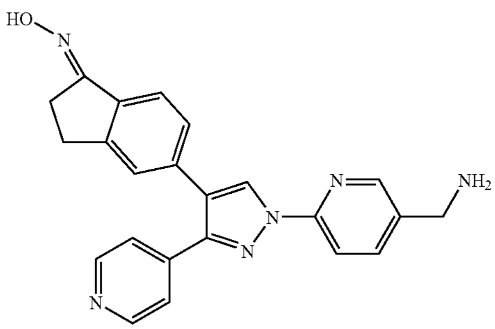 | 5-(1-(5-(aminomethyl)pyridin-2-yl)-3-pyridin-4-yl-1H-pyrazol-4-yl)-2,3-dihydroinden-1-one oxime |
| 118 | 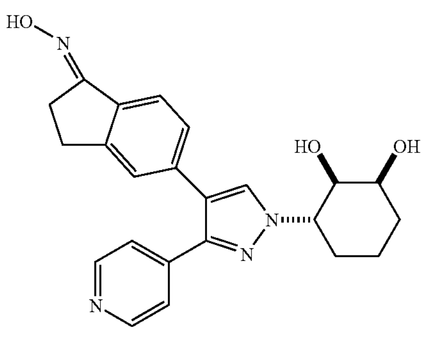 | 5-(1-(3S-(1S,2R-dihydroxy)cyclohexyl)-3-pyridin-4-yl-1H-pyrazol-4-yl)-2,3-dihydroinden-1-one oxime |
| 119 | 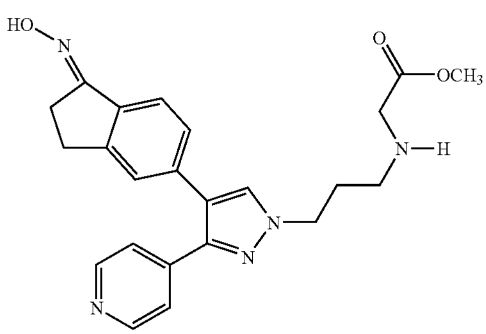 | 5-(1-(3-methoxyacetamidopropyl)-3-pyridin-4-yl-1H-pyrazol-4-yl)-2,3-dihydroinden-1-one oxime |
| 120 | 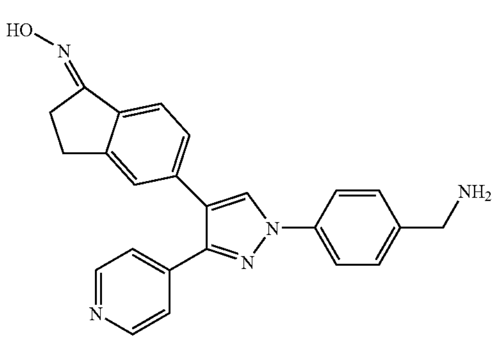 | 5-(1-(4-aminomethylphenyl)-3-pyridin-4-yl-1H-pyrazol-4-yl)-2,3-dihydroinden-1-one oxime |

TABLE 1-continued

| No. | Structure | Name |
|---|---|---|
| 121 | 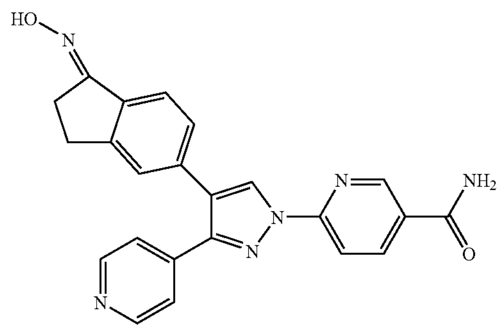 | 5-(1-(5-(acetamido)pyridin-2-yl)-3-pyridin-4-yl-1H-pyrazol-4-yl)-2,3-dihydroinden-1-one oxime |
| 122 | 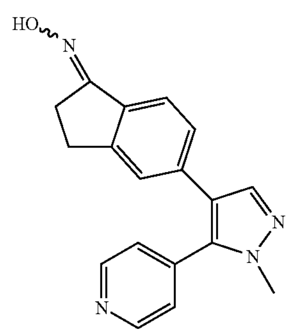 | 5-(1-Methyl-5-pyridin-4-yl-1H-pyrazol-4-yl)-2,3-dihydroinden-1-one oxime |
| 123 | 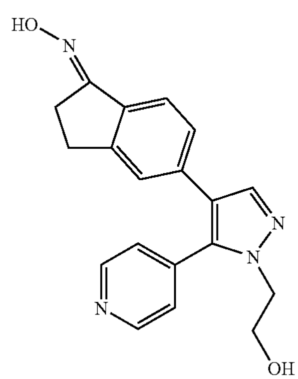 | 5-(1-(2-hydroxyethyl)-5-pyridin-4-yl-1H-pyrazol-4-yl)-2,3-dihydroinden-1-one oxime |
| 124 | 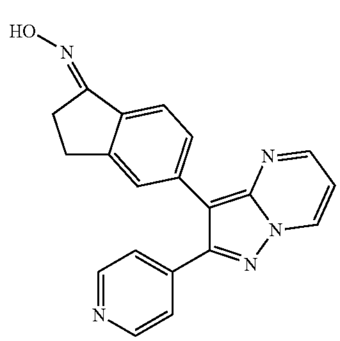 | 5-(2-(pyridin-4-yl)pyrazolo[1.5-a]pyrimidin-3-yl)-2,3-dihydroinden-1-one oxime |

TABLE 1-continued

| No. | Structure | Name |
|---|---|---|
| 125 | 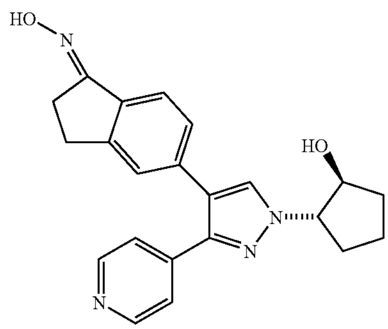 | 5-(1-(2S-(1S-hydroxy)cyclopentyl)-3-pyridin-4-yl-1H-pyrazol-4-yl)-2,3-dihydroinden-1-one oxime |
| 126 | 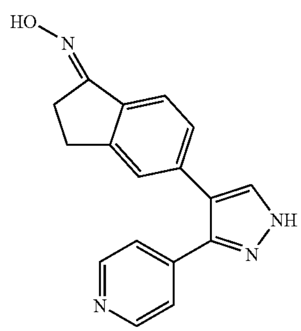 | 5-(3-pyridin-4-yl-1H-pyrazol-4-yl)-2,3-dihydroinden-1-one oxime |
| 127 | 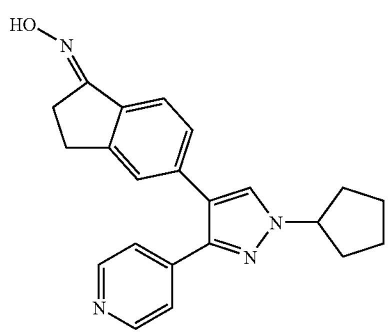 | 5-(1-cyclopentyl-3-pyridin-4-yl-1H-pyrazol-4-yl)-2,3-dihydroinden-1-one oxime |
| 128 | 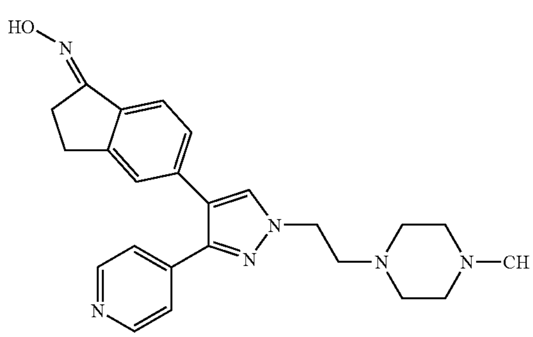 | 5-(1-(2-(4-methylpiperazinyl)ethyl)-3-pyridin-4-yl-1H-pyrazol-4-yl)-2,3-dihydroinden-1-one oxime |

TABLE 1-continued

| No. | Structure | Name |
|---|---|---|
| 129 | 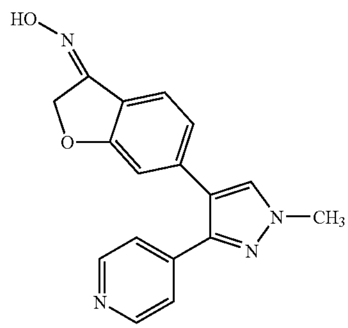 | 5-(1-methyl-3-pyridin-4-yl-1H-pyrazol-4-yl)-benzofuran-3(2H)-one oxime |
| 130 | 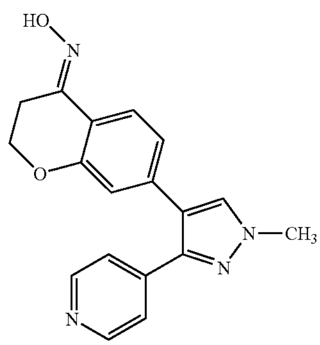 | 5-(1-methyl-3-pyridin-4-yl-1H-pyrazol-4-yl)-2,3-dihydrochromen-4-one oxime |
| 131 | 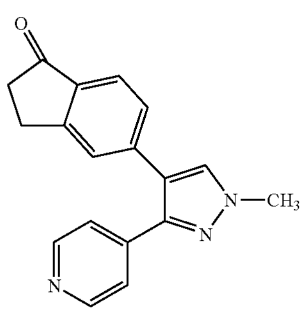 | 5-(1-methyl-3-pyridin-4-yl-1H-pyrazol-4-yl)-2,3-dihydroinden-1-one |
| 132 | 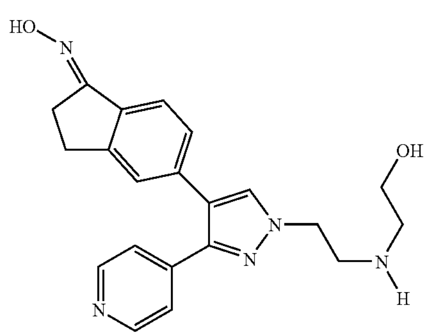 | 5-(1-(2-(2-hydroxyethyl)aminoethyl)-3-pyridin-4-yl-1H-pyrazol-4-yl)-2,3-dihydroinden-1-one oxime |

TABLE 1-continued

| No. | Structure | Name |
|---|---|---|
| 133 | 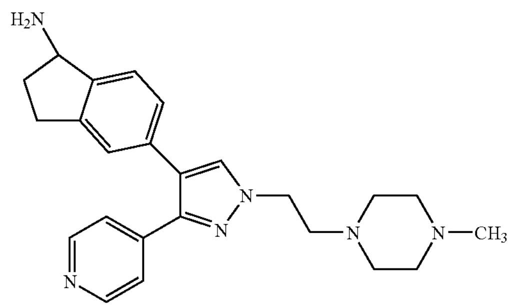 | 5-(1-(2-(4-methylpiperazinyl)ethyl)-3-pyridin-4-yl-1H-pyrazol-4-yl)-2,3-dihydro-1H-inden-1-amine |
| 134 | 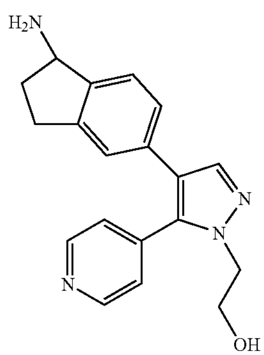 | 5-(2-hydroxyethyl-5-pyridin-4-yl-1H-pyrazol-4-yl)-2,3-dihydro-1H-inden-1-amine |
| 135 | 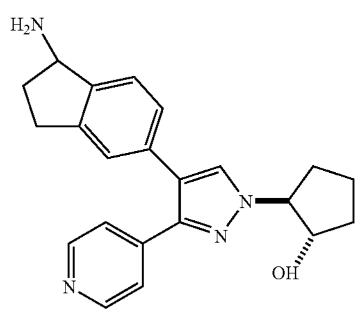 | 5-(1-(2S-(1S-hydroxy)cyclopentyl)-3-pyridin-4-yl-1H-pyrazol-4-yl)-2,3-dihydro-1H-inden-1-amine |
| 136 | 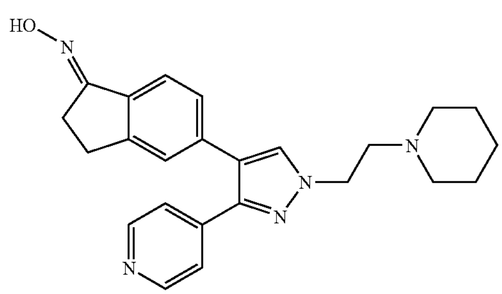 | 5-(1-(2-(N-piperidyl)ethyl)-3-pyridin-4-yl-1H-pyrazol-4-yl)-2,3-dihydroinden-1-one oxime |

TABLE 1-continued

| No. | Structure | Name |
|---|---|---|
| 137 | 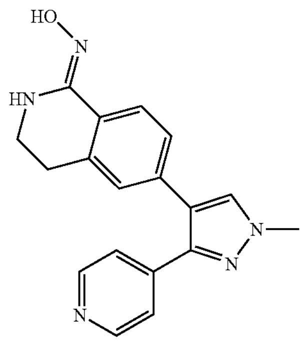 | 5-(1-methyl-3-pyridin-4-yl-1H-pyrazol-4-yl)-3,4-dihydroisoquinolin-1(2H)-one oxime |
| 138 | 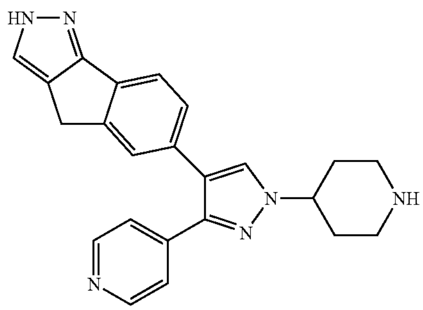 | 5-(1-(4-piperidyl)-3-pyridin-4-yl-1H-pyrazol-4-yl)-2,4,5,6-tetrahydrocyclopenta[c]phenyl pyrazole |
| 139 | 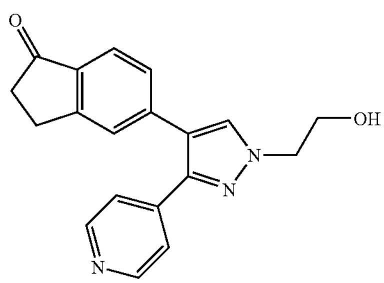 | 5-(1-(2-hydroxyethyl)-3-pyridin-4-yl-1H-pyrazol-4-yl)-2,3-dihydroinden-1-one |
| 140 | 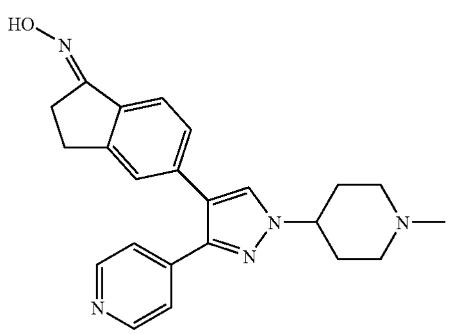 | 5-(1-(4-(N-methylpiperidyl))-3-pyridin-4-yl-1H-pyrazol-4-yl)-2,3-dihydroinden-1-one oxime |
| 141 | 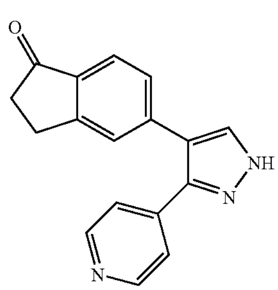 | 5-(3-pyridin-4-yl-1H-pyrazol-4-yl)-2,3-dihydroinden-1-one |

TABLE 1-continued

| No. | Structure | Name |
| --- | --- | --- |
| 142 | 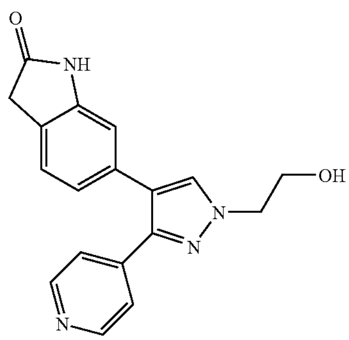 | 5-(1-(2-hydroxyethyl)-3-pyridin-4-yl-1H-pyrazol-4-yl)-indolin-2-one |
| 143 | 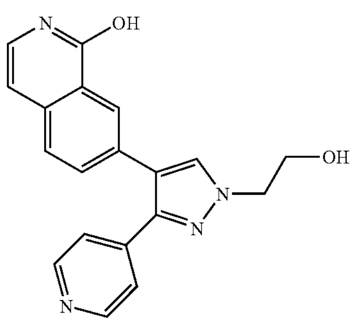 | 5-(1-(2-hydroxyethyl)-3-pyridin-4-yl-1H-pyrazol-4-yl)-isoquinolin-1-ol |
| 144 | 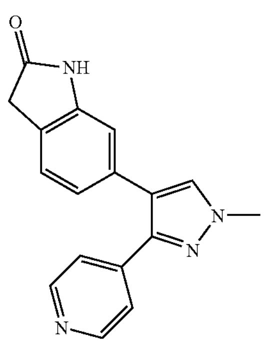 | 5-(1-methyl-3-pyridin-4-yl-1H-pyrazol-4-yl)-indolin-2-one |
| 145 | 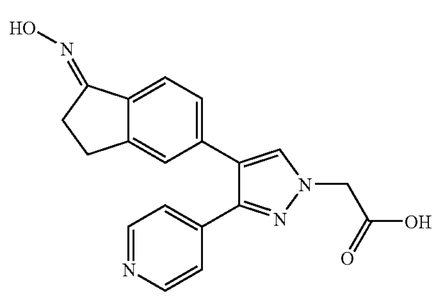 | 5-(1-acetic acid-3-pyridin-4-yl-1H-pyrazol-4-yl)-2,3-dihydroinden-1-one oxime |

TABLE 1-continued

| No. | Structure | Name |
|---|---|---|
| 146 | 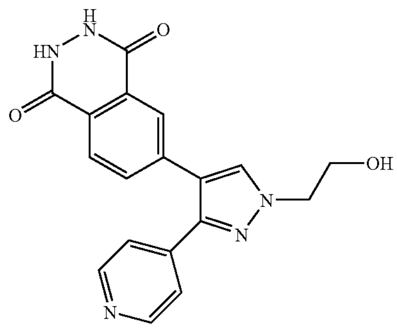 | 5-(1-(2-hydroxyethyl)-3-pyridin-4-yl-1H-pyrazol-4-yl)-2,3-dihydrophthalazine-1,4-dione |
| 147 | 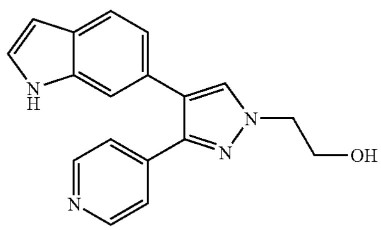 | 5-(1-(2-hydroxyethyl)-3-pyridin-4-yl-1H-pyrazol-4-yl)-6-1H-indole |
| 148 | 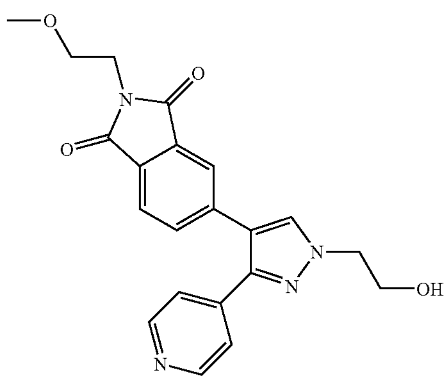 | 5-(1-(2-hydroxyethyl)-3-pyridin-4-yl-1H-pyrazol-4-yl)-2-(2-methoxyethyl)isoindoline-1,3-dione |
| 149 | 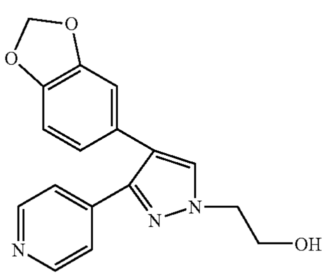 | 5-(1-(2-hydroxyethyl)-3-pyridin-4-yl-1H-pyrazol-4-yl)-benzo[d][1,3]dioxole |
| 150 | 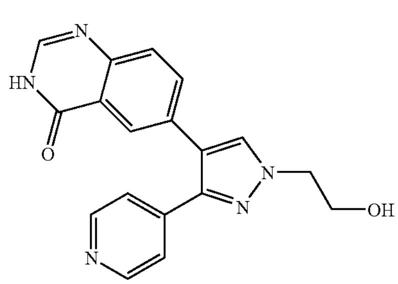 | 5-(1-(2-hydroxyethyl)-3-pyridin-4-yl-1H-pyrazol-4-yl)-quinazolin-4(3H)-one |

TABLE 1-continued

| No. | Structure | Name |
|---|---|---|
| 151 | 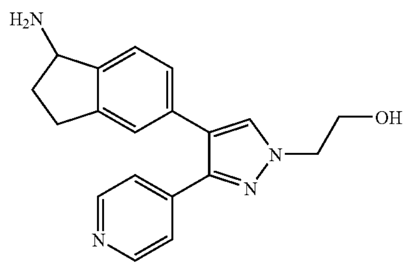 | 5-(1-(2-hydroxyethyl)-3-pyridin-4-yl-1H-pyrazol-4-yl)-2,3-dihydro-1H-inden-1-amine |
| 152 | 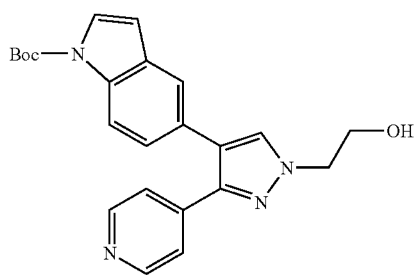 | 5-(1-(2-hydroxyethyl)-3-pyridin-4-yl-1H-pyrazol-4-yl)-N-tert-butyloxycarbonyl-2,3-dihydro-1H-inden-1-amine |
| 153 | 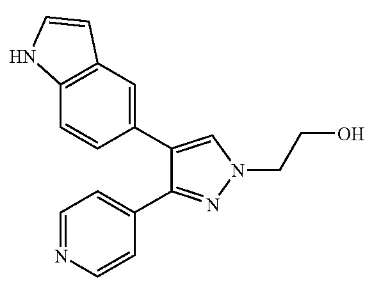 | 5-(1-(2-hydroxyethyl)-3-pyridin-4-yl-1H-pyrazol-4-yl)-5-1H-indole |
| 154 | 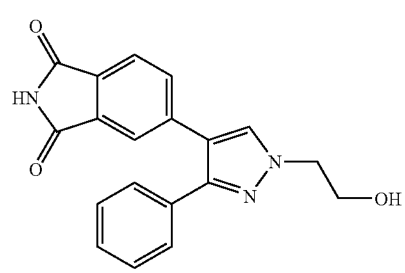 | 5-(1-(2-hydroxyethyl)-3-pyridin-4-yl-1H-pyrazol-4-yl)-5-isoindoline-1,3-dione |
| 155 | 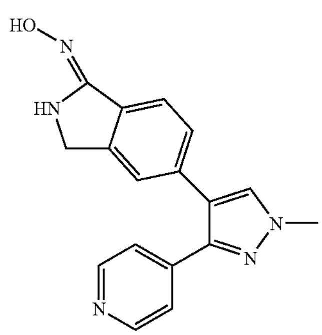 | (Z)-5-(1-methyl-3-(pyridin-4-yl)-1H-pyrazol-4-yl)isoindolin-1-one oxime |

TABLE 1-continued

| No. | Structure | Name |
|---|---|---|
| 156 | 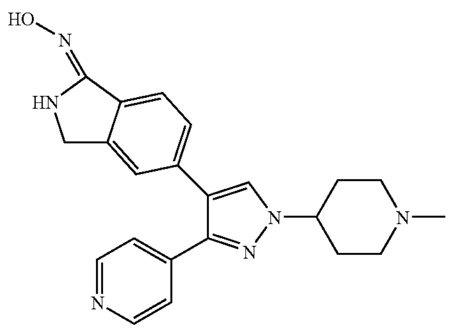 | (Z)-5-(1-(1-methylpiperidin-4-yl)-3-(pyridin-4-yl)-1H-pyrazol-4-yl)isoindolin-1-one oxime |
| 157 | 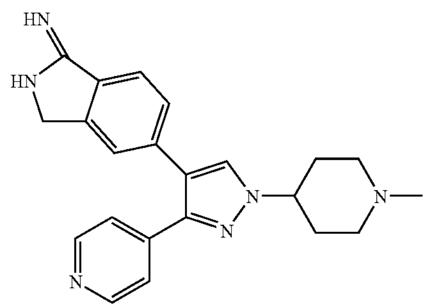 | 5-(1-(1-methylpiperidin-4-yl)-3-(pyridin-4-yl)-1H-pyrazol-4-yl)isoindolin-1-imine |
| 158 | 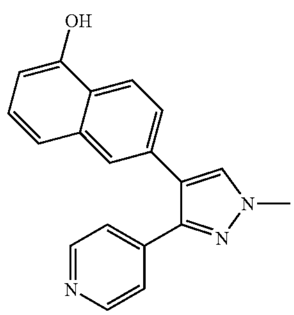 | 6-(1-methyl-3-(pyridin-4-yl)-1H-pyrazol-4-yl)naphthalen-1-ol |
| 159 | 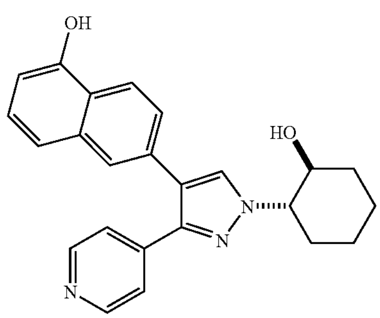 | 6-(1-((1S,2S)-2-hydroxycyclohexyl)-3-(pyridin-4-yl)-1H-pyrazol-4-yl)naphthalen-1-ol |
| 160 | 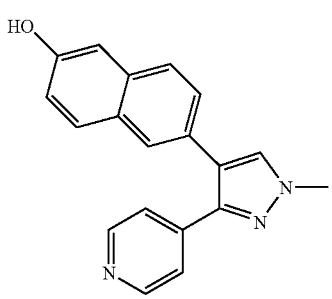 | 6-(1-methyl-3-(pyridin-4-yl)-1H-pyrazol-4-yl)naphthalen-2-ol |

The compounds of the invention may contain asymmetric or chiral centers, and, therefore, exist in different stereoisomeric forms. It is intended that all stereoisomeric forms of the compounds of the invention, including but not limited to: diastereomers, enantiomers, and atropisomers as well as mixtures thereof such as racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention. Both the single positional isomers and mixture of positional isomers, e.g., resulting from the N-oxidation of the pyrimidine and pyrazine rings, or the E and Z forms of oxime moieties, are also within the scope of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

It is also possible that the compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Hydroxyimino or alkoxyimino (oxime) moieties of the compounds of the invention, e.g. Formula I-XIX compounds, can be positioned on any of carbon atoms of ring A. The oxime moiety can exist as either the E or Z isomer, or as a mixture of both.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I, and $^{125}$I, respectively. Certain isotopically-labeled compounds of the present invention (e.g., those labeled with $^3$H and $^{14}$C) are useful in compound and/or substrate tissue distribution assays. Tritiated (i.e., $^3$H) and carbon-14 (i.e., $^{14}$C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Synthesis of Pyrazolyl RAF Inhibitor Compounds

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, N.Y. (1967-1999 ed.), or Beilsteins Handbuch der organischen Chemie, 4, Aufl. ed. Springer-Verlag, Berlin, including supplements (also available via the Beilstein online database)).

Compounds of Formulas Ia and Ib are pyrazolyl compounds (pyrazolo), which may be readily prepared using procedures well-known to prepare other heterocycles, which are described for instance in "Comprehensive Heterocyclic Chemistry, Editors Katrizky and Rees, Pergamon Press, 1984. Methods for pyrazole synthesis are also disclosed in: U.S. Pat. No. 5,008,363; Penning, et al (1997) Bioorganic & Med. Chem. Letters 7(16):2121-2124; Dombroski et al (2004) Bioorganic & Med. Chem. Letters 14:919-923; Almansa et al (2001) J. Med. Chem. 44:350-361; Fray et al (1995) J. Med. Chem. 38:3524-3535).

Compounds of Formulas Ia and Ib may be prepared singly or as compound libraries comprising at least 2, for example 5 to 1,000 compounds, or 10 to 100 compounds of Formulas Ia and Ib. Libraries of compounds of the invention may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds of Formulas Ia and Ib, or pharmaceutically acceptable salts thereof.

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

The following general synthetic schemes can be used to prepare compounds of the present invention, wherein the $R^1$-$R^5$ substituents, the A-ring, and X are as defined for Formulas Ia and Ib.
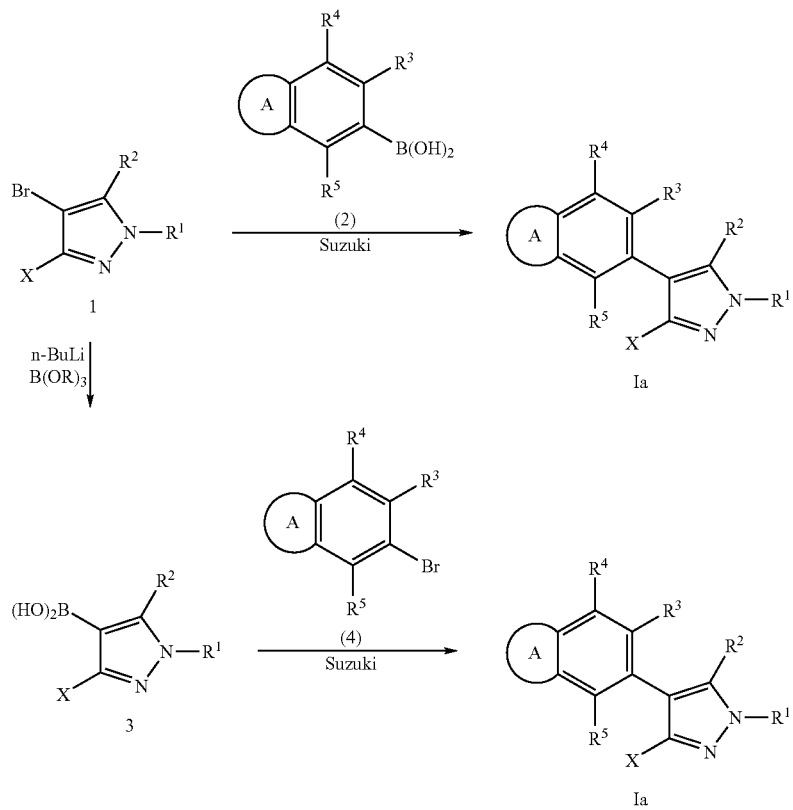
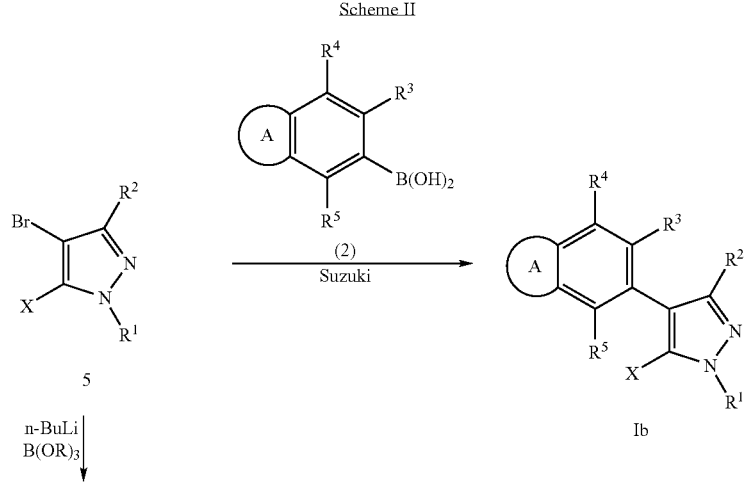

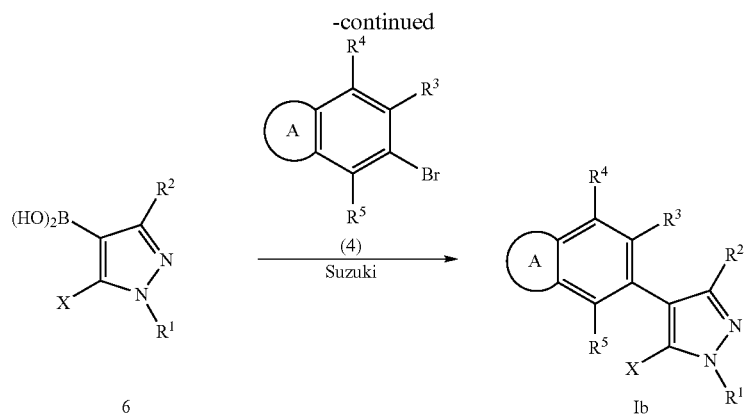

Formation of the pyrazoleboronic acids 3 and 6 is carried out by treating bromopyrazoles 1 or 5 with n-butyllithium in tetrahydrofuran at −78° C., quenching the lithiated pyrazole intermediate with trimethylborate, and isolating the hydrolyzed product by aqueous acidic workup. Coupling of the fused A-ring with the pyrazole can be done via a Suzuki reaction. This is accomplished wither by coupling of the bromopyrazole 1 or 5 with the fused A-ring boronic acid 2, or by coupling the pyrazole boronic acid 3 or 6 with the bromo-substituted fused A-ring 4. The Suzuki reactions are typically conducted in a solvent mixture of acetonitrile and water, sometimes with N,N-dimethylformamide (DMF) as a co-solvent. (For reviews see: Miyaura et al. (1995) Chem. Rev. 95:2457-2483; Suzuki, A. (1999) J. Organomet. Chem. 576: 147-168; Suzuki, A. in Metal-Catalyzed Cross-Coupling Reactions, Diederich, F., Stang, P. J., Eds., VCH, Weinheim, Del. (1998), pp 49-97). The coupling reactions are carried out at an elevated temperature of about 80° C. in the presence of several equivalents of a base, such as potassium carbonate, and a catalytic amount of a source of Pd(0), such as tetrakis (triphenylphosphine)palladium(0). Other catalysts, bases, solvent systems, and temperatures can be successfully employed in the Suzuki reaction (Owens et al (2003) Bioorganic & Med. Chem. Letters 13:4143-4145; Molander et al (2002) Organic Letters 4(11):1867-1870; U.S. Pat. No. 6,448,433). In particular, the catalysts Pd (PPh$_3$)$_4$, Pd(OAc)$_2$, PdCl$_2$(dppf)-DCM, Pd$_2$(dba)$_3$/Pt-Bu)$_3$ may be employed, depending on reaction variables.

Scheme III

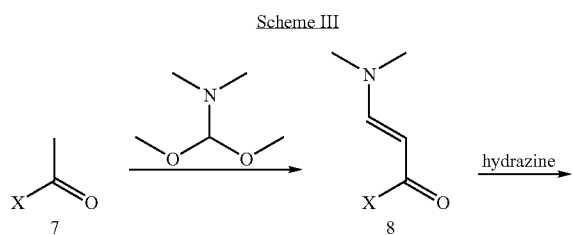

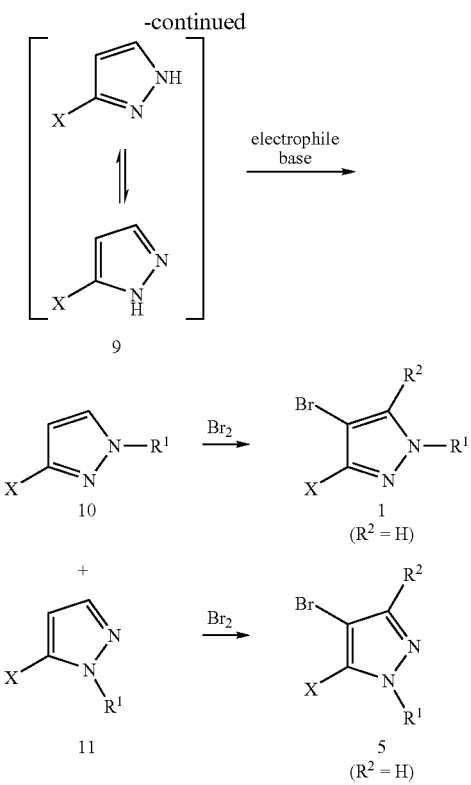

Scheme III shows a synthetic route to the intermediate bromopyrazoles 1 and 5, where R$^2$ is H. The enaminoketone 8 is prepared by the reaction of the acetyl starting material 7 with N,N-dimethylformamide dimethylacetal in a suitable solvent, such as toluene, at reflux (e.g. Example 1, where X is 4-pyridyl). Enaminoketone 8 is then cyclized to the tautomeric pyrazole 9 by heating with excess hydrazine monohydrate in ethanol. In the presence of base and an electrophile, pyrazole 9 can be substituted with R$^1$. Suitable electrophiles include, but are not limited to alkyl halides, cycloalkyl halides, heterocyclyl halides, alkyl tosylates and mesylates, cycloalkyl tosylates and mesylates, heterocyclyl tosylates and mesylates, acid chlorides, sulfonyl chlorides, activated alkyl esters, activated aryl esters, epoxides, α,β-unsaturated ketones, and activated aryl halides. Bromination of pyrazoles 10 and 11 provides the intermediate bromopyrazoles 1 and 5, where $R^2$ is H. Bromination reactions can be carried out using bromine in a suitable solvent such as chloroform, chloroform and methanol mixture, or an acetic acid and sodium acetate mixture. Typically, the bromination can be conducted between −40° C. and room temperature, preferably at 0° C. As an alternative to bromine, N-bromosuccinimide can be used to accomplish the bromination of pyrazoles 10 and 11.

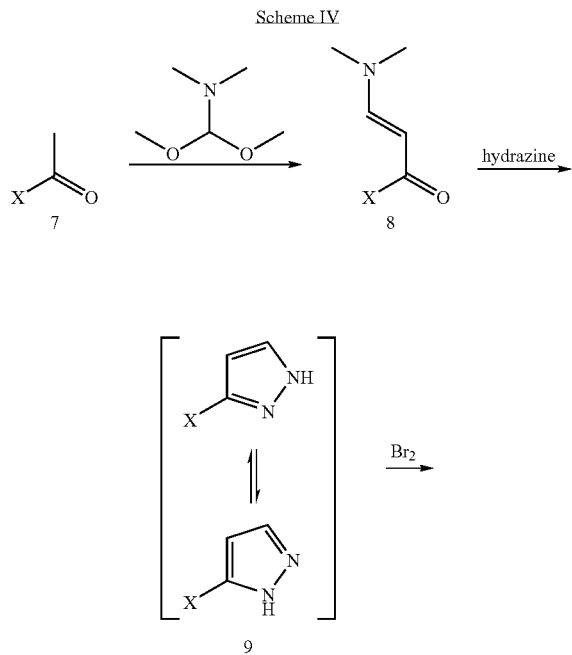

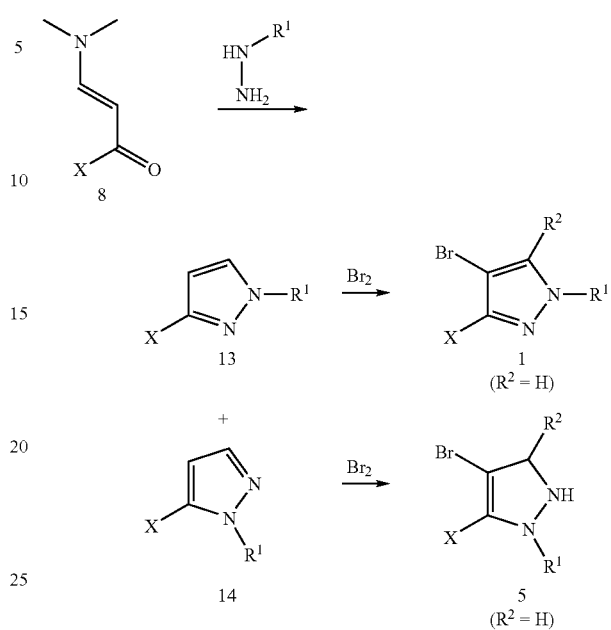

Another synthetic route to the intermediate pyrazoles 1 and 5, where $R^2$ is H, is shown in Scheme V. The previously described enaminoketone 8 can be cyclized with monosubstituted hydrazines by heating in a suitable solvent, such as ethanol. The resulting mixture of pyrazoles 13 and 14 is separated by chromatography and/or recrystallization. Bromination by the methods described above affords the intermediate bromopyrazoles 1 and 5, where $R^2$ is H.

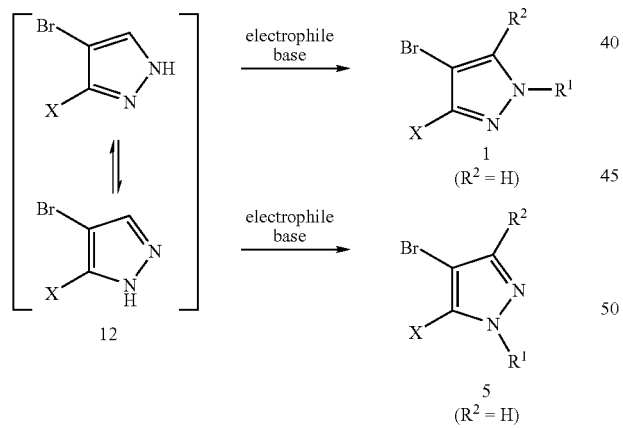

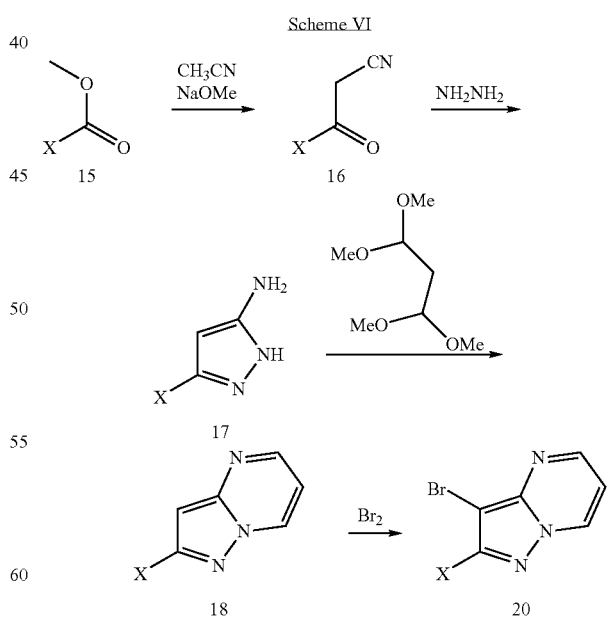

An alternative route to the intermediate bromopyrazoles 1 and 5, where $R^2$ is H, is shown in Scheme IV. The steps are essentially the same as in Scheme III, but in a different order. The previously described substituted pyrazole 9 is brominated in a similar fashion as described above in Scheme III. The resulting bromopyrazole tautomeric mixture 12 is treated with a base and an electrophile to afford the $R^1$-substituted intermediate bromopyrazoles 1 and 5, where $R^2$ is H.

Synthetic Scheme VI shows the synthesis of the intermediate bromopyrazolylpyrimidine 20, which represents an example of structure 1a in Scheme I, where $R^1$ and $R^2$ form a fused heterocycle ring. Ester 15 is converted to ketonitrile 16 by treatment with sodium methoxide and acetonitrile in refluxing toluene. The ketonitrile 16 is cyclized to aminopyrazole 17 by heating with hydrazine in a suitable solvent, such as ethanol. Pyrazolylpyrimidine 18 is prepared by treating aminopyrazole 17 with malonaldehyde bis(dimethyl acetal), catalytic zinc chloride, and hydrochloric acid in refluxing ethanol. Pyrazolylpyrimidine 18 is brominated with bromine in chloroform solution to yield the intermediate bromopyrazolylpyrimidine 20.

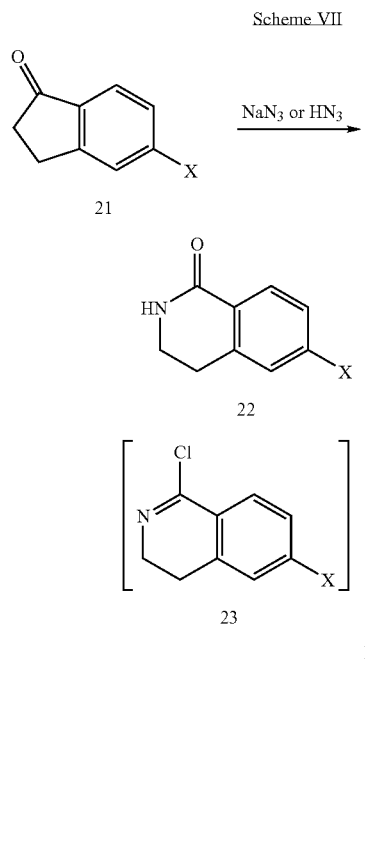

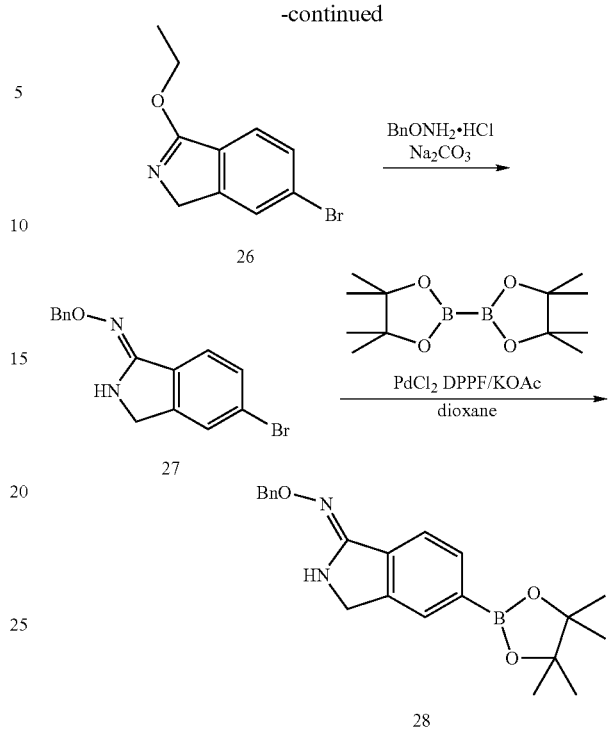

Scheme VII shows the synthesis of 3,4-dihydroisoquinolin-1(2H)-one oxime intermediate 24. Indanone intermediate 21 may be ring expanded to 3,4-dihydroisoquinolin-1(2H)-one lactam intermediate 22 with azide reagents. Vilsemeier-Hack type activation with phosphorus pentachloride and hydroxylamine displacement of chloride from intermediate 23 gives N-hydroxyacetamidine intermediate 24. Where X is B(OH)$_2$ or Br, intermediate 24 can be coupled by Suzuki reaction with intermediates 1, 3, 5, or 6 as in Schemes I and II.

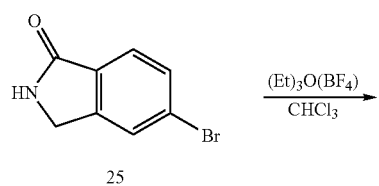

Scheme VIII shows the synthesis of a benzyl-protected isoindolin-1-one oxime intermediate 27. Isoindolinone 25 is alkylated with triethyloxonium tetrafluoroborate in chloroform to afford the 3-ethoxy-1H-isoindole 26, which is reacted with O-benzylhydroxylamine hydrochloride and sodium carbonate in ethanol, providing intermediate 27. Intermediate 27 can be coupled by Suzuki reaction with intermediates 3 or 6 as in Schemes I and II. Alternatively, intermediate 27 can be converted to the boronate ester intermediate 28 by reaction with bis(pinacolato)diboron in dioxane, using [1,1'-bis(diphenylphosphino)ferrocene]palladium(II)chloride dichloromethane complex. The boronate ester intermediate 28 can be coupled by Suzuki reaction with intermediates 1 or 5 as in Schemes I and II.

Methods of Separation

In each of the exemplary Schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g. an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g. (−) menthyl chloroformate in the presence of base, or Mosher ester, α-methoxy-α-(trifluoromethyl)phenyl acetate (Jacob III. (1982) J. Org. Chem. 47:4165), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, (1990) J. of Chromatogr. 513:375-378). Enriched or purified enantiomers can be distinguished by methods used to distinguish other chiral molecules with asymmetric carbon atoms, such as optical rotation and circular dichroism.

Positional isomers, such as the E and Z forms of oxime-containing compounds of Formula Ia and Ib compounds, and intermediates for their synthesis, may be observed by characterization methods such as NMR and analytical HPLC. For certain compounds where the energy barrier for interconversion is sufficiently high, the E and Z oxime isomers may be separated, for example by preparatory HPLC.

Biological Evaluation

B-Raf mutant protein 447-717 (V600E) was co-expressed with the chaperone protein Cdc37, complexed with Hsp90 (Roe et al (2004) Cell 116:87-98; Stancato et al (1993) J. Biol. Chem. 268:21711-21716).

Determining the activity of Raf in the sample is possible by a number of direct and indirect detection methods (US 2004/082014). Activity of human recombinant B-Raf protein may be assessed in vitro by assay of the incorporation of radiolabelled phosphate to recombinant MAP kinase (MEK), a known physiologic substrate of B-Raf, according to US 2004/127496 and WO 03/022840. The activity/inhibition of V600E full-length B-Raf was estimated by measuring the incorporation of radiolabeled phosphate from [$\gamma$-$^{33}$P]ATP into FSBA-modified wild-type MEK (Example 8).

Suitable methods of Raf activity depend on the nature of the sample. In cells, the activity of Raf is on the one hand determined by the amount of the Raf expressed in the cell, and on the other hand by the amount of the activated Raf. The activation of the transcription of the genes coding for Raf protein, in particular B-Raf protein, may for instance be made by determining the amount of the Raf mRNA. Prior art standard methods comprise for instance the DNA chip hybridization, RT-PCR, primer extension and RNA protection. Furthermore, the determination of the Raf activity based on the induction or repression of the transcription of the respective Raf gene(s), may also take place by the coupling of the Raf promoter to suitable reporter gene constructs. Examples for suitable reporter genes are the chloramphenicol transferase gene, the green fluorescent protein (GFP) and variants thereof, the luciferase gene and the Renilla gene. The detection of the increase of expression of Raf proteins may however also be made on the protein level, in this case the amount of protein being detected for instance by antibodies directed against Raf protein. The change of the activity of the Raf protein can however also be put down to increased or reduced phosphorylation or dephosphorylation of the protein. For instance, the B-Raf kinase is regulated by the phosphorylation of the 599Thr and 602Ser remainders (Zhang B. H. and Guan K. L. (2000) EMBO J. 19:5429). The change of the phosphorylation of B-Raf proteins may for instance be detected by antibodies directed against phosphorylated threonine or serine.

Since Raf proteins are threonine/serine kinases, the activity of the Raf proteins can also be determined by their enzymatic activity. The protein MEK is for instance a substrate of B-Raf and the degree of the phosphorylation of MEK permits the determination of the B-Raf activity in the sample. In the same way, the phosphorylation of other substrates, as for instance MBP and peptides which are specifically phosphorylated by Raf (Salh et al. (1999) Anticancer Res. 19:731-740; Bondzi et al. (2000) Oncogene 19:5030-5033), of the Raf proteins can be used for determining the respective activity. Since Raf is part of a signal cascade where a series of kinases are respectively phosphorylated and activated by a superordinated kinase, the activity of Raf can also be determined by evaluating the phosphorylation degree of each kinase subordinated to Raf. This so-called map kinase pathway leads, among other features, also to a specific activation of transcription factors and thus to a transcriptional activation of genes, such that the activity of Raf can indirectly be determined by measuring the activity of these target genes.

The activity of test compounds (Formulas Ia and Ib) as B-Raf inhibitors may be determined by the in vitro fluorescence anisotropy kinase binding assay as described in Example 9, and according to US 2004/127496 and WO 03/022840.

The neuroprotective properties of B-Raf inhibitors may be determined by the in vitro assay in Rat Hippocampal Slice Cultures, according to US 2004/127496; US 2004/082014; WO 03/022840 and as described in Example 10.

The ERK inhibition properties of the compounds of the invention may also be determined by the spectrophotometric coupled-enzyme assay as described in Example 11 (Fox et al. (1998) Protein Sci. 7:2249).

Inhibition of basal ERK1/2 phosphorylation was determined by incubating Malme 3-M cells with compound for 1 hour and quantifying the fluorescent pERK signal on fixed cells and normalizing to total ERK signal according to the protocol of Example 12. The ERK inhibition properties of the compounds of the invention may also be determined by the in vitro cellular proliferation assay as described in Example 12, and according to US 2003/0139452.

Viable cells after a 3 day incubation with compound were quantified using the MTS/PMS colorimetric assay as described in Example 13.

Exemplary compounds 101-160 listed in Table 1 were prepared, characterized, and assayed for their B-Raf binding activity and in vitro activity against tumor cells. The range of B-Raf binding activities was less than 1 nM to about 10 µM. Certain exemplary compounds of the invention had B-Raf binding activity $IC_{50}$ values less than 10 nM. Certain compounds of the invention had cell-based activity, i.e. cells expressing activated mutants of the B-Raf target kinase, $IC_{50}$ values less than 100 nM.

Administration of Pyrazolyl Compounds

The pyrazolyl compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary, and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the pyrazolyl compound is administered orally, it may be formulated as a pill, capsule, tablet, etc. with a pharmaceutically acceptable carrier or excipient. Where the pyrazolyl compound is administered parenterally, it may be formulated with a pharmaceutically acceptable parenteral vehicle and in a unit dosage injectable form, as detailed below.

A dose to treat human patients may range from about 10 mg to about 1000 mg of pyrazolyl compound. A typical dose may be about 100 mg to about 300 mg of of pyrazolyl compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Another aspect of this invention provides a compound of this invention for use as a medicament in the treatment of the diseases or conditions described herein in a mammal, for example, a human, suffering from such disease or condition. Also provided is the use of a compound of this invention in the preparation of a medicament for the treatment of the diseases and conditions described herein in a warm-blooded animal, such as a mammal, for example a human, suffering from such disorder.

Pharmaceutical Formulations of Pyrazolyl Compounds

Compounds of the present invention are useful for treating diseases, conditions and/or disorders characterized by over expression of Raf kinases, e.g. B-Raf kinase; therefore, another embodiment of the present invention is a pharmaceutical composition, i.e. formulation, comprising a therapeutically effective amount of a compound of the present invention and a pharmaceutically acceptable excipient, diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound, such as a complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical, formulations of therapeutic pyrazolyl compounds of the invention may be prepared for various routes and types of administration. A pyrazolyl compound having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The inhibitory compound for use herein is preferably sterile. The compound ordinarily will be stored as a solid composition, although lyophilized formulations or aqueous solutions are acceptable.

The pharmaceutical compositions of the invention will be formulated, dosed, and administered in a fashion, i.e. amounts, concentrations, schedules, course, vehicles, and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients, and stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the pyrazolyl compound, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid.

The formulations to be used for in vivo administration must be sterile, which is readily accomplished by filtration through sterile filtration membranes.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of pyrazolyl compound suitable for oral administration may be prepared as discrete units such as pills, capsules, cachets or tablets each containing a predetermined amount of the pyrazolyl compound.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g. gelatin capsules, syrups or elixirs may be prepared for oral use. Formulations of a pyrazolyl compound intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For infections of the eye or other external tissues e.g. mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of the invention contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical composition of a pyrazolyl compound may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of HIV infections as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

A pyrazolyl compound of the invention may be combined in a pharmaceutical combination formulation, or dosing regimen as combination therapy, with a second compound that has anti-hyperproliferative properties or that is useful for treating a hyperproliferative disorder (e.g. cancer). The second compound of the pharmaceutical combination formulation or dosing regimen preferably has complementary activities to the pyrazolyl compound of the combination such that they do not adversely affect each other. Such molecules are suitably present in combination in amounts that are effective for the purpose intended.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

Metabolites of the Pyrazolyl Compounds

Also falling within the scope of this invention are the in vivo metabolic products of the pyrazolyl compounds described herein, to the extent such products are novel and unobvious over the prior art. Such products may result for example from the oxidation, reduction, hydrolysis, amidation, deamidation, esterification, deesterification, enzymatic cleavage, and the like, of the administered compound. Accordingly, the invention includes novel and unobvious compounds produced by a process comprising contacting a compound of this invention with a mammal for a period of time sufficient to yield a metabolic product thereof.

Metabolite products typically are identified by preparing a radiolabelled (e.g. $^{14}C$ or $^{3}H$) isotope of a compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, LC/MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the pyrazolyl compounds of the invention.

Articles of Manufacture

In another embodiment of the invention, an article of manufacture, or "kit", containing materials useful for the treatment of the disorders described above is provided. The article of manufacture comprises a container and a label or package insert on or associated with the container. Suitable containers include, for example, bottles, vials, syringes, blister pack, etc. The containers may be formed from a variety of materials such as glass or plastic. The container holds a pyrazolyl compound or formulation thereof which is effective for treating the condition and may have a sterile access port (for example the container may be an intravenous solution bag or a vial having a stopper pierceable by a hypodermic injection needle). At least one active agent in the composition is a pyrazolyl compound of the invention. The label or package insert indicates that the composition is used for treating the condition of choice, such as cancer. In one embodiment, the label or package inserts indicates that the composition comprising the pyrazolyl compound can be used to treat a thromboembolic disorder. In addition, the label or package insert may indicate that the patient to be treated is one having a thromboembolic disorder characterized by excessive bleeding. The label or package insert may also indicate that the composition can be used to treat other disorders.

The article of manufacture may comprise (a) a first container with a pyrazolyl compound contained therein; and (b) a second container with a second pharmaceutical formulation contained therein, wherein the second pharmaceutical formulation comprises a second compound with anti-hyperproliferative activity. The article of manufacture in this embodiment of the invention may further comprise a package insert indicating that the first and second compounds can be used to treat patients at risk of stroke, thrombus or thrombosis disorder. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other Raf inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted on a Biotage system (Manufacturer: Dyax Corporation) having a silica gel column or on a silica SEP PAK® cartridge (Waters). $^1$H NMR spectra were recorded on a Varian instrument operating at 400 MHz. $^1$H NMR spectra were obtained as $CDCl_3$, $d_6$-DMSO or $d_4$ MeOH solutions (reported in ppm), using chloroform as the reference standard (7.25 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

5-(1-Methyl-5-pyridin-4-yl-1H-pyrazol-4-yl)-2,3-dihydroinden-1-one oxime 122

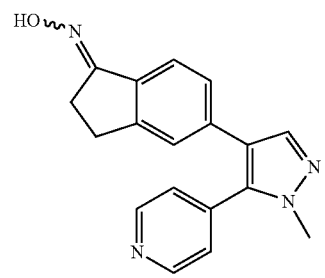

122

Step 1: Preparation of (E)-3-(dimethylamino)-1-(pyridin-4-yl)prop-2-en-1-one: To 4-acetylpyridine (23 mL) in 350 mL toluene was added 55 mL N,N-dimethylformamide dimethyl acetal. The solution was refluxed for 3 hours and allowed to stir at ambient temperature overnight. An additional 33 mL N,N-dimethylformamide dimethyl acetal of was added. After refluxing for 7 hours, the mixture was concentrated to leave an orange solid. This material was treated with diethyl ether. The resulting yellow solid was collected by vacuum filtration. A total of 25.85 g (71% yield) yellow solid was obtained. $^1$H NMR ($CDCl_3$) was consistent with the desired structure. LC/MS indicated a single peak with a M+1 molecular ion of m/z 177.1 by positive ESI (electrospray ionization mass spectrometry).

Step 2: Preparation of 4-(1-methyl-1H-pyrazole-5-yl)pyridine: To (E)-3-(dimethylamino)-1-(pyridin-4-yl)prop-2-en-1-one (1.00 g) in 50 mL ethanol was added 0.32 mL methylhydrazine and the resulting mixture heated to reflux for 1 hour. The solvent was removed by evaporation and partitioned between ethyl acetate and water. The aqueous layer was extracted with another portion of ethyl acetate. The combined ethyl acetate extracts were washed with brine, dried over magnesium sulfate, filtered, and evaporated to afford 0.62 g crude product as a yellow oil. The material was purified by chromatography, eluting with a 10:1 mixture of dichloromethane-methanol to yield 0.30 g (64% yield) product as a yellow oil. $^1$H NMR ($CDCl_3$) was consistent with a 3.8:1 mixture of desired product and undesired isomer (4-(1-methyl-1-H-pyrazole-3-yl)pyridine). LC/MS of the mixture showed 2 peaks, each with a M+1 molecular ion of m/z 160.2 by positive ESI.

Step 3: Preparation of 4-(4-bromo-1-methyl-1H-pyrazol-5-yl)pyridine: To a 3.8:1 isomer mix of 4-(1-methyl-1H-pyrazole-5-yl)pyridine and 4-(1-methyl-1-H-pyrazole-3-yl)pyridine (0.30 g) in 5 mL chloroform cooled in ice, was added a solution of 104 μL bromine in 3 mL chloroform. After 5 h, the mixture was treated with excess saturated aqueous sodium bicarbonate and diluted with dichloromethane. The dichloromethane was washed with 3 portions of saturated aqueous sodium bicarbonate, dried over magnesium sulfate, filtered, and evaporated to yield 0.39 g crude product as a brown oil. The crude product was purified by chromatography, eluting with 15:1 ethyl acetate-methanol. Fractions containing the major component were combined to afford 0.17 g (73% yield) of a colorless oil. $^1$H NMR ($CDCl_3$) was consistent with the desired structure. LC/MS indicated one major product with a M+1 molecular ion of m/z 240.3 by positive ESI.

Step 4: Preparation of (E)-5-bromo-2,3-dihydroinden-1-one O-methyl oxime: To 5-bromoindanone (6.03 g) in 40 mL ethanol was added 3.58 g methoxylamine hydrochloride and 3.5 mL pyridine. The mixture was stirred at ambient temperature for 1 hour and heated at 80° C. for 3 hours. The volatiles were removed under vacuum and the solid residue partitioned between ethyl acetate and saturated aqueous sodium bicarbonate. The ethyl acetate was washed with brine, dried over magnesium sulfate, filtered, and evaporated under vacuum to yield 6.74 g (98% yield) of a tan solid. $^1$H NMR (CDCl$_3$) was consistent with an isomeric mixture of the desired structure, with the E oxime isomer as the major component. LC/MS indicated 2 close peaks, both with a M+1 molecular ion of m/z 242.0 by positive ESI.

Step 5: Preparation of (E)-1-(methoxyimino)-2,3-dihydro-1H-inden-5-ylboronic acid: To (E)-5-bromo-2,3-dihydroinden-1-one O-methyl oxime (3.00 g) in 100 mL tetrahydrofuran cooled in dry ice-acetone, was added dropwise, 5.5 mL of a 2.5 M n-butyllithium solution in hexane. A tan precipitate formed. After 30 minutes at −78° C., 3.1 mL trimethylborate was added and the mixture allowed to warm to ambient temperature and allowed to stir overnight. The reaction mixture was evaporated under vacuum and acidified to pH 1 with 6M hydrochloric acid, stirred 15 min, basified with 2M sodium hydroxide, washed with 3 portions diethyl ether, acidified to pH 1 with 6M hydrochloric acid and extracted with 3 portions of ethyl acetate. The combined ethyl acetate extracts were washed with brine, dried over magnesium sulfate, filtered, and evaporated under vacuum to yield 1.95 g pale yellow solid. The crude solid was triturated with a hexane/diethyl ether mixture to afford 1.46 g (57% yield) product as a tan solid. $^1$H NMR (d$_6$ DMSO) was consistent with the desired product. LC/MS showed one peak with a M+1 molecular ion of m/z 206.1 by positive ESI.

Step 6: Preparation of (E)-5-(1-methyl-5-(pyridin-4-yl)-1H-pyrazol-4-yl)-2,3-dihydroinden-1-one O-methyl oxime: To a solution of 4-(4-bromo-1-methyl-1H-pyrazol-5-yl)pyridine (0.17 g) in 7 mL dimethoxyethane and 3 mL water, was added 0.146 g (E)-1-(methoxyimino)-2,3-dihydro-1H-inden-5-ylboronic acid (product of Example 1, Step 5), and 0.79 g K$_2$CO$_3$. To this mixture was added approximately 20 mg tetrakis(triphenyphosphine)palladium(0) and the suspension heated to reflux. After 4 hours, the cooled reaction mixture was filtered through celite and the filter cake was washed with ethyl acetate. The filtrate was washed with water, brine, dried over magnesium sulfate, filtered, and evaporated under vacuum to yield 0.63 g crude product as a tan semisolid. The material was suspended in ethyl acetate and filtered. The filtrate was evaporated under vacuum, and the residue purified by chromatography, eluting with ethyl acetate to provide 82.6 mg (36% yield) product as a colorless glass. $^1$H NMR (CDCl$_3$) was consistent with the desired product. LC/MS indicated one peak with a M+1 molecular ion of m/z 319.2 by positive ESI.

Step 7: Preparation of 5-(1-methyl-5-(pyridin-4-yl)-1H-pyrazol-4-yl)-2,3-dihydroinden-1-one: To (E)-5-(1-methyl-5-(pyridin-4-yl)-1H-pyrazol-4-yl)-2,3-dihydroinden-1-one O-methyl oxime (82.6 mg) in 2 mL dioxane and 5 mL acetone was added 0.5 mL 5M hydrochloric acid. The mixture was heated at reflux for 2 hours. The cooled reaction mixture was evaporated under vacuum and partitioned between saturated aqueous sodium bicarbonate and ethyl acetate. The ethyl acetate was washed with brine, dried over magnesium sulfate, filtered, and evaporated under vacuum to yield 0.05 g crude product as an oil. The material was purified by chromatography, eluting with a 15:1 mixture of ethyl acetate-methanol to yield 50.9 mg (68% yield) of a colorless oil. $^1$H NMR (CDCl$_3$) was consistent with the desired product. LC/MS indicated one peak with a M+1 molecular ion of m/z 290.4 by positive ESI.

Step 8: Preparation of 5-(1-methyl-5-pyridin-4-yl-1H-pyrazol-4-yl)-indan-1-one oxime 122: To 5-(1-methyl-5-(pyridin-4-yl)-1H-pyrazol-4-yl)-2,3-dihydroinden-1-one (0.051 g) in 3 mL ethanol was added 1 mL water and hydroxylamine hydrochloride (37 mg). The mixture was heated to reflux. After 2 hours, the mixture was cooled and evaporated under vacuum. The residue was partitioned between saturated aqueous sodium bicarbonate and ethyl acetate. The ethyl acetate was washed with brine, dried over magnesium sulfate, filtered, and evaporated under vacuum to afford crude product. The material was triturated with a small portion of methanol and dried to yield 40 mg (74% yield) of a white solid. $^1$H NMR(CDCl$_3$) was consistent with 5-(1-methyl-5-pyridin-4-yl-1H-pyrazol-4-yl)-indan-1-one oxime 122. LC/MS showed a single peak with a M+1 molecular ion of m/z 305.2 by positive ESI.

Example 2

5-(1-(2-hydroxyethyl)-5-pyridin-4-yl-1H-pyrazol-4-yl)-2,3-dihydroinden-1-one oxime 123

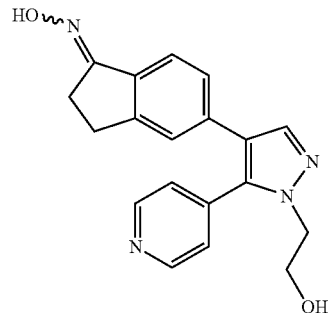

Step 1: Preparation of 2-(5-(pyridin-4-yl)-1H-pyrazol-1-yl)ethanol: To (E)-3-(dimethylamino)-1-(pyridin-4-yl)prop-2-en-1-one (1.00 g; Example 1, Step 1) in 50 mL ethanol, was added 2-hydroxyethylhydrazine (0.404 mL) and the mixture heated to reflux. After 4 hours, the reaction was evaporated under vacuum to yield a yellow oil. The crude product was purified by chromatography, eluting with a mixture of 4:1 ethyl acetate-methanol to afford 0.69 g (64% yield) of product as a white semisolid. $^1$H NMR (CDCl$_3$) indicated a 3.4:1 mixture of isomers consistent with the desired product as the major component and 2-(3-(pyridin-4-yl)-1H-pyrazol-1-yl)ethanol as the minor component. LC/MS showed 2 close peaks, both with a M+1 molecular ion of m/z 190.2 by positive ESI.

Step 2: Preparation of 2-(4-bromo-5-(pyridin-4-yl)-1H-pyrazol-1-yl)ethanol: To of a 3.4:1 isomer mixture of 2-(5-(pyridin-4-yl)-1H-pyrazol-1-yl)ethanol and 2-(3-(pyridin-4-yl)-1H-pyrazol-1-yl)ethanol (0.69 g) in 10 mL chloroform cooled in ice, was added a solution of 200 μL bromine in 5 mL chloroform. After 1 hour, the mixture was treated with saturated aqueous sodium bicarbonate and diluted with dichloromethane. The dichloromethane layer was washed with 3 portions of saturated aqueous sodium bicarbonate, dried over magnesium sulfate, filtered, and evaporated to yield 0.96 g crude product as a brown oil. The crude material was purified by chromatography, eluting with a mixture of 8:1 ethyl acetate-methanol to afford 0.23 g (23% yield) of product as a colorless oil. $^1$H NMR (CDCl$_3$) was consistent with the desired product. LC/MS indicated one peak with a M+1 molecular ion of m/z 270.2 by positive ESI.

Step 3: Preparation of (E)-5-bromo-2,3-dihydroinden-1-one O-benzyl oxime: To 5-bromoindanone (5.66 g) in 60 mL ethanol was added 5.57 g O-benzylhydroxylamine hydrochloride and 3.2 mL pyridine. The mixture was stirred at ambient temperature for 5 hours. The volatiles were removed under vacuum and the solid residue partitioned between saturated aqueous sodium bicarbonate and ethyl acetate. The ethyl acetate was washed with brine, dried over magnesium sulfate, filtered, and evaporated under vacuum to afford crude product as an amber oil. The crude material was crystallized from hexane to afford 5.43 g (84% yield) light tan solid. $^1$H NMR (CDCl$_3$) was consistent with the desired product. LC/MS indicated a single peak with a M+1 molecular ion of m/z 318.1 by positive ESI.

Step 4: Preparation of (E)-1-(benzyloxyimino)-2,3-dihydro-1H-inden-5-ylboronic acid: To (E)-5-bromo-2,3-dihydroinden-1-one O-benzyl oxime (5.00 g; Example 2, step 3) in 200 mL tetrahydrofuran cooled in dry ice/acetone was added 7.0 mL of a 2.5 M solution of n-butyllithium in hexane dropwise. After 20 minutes, 3.9 mL trimethylborate was added at −78° C. to the clear brown solution and the reaction mixture was allowed to warm to ambient temperature for 2 hours. The solvent was evaporated under vacuum and the residue treated with water and acidified with 1M hydrochloric acid until pH 3. After stirring 5 minutes, the mixture was basified with 2M sodium hydroxide and extracted with 3 portions of diethyl ether. The diethyl ether extracts were extracted with 2 portions of 0.5M sodium hydroxide. The combined aqueous extracts were acidified to pH 1 with 1M hydrochloric acid and extracted with 2 portions of ethyl acetate. The combined ethyl acetate extracts were dried over magnesium sulfate, filtered, and evaporated to yield 3.46 g (78% yield) product as a tan solid. $^1$H NMR (d$_6$ DMSO) was consistent with the desired product. LC/MS indicated a peak with a M+1 molecular ion of m/z 282.1 by positive ESI.

Step 5: Preparation of (E)-5-(1-(2-hydroxyethyl)-5-(pyridin-4-yl)-1H-pyrazol-4-yl)-2,3-dihydroinden-1-one O-benzyl oxime: To 2-(4-bromo-5-(pyridin-4-yl)-1H-pyrazol-1-yl) ethanol (0.050 g; Example 2, Step 2) dissolved in 5 mL acetonitrile was added 2 mL water, (E)-1-(benzyloxyimino)-2,3-dihydro-1H-inden-5-ylboronic acid (0.058 g; Example 2, Step 4), and 0.155 g potassium carbonate. The mixture was purged with nitrogen and about 20 mg tetrakis(triphenyphosphine)palladium(0) catalyst was added. The mixture was heated at 75° C. After 1 hour, the reaction mixture was filtered through celite, the filter cake washed with ethyl acetate, and the filtrate evaporated under vacuum. The residue was partitioned between ethyl acetate and water. The ethyl acetate was washed with saturated aqueous sodium carbonate, brine, dried over magnesium sulfate, filtered, and evaporated under vacuum to yield 0.05 g crude product as a colorless glass. The crude material was purified by chromatography, eluting with a mixture of 8:1 dichloromethane-methanol to afford 18.6 mg (23% yield) product as a colorless glass. $^1$H NMR (CDCl$_3$) was consistent with the desired structure. LC/MS showed one peak with a M+1 molecular ion of m/z 425.2 by positive ESI.

Step 6: Preparation of 5-(1-(2-hydroxyethyl)-5-pyridin-4-yl-1H-pyrazol-4-yl)-2,3-dihydroinden-1-one oxime 123: To (E)-5-(1-(2-hydroxyethyl)-5-(pyridin-4-yl)-1H-pyrazol-4-yl)-2,3-dihydroinden-1-one O-benzyl oxime (15.8 mg; Example 2, Step 5) in 5 mL methanol was added 1 drop 6M hydrochloric acid and about 5 mg palladium hydroxide (20% by weight on carbon). A hydrogen-filled balloon was attached to the reaction vessel and the mixture was stirred at ambient temperature for 1 hour. The mixture was filtered through celite and the celite was washed with methanol. The filtrate was concentrated under vacuum and the residue was partitioned between saturated aqueous sodium carbonate and ethyl acetate. The ethyl acetate was washed with brine, dried over magnesium sulfate, filtered, and evaporated to yield 9.1 mg (73% yield) of a white solid. $^1$H NMR (d$_4$ MeOH) was consistent with the desired structure 123. LC/MS showed one peak with a M+1 molecular ion of m/z 335.3 by positive ESI.

Example 3

5-(1-Methyl-3-pyridin-4-yl-1H-pyrazol-4-yl)-2,3-dihydroinden-1-one oxime 113

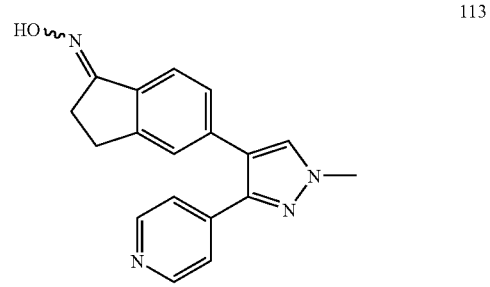

Step 1: Preparation of 4-(1H-pyrazol-3-yl)pyridine: To 50 mL absolute ethanol was added (E)-3-(dimethylamino)-1-(pyridin-4-yl)prop-2-en-1-one (20 g; Example 1, Step 1). When all solids dissolved, 6.33 mL hydrazine monohydrate was added dropwise with stirring. After 30 minutes an additional 1.1 mL hydrazine hydrate was added. After 2 hours the reaction was treated with water and the yellow solution was concentrated under vacuum until a slurry formed. The resulting solid product was collected by vacuum filtration, washed with water, and dried under high vacuum overnight to yield 15.27 g (93% yield) of product as off-white crystals. $^1$H NMR (CDCl$_3$) was consistent with a tautomeric mixture of the desired structure. LC/MS showed one peak with a M+1 molecular ion of m/z 146.4 by positive ESI.

Step 2: Preparation of 4-(1-methyl-1H-pyrazol-3-yl)pyridine: To 150 mL tetrahydrofuran was added 4-(1H-pyrazol-3-yl)pyridine (4.96 g; Example 3, Step 1) and the solution cooled in ice. To this was added slowly 1.64 g of a 60% suspension of sodium hydride in mineral oil. After gas evolution ceased, the mixture was stirred at ambient temperature for 30 min, cooled back down in ice, and 3.4 mL dimethylsulfate was added. The mixture was allowed to slowly warm to ambient temperature. After 1 hour the reaction mixture was evaporated and the dark brown residue partitioned between saturated aqueous sodium bicarbonate and ethyl acetate. The ethyl acetate was washed with saturated aqueous sodium bicarbonate, brine, dried over magnesium sulfate, filtered, and evaporated under vacuum to afford 4.6 g crude product as a pale yellow solid. The crude material was taken up in a diethyl ether and hexane mixture, filtered through celite, and allowed to crystallize. A total of 2.98 g (55% yield) pale yellow crystals were obtained. $^1$H NMR (CDCl$_3$) was consistent with a single isomer of the desired structure. LC/MS showed one peak with a M+1 molecular ion of m/z 160.5 by positive ESI.

Step 3: Preparation of 4-(4-bromo-1-methyl-1H-pyrazol-3-yl)pyridine: To a solution of 4-(1-methyl-1H-pyrazol-3-yl)pyridine 2.98 g; Example 3, Step 2) in 50 mL chloroform cooled in ice, was added dropwise, a solution of 1.15 mL bromine in 30 mL chloroform. About 15 mL methanol was added to help dissolution of the yellow precipitate that formed. After 4 hours, the reaction mixture was quenched with saturated aqueous sodium bicarbonate and diluted with dichloromethane. The dichloromethane layer was washed with saturated aqueous sodium bicarbonate, brine, dried over magnesium sulfate, filtered, and evaporated to yield the crude product as a yellow semisolid. The crude material was slurried in ethyl acetate and filtered through celite. The filtrate was evaporated to yield 4.18 g product as a yellow solid. $^1$H NMR (CDCl$_3$) was consistent with the desired structure. LC/MS showed one peak with a M+1 molecular ion of m/z 240.5 by positive ESI.

Step 4: Preparation of 5-(1-methyl-3-(pyridin-4-yl)-1H-pyrazol-4-yl)-2,3-dihydroinden-1-one O-benzyl oxime: To (E)-1-(benzyloxyimino)-2,3-dihydro-1H-inden-5-ylboronic acid (3.00 g; Example 2, Step 4) in 32 mL acetonitrile and 8.0 mL water was added 4-(4-bromo-1-methyl-1H-pyrazol-3-yl)pyridine (2.00 g; Example 3, Step 3). The solution was deoxygenated by bubbling nitrogen through the solution for 10 min. To the resulting mixture was added 5.62 g potassium carbonate, 10 mL N,N-dimethylformamide, and 290 mg tetrakis(triphenyphosphine)palladium(0). The mixture was then refluxed for 8 hours (over the course of this time a small portion of catalyst was added twice). The cooled reaction mixture was filtered through celite and the filter cake was washed with ethyl acetate. The filtrate was washed with water, brine, dried over sodium sulfate, filtered, and evaporated under vacuum to yield 5.1 g crude product as an oil. The crude material was purified by chromatography, eluting with ethyl acetate to afford 2.50 g (80% yield) product as a light yellow foam. $^1$H NMR (CDCl$_3$) was consistent with the desired structure. LC/MS showed one peak with a M+1 molecular ion of m/z 395.2 by positive ESI.

Step 5: Preparation of 5-(1-Methyl-3-pyridin-4-yl-1H-pyrazol-4-yl)-2,3-dihydroinden-1-one oxime 113: To 5-(1-methyl-3-(pyridin-4-yl)-1H-pyrazol-4-yl)-2,3-dihydroinden-1-one O-benzyl oxime (2.50 g; Example 3, Step 4) in 60 mL methanol was added 0.89 g palladium hydroxide (20% by weight on carbon) and 6.3 mL 6M hydrochloric acid. A hydrogen-filled balloon was attached to the reaction vessel and the mixture was stirred at ambient temperature for 2 hours. The reaction mixture was filtered through celite and the celite was washed with methanol. The filtrate was concentrated under vacuum and the residue was partitioned between saturated aqueous sodium bicarbonate and ethyl acetate. The ethyl acetate was washed with brine and evaporated to yield 1.0 g of crude product as a white solid. The aqueous layer was reextracted with two portions of n-butanol. The n-butanol was evaporated under vacuum to afford an additional 0.4 g crude product as a white solid. The solids were combined and washed with two 15 mL portions of water, dissolved in a 1:1 mixture of dichloromethane-methanol, filtered, and the filtrate evaporated under vacuum. The residue was triturated with ethyl acetate and dried to afford 0.98 g (51% yield) of product as a white solid. $^1$H NMR (CDCl$_3$) was consistent with the desired structure 113. LC/MS showed a peak with a M+1 molecular ion of m/z 305.4 by positive ESI.

Example 4

5-(1-(2-hydroxyethyl)-3-pyridin-4-yl-1H-pyrazol-4-yl)-2,3-dihydroinden-1-one oxime 110

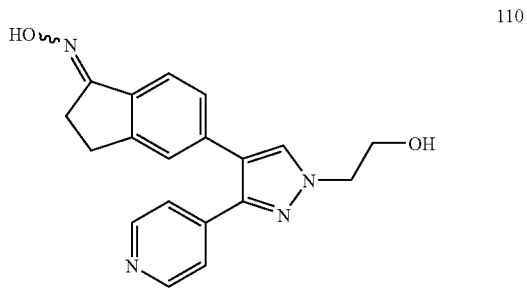

Step 1: Preparation of 4-(4-bromo-1H-pyrazol-3-yl)pyridine: To 4-(1H-pyrazol-3-yl)pyridine (36.1 g; Example 3, Step 1) in 600 mL chloroform and 600 mL acetic acid, was added 20.4 g sodium acetate and the mixture was stirred for 1 hour until homogeneous. The solution was then cooled in an ice bath and a solution of 12 mL bromine in 150 mL acetic acid was added over a 30 minute period. A precipitate formed during bromine addition. After 2 hours, the reaction mixture was diluted with dichloromethane and basified with 4M sodium hydroxide to pH 4. The layers were separated and the aqueous layer was extracted with dichloromethane. The combined dichloromethane extracts were washed with water, then brine, dried over magnesium sulfate and applied to a silica gel plug. The plug was washed with dichloromethane and product was eluted with ethyl acetate and then a 19:1 mixture of ethyl acetate/methanol. The eluent contained 33.2 g (60% yield) product as a white solid. $^1$H NMR (CDCl$_3$) was consistent with a tautomeric mixture of the desired structure. LC/MS showed one peak with a M+1 molecular ion of m/z 226.2 by positive ESI.

Step 2: Preparation of 2-(4-bromo-3-(pyridin-4-yl)-1H-pyrazol-1-yl)ethyl acetate: To 4-(4-bromo-1H-pyrazol-3-yl)pyridine (0.50 g; Example 4, Step 1) in 7 mL N,N-dimethylformamide was added 1.09 g cesium carbonate and 0.27 mL 2-bromoethyl acetate. The resulting suspension was stirred at 60° C. After 1 hour the reaction mixture was diluted with water and extracted with 2 portions of ethyl acetate. The combined ethyl acetate extracts were washed with brine, dried over magnesium sulfate, filtered, and evaporated to yield 0.69 g (100% yield) product as a yellow oil. $^1$H NMR (CDCl$_3$) was consistent with a 9:1 isomer ratio of the desired structure and the regioisomer 2-(4-bromo-5-(pyridin-4-yl)-1H-pyrazol-1-yl)ethyl acetate. LC/MS showed two close peaks, each with a M+1 molecular ion of m/z 312.2 by positive ESI.

Step 3: Preparation of 2-(4-bromo-3-(pyridin-4-yl)-1H-pyrazol-1-yl)ethanol: To a 9:1 isomer mixture of 2-(4-bromo-3-(pyridin-4-yl)-1H-pyrazol-1-yl)ethyl acetate and regioisomer 2-(4-bromo-5-(pyridin-4-yl)-1H-pyrazol-1-yl)ethyl acetate (0.69 g; Example 4, Step 1) in 20 mL methanol was added 5 mL water and 3 mL 2M sodium hydroxide. After 10 minutes the reaction mixture was concentrated under vacuum and the aqueous residue was extracted twice with ethyl acetate. The combined ethyl acetate extracts were washed with brine, dried over magnesium sulfate, filtered, and evaporated under vacuum to yield 0.54 g crude product as a white solid. The crude material was recrystallized from ethyl acetate to yield 0.39 g (60% yield) white solid in 2 crops. $^1$H NMR (CDCl$_3$) was consistent with 1 isomer of the desired product.

Step 4: Preparation of (E)-5-(1-(2-hydroxyethyl)-3-(pyridin-4-yl)-1H-pyrazol-4-yl)-2,3-dihydroinden-1-one O-benzyl oxime: To 2-(4-bromo-3-(pyridin-4-yl)-1H-pyrazol-1-yl)ethanol (100 mg; Example 4, step 3) in 7 mL acetonitrile and 3 mL water, was added 136 mg (E)-1-(benzyloxyimino)-2,3-dihydro-1H-inden-5-ylboronic acid (product of Example 2, Step 4), and 155 mg potassium carbonate. The mixture was purged with nitrogen and about 43 mg tetrakis(triphenyphosphine)palladium(0) catalyst was added. The mixture was heated at 80° C. After 1 hour, the reaction mixture was filtered through celite, the filter cake washed with ethyl acetate, and filtrate evaporated under vacuum. The residue was purified by chromatography, eluting with a mixture of 8:1 ethyl acetate-methanol to afford 110 mg (69% yield) product as a white solid. $^1$H NMR (CDCl$_3$) was consistent with the desired structure. LC/MS showed one peak with a M+1 molecular ion of m/z 425.2 by positive ESI.

Step 5: Preparation of 5-(1-(2-hydroxyethyl)-3-pyridin-4-yl-1H-pyrazol-4-yl)-2,3-dihydroinden-1-one oxime 110: To (E)-5-(1-(2-hydroxyethyl)-3-(pyridin-4-yl)-1H-pyrazol-4-yl)-2,3-dihydroinden-1-one O-benzyl oxime (31.9 mg; Example 4, Step 4) in 5 mL methanol was added 38 µL 6M hydrochloric acid and about 5 mg palladium hydroxide (20% by weight on carbon). A hydrogen-filled balloon was attached to the reaction vessel and the mixture was stirred at ambient temperature for 1 hour. The mixture was filtered through celite, the celite was washed with methanol, and the filtrate treated with a small amount of saturated aqueous sodium bicarbonate. The filtrate was concentrated under vacuum and the residue was purified by chromatography, eluting with a 10:1 mixture of dichloromethane-methanol to yield 13.2 mg (53% yield) of a white solid. $^1$H NMR (CDCl$_3$) was consistent with the desired structure 110. LC/MS showed one peak with a M+1 molecular ion of m/z 335.4 by positive ESI.

Example 5

5-(1-(piperidin-4-yl)-3-pyridin-4-yl-1H-pyrazol-4-yl)-2,3-dihydroinden-1-one oxime 105

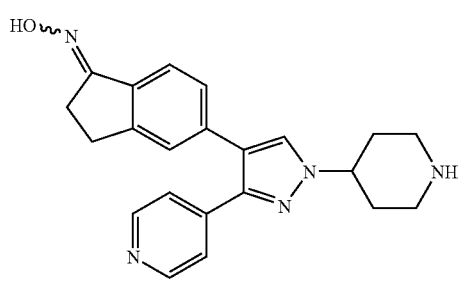

105

Step 1: Preparation of benzyl 4-(4-bromo-3-(pyridin-4-yl)-1H-pyrazol-1-yl)piperidine-1-carboxylate: To 4-(4-bromo-1H-pyrazol-3-yl)-pyridine (1.00 g; Example 4, Step 1) in 13 mL N,N-dimethylformamide was added 2.18 g cesium carbonate and then dropwise, 1.16 mL 4-bromo-N-Z-piperidine. The resulting suspension was stirred at ambient temperature for 10 minutes then heated at 55° C. overnight. The cooled reaction mixture was diluted with water and extracted with 2 portions of ethyl acetate. The ethyl acetate was washed with water, brine, dried over magnesium sulfate, filtered, and evaporated under vacuum to yield 2.48 g crude product as a colorless oil. The crude material was purified by chromatography, eluting with a 9:9:2 mixture of dichloromethane-ethyl acetate-methanol to afford 0.86 g (44% yield) product as a colorless oil. $^1$H NMR (CDCl$_3$) was consistent with a 15:1 mixture of the desired structure and regioisomer benzyl 4-(4-bromo-5-(pyridin-4-yl)-1H-pyrazol-1-yl)piperidine-1-carboxylate. LC/MS showed two peaks, each with a M+1 molecular ion of m/z 444.3 by positive ESI.

Step 2: Preparation of (E)-benzyl 4-(4-(1-(benzyloxyimino)-2,3-dihydro-1H-inden-5-yl)-5-(pyridin-4-yl)-1H-pyrazol-1-yl)piperidine-1-carboxylate: To benzyl 4-(4-bromo-3-(pyridin-4-yl)-1H-pyrazol-1-yl)piperidine-1-carboxylate (0.32 g; Example 5, Step 1) in 10 mL acetonitrile and 3 mL water was added 0.315 g (E)-1-(benzyloxyimino)-2,3-dihydro-1H-inden-5-ylboronic acid (prepared as described in example 2, step 4) and 0.30 g potassium carbonate. The reaction mixture was purged with nitrogen and 84 mg tetrakis(triphenyphosphine)palladium(0) catalyst was added. The reaction mixture heated to 80° C. for 2 hours, filtered through celite, and the filter cake was washed with acetonitrile. The filtrate was evaporated under vacuum to yield crude product. The residue was purified by chromatography, eluting with ethyl acetate to afford 0.36 g (83% yield) product as a colorless oil. $^1$H NMR (CDCl$_3$) was consistent with the desired structure. LC/MS showed one peak with a M+1 molecular ion of m/z 598.3 by positive ESI.

Step 3: Preparation of 5-(1-(piperidin-4-yl)-3-pyridin-4-yl-1H-pyrazol-4-yl)-2,3-dihydroinden-1-one oxime 105: To (E)-benzyl 4-(4-(1-(benzyloxyimino)-2,3-dihydro-1H-inden-5-yl)-5-(pyridin-4-yl)-1H-pyrazol-1-yl)piperidine-1-carboxylate (0.35 g; Example 5, Step 2) in 10 mL methanol was added 390 µL 6M hydrochloric acid and 40 mg palladium hydroxide (20% by weight on carbon). A hydrogen-filled balloon was attached to the reaction vessel and the mixture was stirred at ambient temperature for 1.5 hours. The mixture was filtered through celite and the celite was washed with methanol. The filtrate was concentrated under vacuum and the residue was dissolved in 10 mL dichloromethane and 10 mL methanol, treated with 1.64 g of MP-carbonate resin (2.86 mmol/g loading) for 0.5 hours, filtered and evaporated under vacuum. The crude product was purified by trituration with dichloromethane to yield 0.1492 g (68% yield) of a white solid. $^1$H NMR (d$_4$ MeOH) was consistent with the desired structure 105. LC/MS showed one peak with a M+1 molecular ion of m/z 374.4 by positive ESI.

Example 6

5-(1-(5-(aminomethyl)pyridin-2-yl)-3-pyridin-4-yl-1H-pyrazol-4-yl)-2,3-dihydroinden-1-one oxime 117

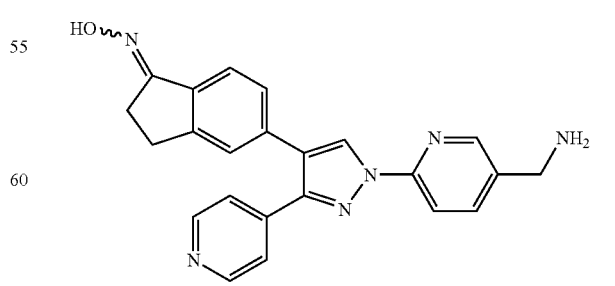

117

Step 1: Preparation of 6-(4-bromo-3-(pyridin-4-yl)-1H-pyrazol-1-yl)nicotinonitrile: To 4-(4-bromo-1H-pyrazol-3- yl)-pyridine (200 mg; Example 4, Step 1) in 5 mL DMF was added slowly 0.043 g of a 60% suspension of sodium hydride in mineral oil. After 20 minutes 0.124 g 6-chloronicotinonitrile was added. The mixture was heated at 80° C. overnight. The cooled reaction mixture was diluted with water and resulting solid was collected by vacuum filtration to yield 0.26 g (89% yield) product as a tan solid. $^1$H NMR (CDCl$_3$) was consistent with the desired structure. LC/MS showed one peak with a M+1 molecular ion of m/z 328.5 by positive ESI.

Step 2: Preparation of (E)-6-(4-(1-(benzyloxyimino)-2,3-dihydro-1H-inden-5-yl) 3-(pyridin-4-yl)-1H-pyrazol-1-yl)nicotinonitrile: To 6-(4-bromo-3-(pyridin-4-yl)-1H-pyrazol-1-yl)nicotinonitrile (0.26 g; Example 6, step 1) in 16 mL acetonitrile and 4 mL water was added (E)-1-(benzyloxyimino)-2,3-dihydro-1H-inden-5-ylboronic acid (0.34 g; Example 2, Step 4) and 0.33 g potassium carbonate. The reaction mixture was purged with nitrogen and 46 mg tetrakis(triphenyphosphine)palladium(0) catalyst was added. The reaction mixture was heated to 80° C. for 1.5 hours, filtered through celite, the filter cake was washed with acetonitrile. The filtrate was evaporated to yield crude product, which was purified by chromatography, eluting with a 10:1 mixture of dichloromethane-methanol to afford 0.15 g (36% yield) product as a pale yellow solid. $^1$H NMR (CDCl$_3$) was consistent with the desired structure. LC/MS showed one peak with a M+1 molecular ion of m/z 483.2 by positive ESI.

Step 3: Preparation of 5-(1-(5-(aminomethyl)pyridin-2-yl)-3-pyridin-4-yl-1H-pyrazol-4-yl)-2,3-dihydroinden-1-one oxime 117: To (E)-6-(4-(1-(benzyloxyimino)-2,3-dihydro-1H-inden-5-yl) 3-(pyridin-4-yl)-1H-pyrazol-1-yl)nicotinonitrile (0.15 g; Example 6, Step 2) in 10 mL methanol was added 205 µL 6M hydrochloric acid and 11 mg palladium hydroxide (20% by weight on carbon). A hydrogen-filled balloon was attached to the reaction vessel and the mixture was stirred at ambient temperature for 2 hours. The mixture was filtered through celite and the celite was washed with methanol. The filtrate was concentrated under vacuum and the residue was dissolved in 10 mL methanol, treated with 1.00 g of MP-carbonate resin (2.86 mmol/g loading) for 20 minutes, filtered and evaporated under vacuum. The crude product was purified by chromatography, eluting with a mixture of 50:10:1 dichloromethane-methanol-triethylamine to yield 0.088 g (71% yield) of a white solid.

$^1$H NMR (d$_6$ DMSO) was consistent with the desired structure 117. LC/MS showed one peak with a M+1 molecular ion of m/z 397.3 by positive ESI.

Example 7

5-(2-(pyridin-4-yl)pyrazolo [1.5-a]pyrimidin-3-yl)-2,3-dihydroinden-1-one oxime 124

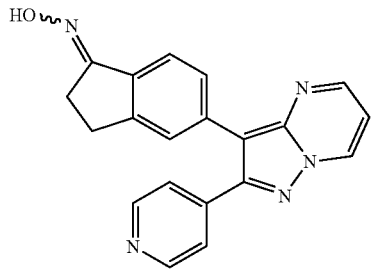

124

Step 1: Preparation of 3-oxo-3-(pyridin-4-yl)propanenitrile: To 20.00 g methyl isonicotinate in 290 mL dry toluene, was added a solution of 50 mL 4.37M sodium methoxide in methanol, followed by 19.2 mL acetonitrile. The resulting mixture was refluxed for 16 hours and concentrated to dryness. The solids were then taken up in a minimal amount of water and the pH adjusted to pH 5-6 with concentrated hydrochloric acid. The mixture was diluted with water and extracted with a mixture of 1:10 isopropyl alcohol-dichloromethane. The organic extracts dried over sodium sulfate, filtered, and evaporated to yield 3.9 g product as a dark foam. $^1$H NMR (d6 DMSO) was consistent with the desired structure. MS showed a M+1 molecular ion of m/z 145.2 by positive APCI (atmospheric pressure chemical ionization mass spectrometry).

Step 2: Preparation of 5-(pyridin-4-yl)-1-H-pyrazol-3-amine: To 3-oxo-3-(pyridin-4-yl)propanenitrile (3.40 g; Example 7, Step 1) suspended in 230 mL ethanol was added 2.92 mL hydrazine. The mixture refluxed for 3 hours and concentrated to dryness. The residue was purified by chromatography, eluting with a mixture of 10% methanol in dichloromethane to yield 0.80 g (21% yield) product as a light yellow solid. MS showed a M+1 molecular ion of m/z 161.3 by positive APCI.

Step 3: Preparation of 2-(pyridin-4-yl)pyrazolo[1.5-a]pyrimidine: To 5-(pyridin-4-yl)-1-H-pyrazol-3-amine (0.50 g; Example 7, Step 2) in 31 mL ethanol was added 0.182 g zinc chloride, 0.54 mL malonaldehyde, and 7.8 mL concentrated hydrochloric acid. The mixture was refluxed for 1 hour, cooled, and concentrated to dryness. The residue taken up in concentrated ammonium hydroxide, diluted with water, and extracted with a mixture of 10% methanol in ethyl acetate. The extracts dried over sodium sulfate and evaporated to afford 0.50 g (81% yield) product as a tan solid. $^1$H NMR (d$_6$ DMSO) was consistent with the desired structure. MS showed a M+1 molecular ion of m/z 197.4 by positive APCI.

Step 4: Preparation of 3-bromo-2-(pyridin-4-yl)pyrazolo[1.5-a]pyrimidine: To 2-(pyridin-4-yl)pyrazolo[1.5-a]pyrimidine (0.30 g) in 15 mL chloroform was added dropwise a solution of 86 µL bromine in 1 mL chloroform. After 1.5 hours. at ambient temperature, the mixture was diluted with dichloromethane, washed with 10% aqueous potassium carbonate, dried over sodium sulfate, filtered, and evaporated to afford 386 mg (92% yield) product as a tan solid. MS showed a M+1 molecular ion of m/z 277.4 by positive APCI.

Step 5: Preparation of 5-(2-(pyridin-4-yl)pyrazolo[1.5-a]pyrimidin-3-yl)-2,3-dihydroinden-1-one O-methyl oxime: To 3-bromo-2-(pyridin-4-yl)pyrazolo[1.5-a]pyrimidine (0.150 g; Example 7, step 4) and (E)-1-(methoxyimino)-2,3-dihydro-1H-inden-5-ylboronic acid (0.224 g; Example 1, Step 5) in 5.5 mL 1,2-dimethoxyethane, was added 0.167 mL triethylamine and 27 mg 1,1'-bis(diphenylphosphino)ferrocene palladium (II) chloride catalyst. The mixture was heated at 60° C. for 16 hours, diluted with ethyl acetate, and washed with 10% aqueous potassium carbonate, dried over sodium sulfate, filtered, and evaporated to yield 94 mg (49% yield) product as a yellow solid. $^1$H NMR (CDCl$_3$) was consistent with the desired structure. MS showed a M+1 molecular ion of m/z 356.2 by positive APCI.

Step 6: Preparation of 5-(2-(pyridin-4-yl)pyrazolo[1.5-a]pyrimidin-3-yl)-2,3-dihydroinden-1-one: To 5-(2-(pyridin-4-yl)pyrazolo[1.5-a]pyrimidin-3-yl)-2,3-dihydroinden-1-one O-methyl oxime (0.090 g; Example 7, Step 5) in 1.3 mL dioxane was added 1.3 mL 4M hydrochloric acid and the mixture was heated to 100° C. for 5 hours. The cooled reaction mixture was diluted with ethyl acetate, washed with 10% aqueous potassium carbonate, dried over sodium sulfate, filtered, and evaporated to yield 75 mg product as a yellow-brown-solid. This material was carried on without further purification.

Step 7: Preparation of 5-(2-(pyridin-4-yl)pyrazolo[1.5-a]pyrimidin-3-yl)-2,3-dihydroinden-1-one oxime 124: To 5-(2-(pyridin-4-yl)pyrazolo[1.5-a]pyrimidin-3-yl)-2,3-dihydroinden-1-one (0.050 g; Example 7, step 6) in 1.5 mL ethanol was added 16 mg hydroxylamine hydrochloride and 19 µL pyridine. The resulting mixture was heated at 80° C. for 3 hours. The cooled reaction mixture was diluted with ethyl acetate, washed with 10% aqueous potassium carbonate, dried over sodium sulfate, filtered, and evaporated to yield crude product. The crude material was purified by preparative thin-layer chromatography, eluting with a mixture of 10% methanol in dichloromethane to afford 10 mg product as a tan solid. $^1$H NMR ($d_6$ DMSO) was consistent with the desired compound 124. MS showed a M+1 molecular ion of m/z 342.2 by positive APCI.

Example 8

B-Raf $IC_{50}$ Assay Protocol

Activity of human recombinant B-Raf protein may be assessed in vitro by assay of the incorporation of radiolabelled phosphate to recombinant MAP kinase (MEK), a known physiologic substrate of B-Raf, according to US 2004/127496 and WO 03/022840. Catalytically active human recombinant B-Raf protein is obtained by purification from sf9 insect cells infected with a human B-Raf recombinant baculovirus expression vector. To ensure that all substrate phosphorylation resulted from B-Raf activity, a catalytically inactive form of MEK was utilized. This protein is purified from bacterial cells expression mutant inactive MEK as a fusion protein with glutathione-S-transferase (GST-kdMEK).

The activity/inhibition of V600E full-length B-Raf was estimated by measuring the incorporation of radiolabeled phosphate from [γ-$^{33}$P]ATP into FSBA-modified wild-type MEK. The 30-EL assay mixtures contained 25 mM Na Pipes, pH 7.2, 100 mM KCl, 10 mM MgCl$_2$, 5 mM β-glycerophosphate, 100 µM Na Vanadate, 4 µM ATP, 500 nCi [γ-$^{33}$P]ATP, 1 µM FSBA-MEK and 20 nM V600E full-length B-Raf. Incubations were carried out at 22° C. in a Costar 3365 plate (Corning). Prior to the assay, the B-Raf and FSBA-MEK were preincubated together in assay buffer at 1.5× (20 µL of 30 nM and 1.5 µM, respectively) for 15 minutes, and the assay was initiated by the addition of 10 µL of 12 µM ATP. Following the 60-minute incubation, the assay mixtures were quenched by the addition of 200 µL of 25% TCA, the plate was mixed on a rotary shaker for 10 minutes, and the product was captured on a Perkin-Elmer GF/B filter plate using a Tomtec Mach III Harvester. After sealing the bottom of the plate, 32 µL of Bio-Safe II (Research Products International) scintillation cocktail were added to each well and the plate was top-sealed and counted in a Topcount NXT (Packard).

Example 9

In Vitro B-Raf Assay

The activity of test compounds (Formulas Ia and Ib) as B-Raf inhibitors may be determined by the following in vitro, fluorescence anisotropy kinase binding assay, according to U.S. 2004/127496 and WO 03/022840 as follows.

The kinase enzyme, fluorescent ligand and a variable concentration of test compound are incubated together to reach thermodynamic equilibrium under conditions such that in the absence of test compound the fluorescent ligand is significantly (>50%) enzyme bound and in the presence of a sufficient concentration (>10×Ki) of a potent inhibitor the anisotropy of the unbound fluorescent ligand is measurably different from the bound value.

The concentration of kinase enzyme is preferably greater than or equal to 1×$K_f$. The concentration of fluorescent ligand required will depend on the instrumentation used, and the fluorescent and physicochemical properties. The concentration used must be lower than the concentration of kinase enzyme, and preferably less than half the kinase enzyme concentration. A typical protocol is:

1. All compounds dissolved in Buffer of comparison 50 mM HEPES, pharmaceutical 7.5, 1 mM CHAPS, 10 mM MgCl$_2$.
2. B-Raf Enzyme concentration: 1 nM
3. Fluorescent ligand concentration: 0.5 nM
4. Test compound concentration: 0.5 nM-100 µM
5. Components incubated in 10 µL final volume in LJL HE 384 type B black microtitre plate until equilibrium reached (about 3 to 30 hours)
6. Fluorescence anisotropy read by LJL Acquest.

$K_i$=dissociation constant for inhibitor binding; $K_f$=dissociation constant for fluorescent ligand binding. The fluorescent ligand may be a rhodamine- or fluorescein-type dye.

Alternative assay conditions of B-Raf catalytic activity utilize 3 µg of GST-kdMEK, 10 µM ATP and 2 µCi $^{33}$P-ATP, 50 mM MOPS, 0.1 mM EDTA, 0.1M sucrose, 10 mM MgCl$_2$ plus 0.1% dimethylsulphoxide (containing compound where appropriate) in a total reaction volume of 30 µL. Reactions are incubated at 25° C. for 90 minutes and reactions terminated by addition of EDTA to a final concentration of 50 µM. 10 µL of reaction is spotted to P30 phosphocellulose paper and air dried. Following four washes in ice cold 10% trichloroacetic acid, 0.5% phosphoric acid, papers are air dried prior to addition of liquid scintillant and radioactivity is measured in a scintillation counter.

The activity of compounds as Raf inhibitors may also be determined by the assays described in WO 99/10325; McDonald, O. B., et al. (1999) Anal. Biochem. 268:318-329, and AACR meeting New Orleans 1998 Poster 3793.

Example 10

Neuroprotection In Vitro Assay

The neuroprotective properties of B-Raf inhibitors may be determined by the following in vitro assay in Rat Hippocampal Slice Cultures, according to US 2004/127496; US 2004/082014; and WO 03/022840 as follows.

Organotypic cultures provide an intermediate between dissociated neuronal cell cultures and in-vivo models of oxygen and glucose deprivation (OGD). The majority of glial-neuronal interactions and neuronal circuitry are maintained in cultured hippocampal slices, so facilitating investigation of the patterns of death among differing cell types in a model that resembles the in vivo situation. These cultures allow the study of delayed cellular damage and death 24 hours, or more, post-insult and permit assessment of the consequences of long-term alterations in culture conditions. A number of laboratories have reported delayed neuronal damage in response to OGD in organotypic cultures of the hippocampus (Vornov et al., Stroke, (1994) 25:57465; Newell et al. (1995) Brain Res. 676:38-44). Several classes of compounds have been shown to protect in this model, including EAA antagonists (Strasser et al., Brain Res., (1995) 687:167-174), Na channel blockers (Tasker et al., J. Neurosci., (1992) 12:98-4308) and Ca channel blockers (Pringle et al. (1996) Stroke 7:2124-2130).

Method: Organotypic hippocampal slice cultures were prepared using the method of Stoppini et al (1995) J. Neurosci. Methods 37:173-182. Briefly, 400 micron sections prepared from hippocampi of 7-8 day postnatal Sprague Dawley rats are cultured on semiporous membranes for 9-12 days. OGD is then induced by incubation in serum and glucose-free medium in an anaerobic chamber for 45 minutes. Cultures are then returned to the air/$CO_2$ incubator for 23 hours before analysis. Propidium iodide (PI) is used as an indicator of cell death. PI is nontoxic to neurones and has been used in many studies to ascertain cell viability. In damaged neurons PI enters and binds to nucleic acids. Bound PI shows increased emission at 635 nm when excited at 540 nm. One PI fluorescence image and one white light image are taken and the proportion of cell death analyzed. The area of region CA1 is defined from the white light image and superimposed over the PI image. The PI signal is thresholded and area of PI damage expressed as a percentage of the CA1 area. Correlation between PI fluorescence and histologically confirmed cell death has been validated previously by Nissl-staining using cresyl fast violet (Newell et al. (1995) J. Neurosci. 15:7702-7711).

Example 11

Spectrophotometric ERK Inhibition Assay

The ERK inhibition properties of the compounds of the invention may also be determined by the following spectrophotometric coupled-enzyme assay (Fox et al. (1998) Protein Sci 7:2249). In this assay, a fixed concentration of activated ERK2 (10 nM) is incubated with various concentrations of the compound in DMSO (2.5%) for 10 minutes at 30° C. in 0.1 M HEPES buffer, pH 7.5, containing 10 mM $MgCl_2$, 2.5 mM phosphoenolpyruvate, 200 µM NADH, 150 µg/mL pyruvate kinase, 50 µg/mL lactate dehydrogenase, and 200 µM erktide peptide. The reaction is initiated by the addition of 65 µM ATP. The rate of decrease of absorbance at 340 nm is monitored, which indicates the extent of uninhibited enzyme present in the assay. The $IC_{50}$ is evaluated from the rate data as a function of inhibitor concentration.

Example 12

Cellular ERK 1/2 Phosphorylation Assay

The ERK inhibition properties of the compounds of the invention may be determined by the following in vitro cellular proliferation assay.

Inhibition of basal ERK1/2 phosphorylation was determined by incubating cells with compound for 1 hour and quantifying the fluorescent pERK signal on fixed cells and normalizing to total ERK signal.

Materials and Methods: Malme-3M cells were obtained from ATCC and grown in RPMI-1640 supplemented with 10% fetal bovine serum. Cells were plated in 96-well plates at 15,000 cells/well and allowed to attach for 1-2 hours. Diluted compounds were then added at a final concentration of 1% DMSO. After 1 hour, cells were washed with PBS and fixed in 3.7% formaldehyde in PBS for 15 minutes. This was followed by washing in PBS/0.2% Triton X-100 and permeabilizing in 100% MeOH for 15 minutes. Cells were blocked in Odyssey blocking buffer (LI-COR Biosciences) for at least 1 hour.

Antibodies to phosphorylated ERK (Cell Signaling #9106, monoclonal) and total ERK (Santa Cruz Biotechnology #sc-94, polyclonal) were added to the cells and incubated for at least 1 hour. After washing with PBS/0.2% TritonX-100, the cells were incubated with fluorescently-labeled secondary antibodies (goat anti-rabbit IgG-IRDye800, Rockland and goat anti-mouse IgG-Alexa Fluor 680, Molecular Probes) for an additional hour. Cells were then washed and analyzed for fluorescence at both wavelengths using the Odyssey Infrared Imaging System (LI-COR Biosciences). Phosphorylated ERK signal was normalized to total ERK signal.

Alternatively, the assay may comprise a complete media prepared by adding 10% fetal bovine serum and penicillin/streptomycin solution to RPMI 1640 medium (JRH Biosciences), according to US 2003/0139452. Colon cancer cells, e.g. HT-29 cell line, are added to each of 84 wells of a 96 well plate at a seeding density of 10,000 cells/well/150 µL. The cells are allowed to attach to the plate by incubating at 37° C. for 2 hours. A solution of test compound is prepared in complete media by serial dilution to obtain the following concentrations: 20 µM, 6.7 µM, 2.2 µM, 0.74 µM, 0.25 µM, and 0.08 µM. The test compound solution (50 µL) is added to each of 72 cell-containing wells. To the 12 remaining cell-containing wells, only complete media (200 µL) is added to form a control group in order to measure maximal proliferation. To the remaining 12 empty wells, complete media is added to form a vehicle control group in order to measure background. The plates are incubated at 37° C. for 3 days. A stock solution of $^3$H-thymidine (1 mCi/mL, New England Nuclear, Boston, Mass.) is diluted to 20 µCi/mL in RPMI medium then 20 µL of this solution is added to each well. The plates are further incubated at 37° C. for 8 hours then harvested and analyzed for 3H-thymidine uptake using a liquid scintillation counter.

Example 13

Cell Viability Assay

Viable cells after a 3-day incubation with compound were quantified using the MTS/PMS colorimetric assay from Promega.

Materials and Methods: Malme-3M cells were plated in 96 well plates at a density of 20,000 cells/well. The cells were allowed to attach for 1-2 hours. Diluted compounds were then added to the cells at a final concentration of 0.5% DMSO. After 3 days, the number of viable cells was determined using the MTS assay (Promega, CellTiter 96 Aqueous Non-radioactive Cell Proliferation Assay). Briefly, MTS reagents were added to the cells and incubated for 1 hour. Absorbance at 490 nm was then read using a microplate reader. Background from medium only wells was subtracted.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A compound selected from Formulas Ia and Ib:

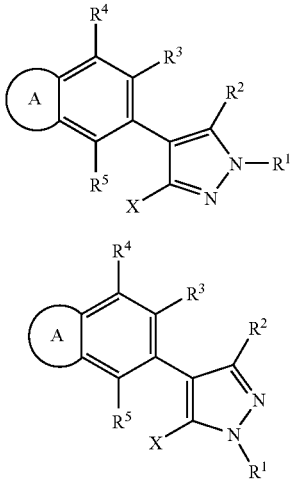

and stereoisomers, tautomers and pharmaceutically acceptable salts thereof, wherein:

the A-ring is a 5 or 6 membered carbocyclic ring, wherein said carbocyclic ring is optionally substituted with one or more groups independently selected from F, Cl, Br, I, —C(=Y)R$^{20}$, —C(=Y)OR$^{20}$, —C(=Y)NR$^{20}$R$^{21}$, NR$^{20}$R$^{21}$, —NR$^{20}$C(=Y)R$^{21}$, —NR$^{20}$C(=Y)OR$^{21}$, —NR$^{23}$C(=Y)NR$^{20}$R$^{21}$, =NOR$^{20}$, =NR$^{20}$, =N+(O)OR$^{20}$, =NNR$^{20}$R$^{21}$, =O, —OR$^{20}$, —OC(=Y)R$^{20}$, —OC(=Y)OR$^{20}$, —OC(=Y)NR$^{20}$R$^{21}$, —OS(O)$_2$(OR$^{20}$), —OP(=Y)(OR$^{20}$)(OR$^{21}$), —OP(OR$^{20}$)(OR$^{21}$), —P(=Y)(OR$^{20}$)(OR$^{21}$), —P(=Y)(OR)NR$^{20}$R$^{21}$, =S, —SR$^{20}$, —S(O)R$^{20}$, —S(O)$_2$R$^{20}$, —S(O)$_2$NR$^{20}$R$^{21}$, —S(O)(OR$^{20}$), —S(O)$_2$(OR$^{20}$), —SC(=Y)R$^{20}$, —SC(=Y)OR$^{20}$, —SC(=Y)NR$^{20}$R$^{21}$, C$_1$-C$_8$ alkyl, C$_2$-C$_8$ alkenyl, C$_2$-C$_8$ alkynyl, C$_6$-C$_{20}$ aryl, C$_3$-C$_{12}$ carbocyclyl, C$_2$-C$_{20}$ heterocyclyl, and a protecting group, and wherein said alkyl, alkenyl, alkynyl, aryl, carbocyclyl and heterocyclyl are optionally and independently substituted with one or more groups independently selected from F, Cl, Br, I, —C(=Y)R$^{20}$, —C(=Y)OR$^{20}$, —C(=Y)NR$^{20}$R$^{21}$, NR$^{20}$R$^{21}$, —NR$^{20}$C(=Y)R$^{21}$, —NR$^{20}$C(=Y)OR$^{21}$, —NR$^{23}$C(=Y)NR$^{20}$R$^{21}$, —OR$^{20}$, —OC(=Y)R$^{20}$, —OC(=Y)OR$^{20}$, —OC(=Y)NR$^{20}$R$^{21}$, —OS(O)$_2$(OR$^{20}$), —OP(=Y)(OR$^{20}$)(OR$^{21}$), —OP(OR$^{20}$)(OR$^{21}$), —P(=Y)(OR$^{20}$)(O$^{21}$), —P(=Y)(OR)NR$^{20}$R$^{21}$, —SR$^{20}$, —S(O)R$^{20}$, —S(O)$_2$R$^{20}$, —S(O)$_2$NR$^{20}$R$^{21}$, —S(O)(OR$^{20}$), —S(O)$_2$(OR$^{20}$), —SC(=Y)R$^{20}$, —SC(=Y)OR$^{20}$, —SC(=Y)NR$^{20}$R$^{21}$, C$_1$-C$_8$ alkyl, C$_2$-C$_8$ alkenyl, C$_2$-C$_8$ alkynyl, C$_6$-C$_{20}$ aryl, C$_3$-C$_{12}$ carbocyclyl, C$_2$-C$_{20}$ heterocyclyl;

X is a C$_2$-C$_{20}$ heterocyclyl, wherein said heterocycle, is optionally substituted with one or more groups independently selected from F, Cl, Br, I, —C(=Y)R$^{20}$, —C(=Y)OR$^{20}$, —C(=Y)NR$^{20}$R$^{21}$, —NR$^{20}$R$^{21}$, —NR$^{20}$C(=Y)R$^{21}$, —NR$^{20}$C(=Y)OR$^{21}$, —NR$^{23}$C(=Y)NR$^{20}$R$^{21}$, —OR$^{20}$, —OC(=Y)R$^{20}$, —OC(=Y)OR$^{20}$, —OC(=Y)NR$^{20}$R$^{21}$, —OS(O)$_2$(OR$^{20}$), —OP(=Y)(OR$^{20}$)(OR$^{21}$), —OP(OR$^{20}$)(OR$^{21}$), —P(=Y)(OR$^{20}$)(OR$^{21}$), —P(=Y)(OR$^{23}$)NR$^{20}$R$^{21}$, —SR$^{20}$, —S(O)R$^{20}$, —S(O)$_2$R$^{20}$, —S(O)$_2$NR$^{20}$R$^{21}$, —S(O) (OR$^{20}$), —S(O)$_2$(OR$^{20}$), —SC(=Y)R$^{20}$, —SC(=Y)OR$^{20}$, —SC(=Y)NR$^{20}$R$^{21}$, 5-7 membered ring lactam, 5-7 membered ring lactone, 5-7 membered ring sultam, C$_1$-C$_8$ alkyl, C$_2$-C$_8$ alkenyl, C$_2$-C$_8$ alkynyl, C$_3$-C$_{12}$ carbocyclyl, C$_6$-C$_{20}$ aryl, and C$_2$-C$_{20}$ heterocyclyl, wherein said alkyl, alkenyl, alkynyl, carbocyclyl, aryl, and heterocyclyl are optionally substituted with one or more groups independently selected from F, Cl, Br, I, OR$^{20}$, NR$^{20}$R$^{21}$—SR$^{20}$, —S(O)R$^{20}$, —S(O)$_2$R$^{20}$, alkyl, alkenyl, alkynyl, carbocyclyl, aryl, and heterocyclyl;

R$^1$ is selected from H, C$_1$-C$_8$ alkyl, C$_2$-C$_8$ alkenyl, C$_2$-C$_8$ alkynyl, (C$_1$-C$_8$ alkyl)NR$^{20}$R$^{21}$, a C$_2$-C$_{20}$ heterocyclyl, a C$_3$-C$_{12}$ carbocyclyl, and a C$_6$-C$_{20}$ aryl, wherein said alkyl, alkenyl, alkynyl, heterocycle, carbocyclyl and aryl are optionally substituted with one or more groups independently selected from F, Cl, Br, I, —C(=Y)R$^{20}$, —C(=Y)OR$^{20}$, —C(=Y)NR$^{20}$R$^{21}$, —NR$^{20}$R$^{21}$, OR$^{20}$, CN, C(=O)NR$^{20}$R$^{21}$, C(=O)OR$^{20}$, alkyl, (C$_1$-C$_8$ alkyl)NR$^{20}$R$^{21}$, and heterocyclyl;

R$^2$ is selected from H, —C(=Y)R$^{20}$, —C(=Y)OR$^{20}$, —C(=Y)NR$^{20}$R$^{21}$, C$_1$-C$_8$ alkyl, C$_2$-C$_8$ alkenyl, and C$_2$-C$_8$ alkynyl, wherein said alkyl, alkenyl, and alkynyl, are optionally substituted with one or more groups independently selected from F, Cl, Br, I, OR$^{20}$, NR$^{20}$R$^{21}$—SR$^{20}$, —S(O)R$^{20}$, —S(O)$_2$R$^{20}$, alkyl, alkenyl, alkynyl, carbocyclyl, aryl, and heterocyclyl, or R$^1$ and R$^2$ of Formula Ia together with the atoms to which they are attached optionally form an aromatic 5 or 6 membered fused heterocycle ring having at least two heteroatoms independently selected from O, N and S, wherein said heterocycle ring is optionally substituted with one or more groups independently selected from F, Cl, Br, I, —C(=Y)R$^{20}$, —C(=Y)OR$^{20}$, —C(=Y)NR$^{20}$R$^{21}$, NR$^{20}$R$^{21}$, —NR$^{20}$C(=Y)R$^{21}$, —NR$^{20}$C(=Y)OR$^{21}$, —NR$^{23}$C(=Y)NR$^{20}$R$^{21}$, —OR$^{20}$, —OC(=Y)R$^{20}$, —OC(=Y)OR$^{20}$, —OC(=Y)NR$^{20}$R$^{21}$, —OS(O)$_2$(OR$^{20}$), —OP(=Y)(OR$^{20}$)(OR$^{21}$), —OP(OR$^{20}$)(OR$^{21}$), —P(=Y)(OR$^{20}$)(OR$^{21}$), —P(=Y)(OR$^{23}$)NR$^{20}$R$^{21}$, —SR$^{20}$, —S(O)R$^{20}$, —S(O)$_2$R$^{20}$, —S(O)$_2$NR$^{20}$R$^{21}$, —S(O)(OR$^{20}$), —S(O)$_2$(OR$^{20}$), —SC(=Y)R$^{20}$, —SC(=Y)OR$^{20}$, —SC(=Y)NR$^{20}$R$^{21}$, 5-7 membered ring lactam, 5-7 membered ring lactone, 5-7 membered ring sultam, C$_1$-C$_8$ alkyl, C$_2$-C$_8$ alkenyl, C$_2$-C$_8$ alkynyl, C$_3$-C$_{12}$ carbocyclyl, C$_6$-C$_{20}$ aryl, and C$_2$-C$_{20}$ heterocyclyl, wherein said alkyl, alkenyl, alkynyl, carbocyclyl, aryl, and heterocyclyl are optionally substituted with one or more groups independently selected from F, Cl, Br, I, OR$^{20}$, NR$^{20}$R$^{21}$—SR$^{20}$, —S(O)R$^{20}$, —S(O)$_2$R$^{20}$, alkyl, alkenyl, alkynyl, carbocyclyl, aryl, and heterocyclyl;

R$^3$, R$^4$, and R$^5$ are independently selected from H, F, Cl, Br, I, —C(=Y)R$^{20}$, —C(=Y)OR$^{20}$, —C(=Y)NR$^{20}$R$^{21}$, —NR$^{20}$R$^{21}$, —NR$^{20}$C(=Y)R$^{21}$, —NR$^{20}$C(=Y)OR$^{21}$, —NR$^{23}$C(=Y)NR$^{20}$R$^{21}$, —OR$^{20}$, —OC(=Y)R$^{20}$, —OC(=Y)OR$^{20}$, —OC(=Y)NR$^{20}$R$^{21}$, —OS(O)$_2$(OR$^{20}$), —OP(=Y)(OR$^{20}$)(OR$^{21}$), —OP(OR$^{20}$)(OR$^{21}$), —P(=Y)(OR$^{20}$)(OR$^{21}$), —P(=Y)(OR$^{23}$)NR$^{20}$R$^{21}$, —SR$^{20}$, —S(O)R$^{20}$, —S(O)$_2$R$^{20}$, —S(O)$_2$NR$^{20}$R$^{21}$, —S(O)(OR$^{20}$), —S(O)$_2$(OR$^{20}$), —SC(=Y)R$^{20}$, —SC(=Y)OR$^{20}$, —SC(=Y)NR$^{20}$R$^{21}$, 5-7 membered ring lactam, 5-7 membered ring lactone, 5-7 membered ring sultam, C$_1$-C$_8$ alkyl, C$_2$-C$_8$ alkenyl, C$_2$-C$_8$ alkynyl, C$_3$-C$_{12}$ carbocyclyl, C$_6$-C$_{20}$ aryl, and C$_2$-C$_{20}$ heterocyclyl, wherein said alkyl, alkenyl, alkynyl, carbocyclyl, aryl, and heterocyclyl are optionally substituted with one or more groups independently selected from F, Cl, Br, I, OR$^{20}$, NR$^{20}$R$^{21}$—SR$^{20}$, —S(O)R$^{20}$, —S(O)$_2$R$^{20}$, alkyl, alkenyl, alkynyl, carbocyclyl, aryl, and heterocyclyl;

R$^{20}$ and R$^{21}$ are independently selected from H, C$_1$-C$_8$ alkyl, C$_2$-C$_8$ alkenyl, C$_2$-C$_8$ alkynyl, C$_6$-C$_{20}$ aryl, C$_2$-C$_{20}$ heterocyclyl, and a protecting group, wherein said alkyl, alkenyl, alkynyl, aryl, and heterocyclyl are optionally and independently substituted with one or more groups independently selected from F, Cl, Br, I, —C(=Y)R$^a$, —C(=Y)OR$^a$, —C(=Y)NR$^a$R$^b$, —OR$^a$, —OC(=Y) R$^a$, —OC(=Y)OR$^a$, —OC(=Y)NR$^a$R$^b$, —OS(O)$_2$ (OR$^a$), —OP(=Y)(OR$^a$)(OR$^b$), —OP(OR$^a$)(OR$^b$), —P(=Y)(OR$^a$)(OR$^b$), —P(=Y)(OR)NR$^a$R$^b$, —SR$^a$, —S(O)R$^a$, —S(O)$_2$R$^a$, —S(O)$_2$NR$^a$R$^b$, —S(O)(OR$^a$), —S(O)$_2$(OR$^a$), —SC(=Y)R$^a$, —SC(=Y)OR$^a$, and —SC(=Y)NR$^a$R$^b$, or R$^{20}$ and R$^{21}$ together with the atoms to which they are attached form a heterocyclic ring, wherein said heterocyclic ring is optionally substituted with one or more groups independently selected from F, Cl, Br, I, alkyl, alkenyl and alkynyl;

R$^{23}$ is H, C$_1$-C$_8$ alkyl, C$_2$-C$_8$ alkenyl, C$_2$-C$_8$ alkynyl, C$_6$-C$_{20}$ aryl, C$_2$-C$_{20}$ heterocyclyl, or a protecting group;

R$^a$ and R$^b$ are independently H, C$_1$-C$_8$ alkyl, C$_2$-C$_8$ alkenyl, C$_2$-C$_8$ alkynyl, C$_6$-C$_{20}$ aryl, or C$_2$-C$_{20}$ heterocyclyl;

Y is independently O, S, NR$^{20}$, $^+$N(O)R$^{20}$, N(OR$^{20}$), $^+$N(O)(OR$^{20}$), or N—NR$^{20}$R$^{21}$; and protecting group is selected from trialkylsilyl, dialkylphenylsilyl, benzoate, benzyl, benzyloxymethyl, methyl, methoxymethyl, triarylmethyl, phthalimido, t-butoxycarbonyl (BOC), benzyloxycarbonyl (CBz), 9-fluorenylmethylenoxycarbonyl (Fmoc), and tetrahydropyranyl.

2. The compound of claim 1 wherein R$^1$ is H.

3. The compound of claim 1 wherein R$^1$ is an optionally substituted C$_1$-C$_8$ alkyl.

4. The compound of claim 3, wherein R$^1$ is methyl.

5. The compound of claim 3, wherein R$^1$ is alkyl substituted with NR$^{20}$R$^{21}$.

6. The compound of claim 5, wherein R$^1$ is CH$_2$CH$_2$NH$_2$, CH$_2$CH$_2$CH$_2$NH$_2$, or CH$_2$CH$_2$CH$_2$NH$_2$.

7. The compound of claim 5, wherein R$^1$ is CH$_2$CH$_2$CH$_2$NHCH$_2$C(=O)OCH$_3$.

8. The compound of claim 5, wherein R$^1$ is CH$_2$CH$_2$NHCH$^2$CH$_2$OH.

9. The compound of claim 3, wherein R$^1$ is alkyl substituted with a heterocyclyl.

10. The compound of claim 9, wherein R$^1$ is selected from the structures:

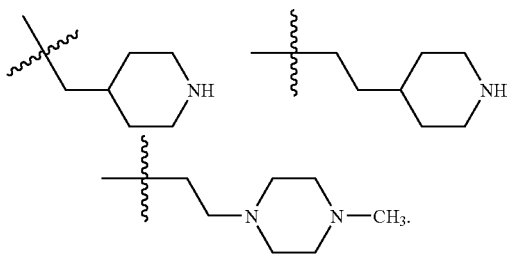

11. The compound of claim 3, wherein R$^1$ is alkyl substituted with OR$^{20}$.

12. The compound of claim 11, wherein R$^1$ is CH$_2$CH$_2$OH or CH$_2$CH(OH)CH$_2$OH.

13. The compound of claim 3, wherein R$^1$ is alkyl substituted with C(=O)OR$^{20}$.

14. The compound of claim 13, wherein R$^1$ is CH$_2$C(=O) OH.

15. The compound of claim 1, wherein R$^1$ is an optionally substituted heterocyclyl.

16. The compound of claim 15, wherein R$^1$ is selected from the structures:

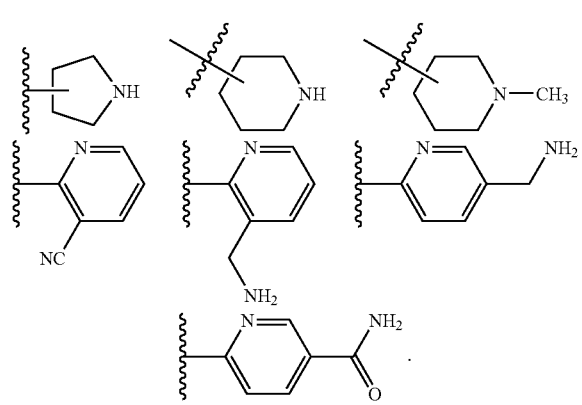

17. The compound of claim 15, wherein R$^1$ is selected from the structures:

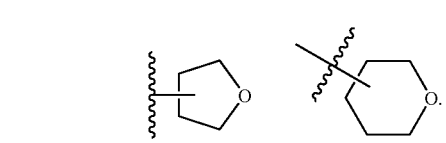

18. The compound of claim 1, wherein R$^1$ is an optionally substituted carbocyclyl.

19. The compound of claim 18, wherein R$^1$ is selected from the structures:

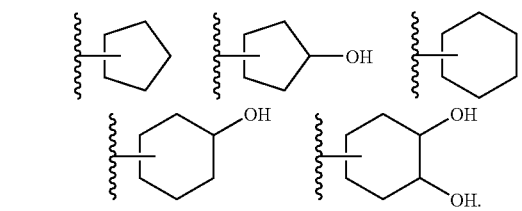

20. The compound of claim 1, wherein X is an optionally substituted C$_2$-C$_{20}$ heterocyclyl.

21. The compound of claim 20 wherein X is an optionally substituted 2-pyridyl, 3-pyridyl, 4-pyridyl, 2-imidazolyl, 4-imidazolyl, 3-pyrazolyl, 4-pyrazolyl, 2-thiazolyl, 4-thiazolyl, 5-thiazolyl, 3-pyridazinyl, 4-pyridazinyl, 5-pyridazinyl, 2-pyrimidinyl, 5-pyrimidinyl, 6-pyrimidinyl, 2-pyrazinyl, 2-oxazolyl, 4-oxazolyl, or 5-oxazolyl.

22. The compound of claim 21 wherein X is optionally substituted 4-pyridyl.

23. The compound of claim 1 wherein the A-ring is an optionally substituted ring selected from cyclopentyl, cyclopentenyl, cyclohexyl, and cyclohexenyl.

24. The compound of claim 1 wherein R$^1$ and R$^2$ of Formula Ia together with the atoms to which they are attached form a 5 or 6 membered fused heterocycle ring having at least two heteroatoms selected from O, N and S.

25. The compound of claim 24 wherein $R^1$ and $R^2$ together with the atoms to which they are attached form a fused pyrimidine ring.

26. The compound of claim 24 wherein the A-ring is an optionally substituted ring selected from cyclopentyl, cyclopentenyl, cyclohexyl, and cyclohexenyl.

27. The compound of claim 1 selected from Formulas IIa-h and IIIa-f:

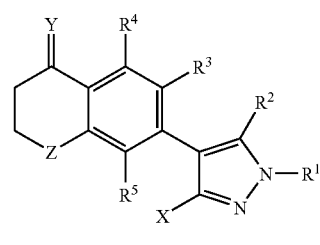
IIa

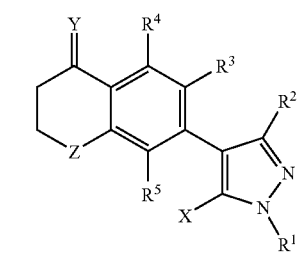
IIb

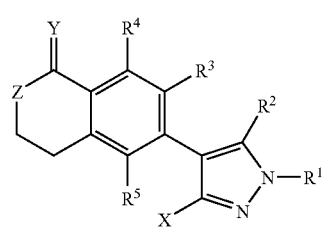
IIc

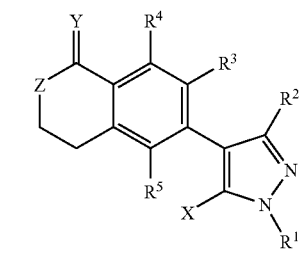
IId

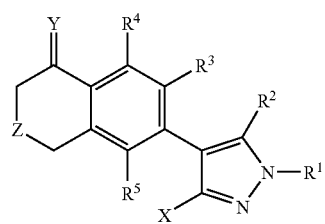
IIe

-continued

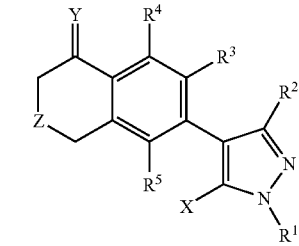
IIf

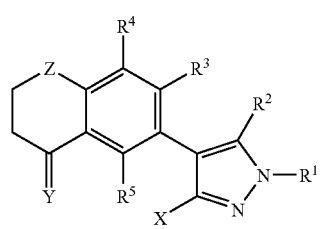
IIg

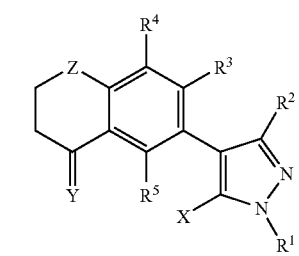
IIh

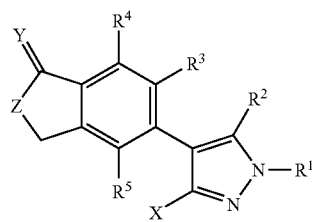
IIIa

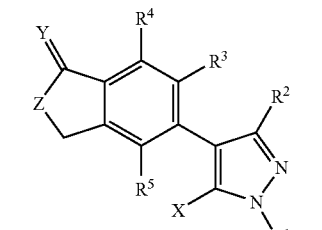
IIIb

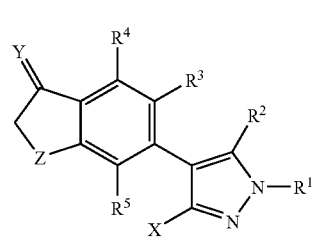
IIIc

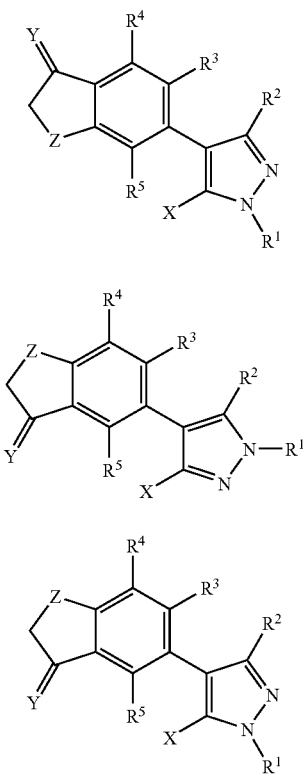

IIId

IIIe

IIIf wherein Z is selected from $CR^{20}R^{21}$, and C(=Y).

28. The compound of claim 27 wherein Z is $CH_2$.

29. The compound of claim 27 wherein Y is O.

30. The compound of claim 27 wherein Y is N—$OR^{20}$.

31. The compound of claim 30 wherein Y is N—OH.

32. The compound of claim 27 wherein Z is $CH_2$, and Y is N—$OR^{20}$.

33. The compound of claim 27 selected from Formulas IIa, IIc, IIe, IIg, IIIa, IIIc, and IIIe wherein $R^1$ and $R^2$ together with the atoms to which they are attached form a 5 or 6 membered fused heterocycle ring having at least two heteroatoms selected from O, N and S.

34. The compound of claim 33 wherein $R^1$ and $R^2$ together with the atoms to which they are attached form a fused pyrimidine ring.

35. The compound of claim 27 selected from Formulas VIa, VIb, VIIa and VIIb:

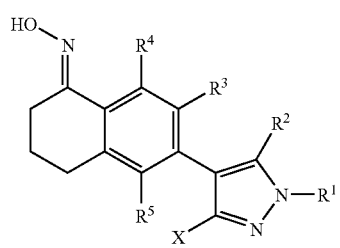

VIa

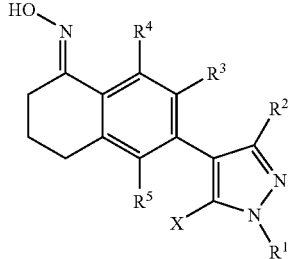

VIb

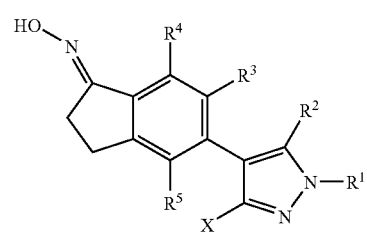

VIIa

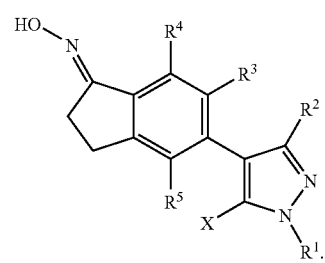

VIIb

36. The compound of claim 35 wherein $R^1$ and $R^2$ of Formulas VIa and VIIa together with the atoms to which they are attached form a 5 or 6 membered fused heterocycle ring having at least two heteroatoms selected from O, N and S.

37. The compound of claim 36 wherein $R^1$ and $R^2$ together with the atoms to which they are attached form a fused pyrimidine ring.

38. The compound of claim 35 selected from Formulas VIIIa, VIIIb, IXa and IXb:

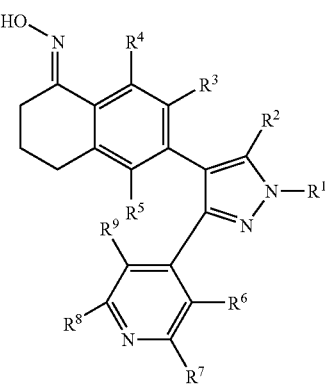

VIIIa

-continued

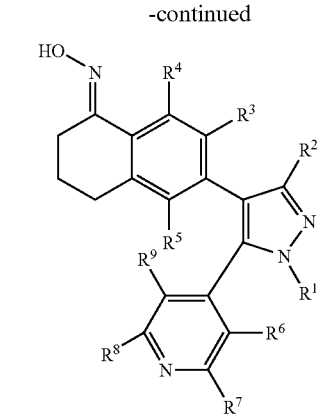

VIIIb

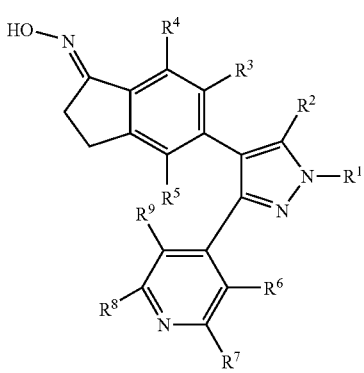

IXa

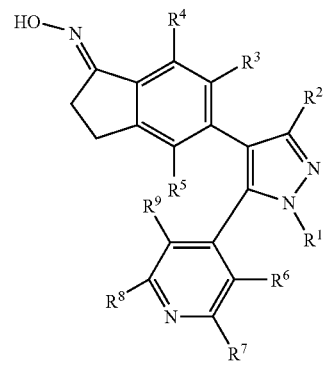

IXb wherein $R^6$, $R^7$, $R^8$, and $R^9$ are independently selected from H, F, Cl, Br, I, —C(=Y)$R^{20}$, —C(=Y)O$R^{20}$, —C(=Y)N$R^{20}R^{21}$, —N$R^{20}R^{21}$, —N$R^{20}$C(=Y)$R^{21}$, —N$R^{20}$C(=Y)O$R^{21}$, —N$R^{23}$C(=Y)N$R^{20}R^{21}$, —O$R^{20}$, —OC(=Y)$R^{20}$, —OC(=Y)O$R^{20}$, —OC(=Y)N$R^{20}R^{21}$, —OS(O)$_2$(O$R^{20}$), —OP(=Y)(O$R^{20}$)(O$R^{21}$), —OP(O$R^{20}$)(O$R^{21}$), —P(=Y)(O$R^{20}$)(O$R^{21}$), —P(=Y)(O$R^{23}$)N$R^{20}R^{21}$, —S$R^{20}$, —S(O)$R^{20}$, —S(O)$_2$ $R^{20}$, —S(O)$_2$N$R^{20}R^{21}$, —S(O)(O$R^{20}$), —S(O)$_d$ (O$R^{20}$), —SC(=Y)$R^{20}$, —SC(=Y)O$R^{20}$, —SC(=Y)N$R^{20}R^{21}$, 5-7 membered ring lactam, 5-7 membered ring lactone, 5-7 membered ring sultam, $C_1$-$C_8$ alkyl, $C_2$-$C_8$ alkenyl, $C_2$-$C_8$ alkynyl, $C_3$-$C_{12}$ carbocyclyl, $C_6$-$C_{20}$ aryl, and $C_2$-$C_{20}$ heterocyclyl, wherein said alkyl, alkenyl, alkynyl, carbocyclyl, aryl, and heterocyclyl are optionally substituted with one or more groups independently selected from F, Cl, Br, I, O$R^{20}$, N$R^{20}R^{21}$—S$R^{20}$, —S(O)$R^{20}$, —S(O)$_2R^{20}$, alkyl, alkenyl, alkynyl, carbocyclyl, aryl, and heterocyclyl.

39. The compound of claim 38 wherein $R^2$, $R^3$, $R^4$, and $R^5$ are H.

40. The compound of claim 38 wherein $R^6$, $R^7$, $R^8$, and $R^9$ are H.

41. The compound of claim 38 wherein $R^1$ is H or an optionally substituted $C_1$-$C_8$alkyl.

42. The compound of claim 38 wherein $R^1$ and $R^2$ of Formulas VIIIa and IXa together with the atoms to which they are attached form a 5 or 6 membered fused heterocycle ring having at least two heteroatoms selected from O, N and S.

43. The compound of claim 1 selected from Formulas XIIa-d and XIIIa-j:

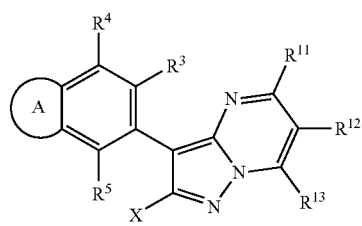

XIIa

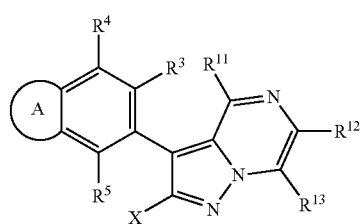

XIIb

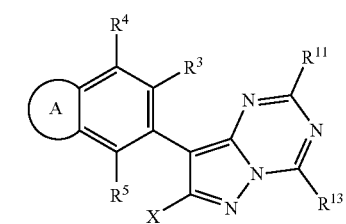

XIIc

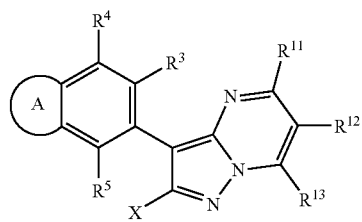

XIId

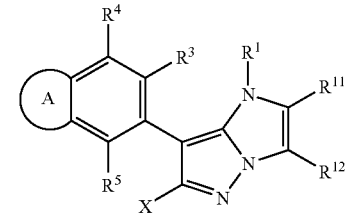

XIIIa

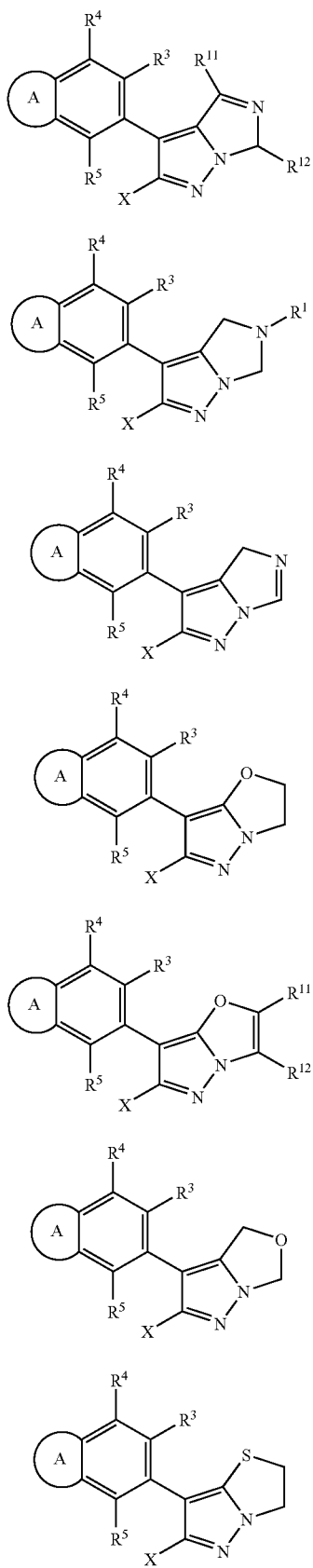

wherein $R^{11}$, $R^{12}$, and $R^{13}$ are independently selected from H, F, Cl, Br, I, —$OR^{20}$, —$C(=Y)R^{20}$, —$C(=Y)OR^{20}$, —$C(=Y)NR^{20}R^{21}$, —$NR^{20}R^{21}$, —$NR^{20}C(=Y)R^{21}$, —$NR^{20}C(=Y)OR^{21}$, —$NR^{23}C(=Y)NR^{20}R^{21}$, —$OC(=Y)R^{20}$, —$OC(=Y)OR^{20}$, —$OC(=Y)NR^{20}R^{21}$, —$OS(O)_2(OR^{20})$, —$OP(=Y)(OR^{20})(OR^{21})$, —$OP(OR^{20})(OR^{21})$, —$P(=Y)(OR^{20})(OR^{21})$, —$P(=Y)(OR^{23})NR^{20}R^{21}$, —$SR^{20}$, —$S(O)R^{20}$, —$S(O)_2R^{20}$, —$S(O)_2NR^{20}R^{21}$, —$S(O)(OR^{20})$, —$S(O)_2(OR^{20})$, —$SC(=Y)R^{20}$, —$SC(=Y)OR^{20}$, —$SC(=Y)NR^{20}R^{21}$, 5-7 membered ring lactam, 5-7 membered ring lactone, 5-7 membered ring sultam, $C_1$-$C_8$ alkyl, $C_2$-$C_8$ alkenyl, $C_2$-$C_8$ alkynyl, $C_3$-$C_{12}$ carbocyclyl, $C_6$-$C_{20}$ aryl, and $C_2$-$C_{20}$ heterocycle, wherein said alkyl, alkenyl, alkynyl, carbocyclyl, aryl, and heterocycle are optionally substituted with one or more groups independently selected from F, Cl, Br, I, $OR^{20}$, $NR^{20}R^{21}$, —$SR^{20}$, —$S(O)R^{20}$, —$S(O)_2R^{20}$, alkyl, alkenyl, alkynyl, carbocyclyl, aryl, and heterocycle.

44. The compound of claim 43 wherein X is selected from 2-pyridyl, 3-pyridyl, 4-pyridyl, 2-imidazolyl, 4-imidazolyl, 3-pyrazolyl, 4-pyrazolyl, 2-thiazolyl, 4-thiazolyl, and 5-thiazolyl, and substituted forms thereof.

45. The compound of claim 43 wherein X is an optionally substituted 4-pyridyl.

46. The compound of claim 43 wherein the A-ring is an optionally substituted ring selected from cyclopentyl, cyclopentenyl, cyclohexyl, and cyclohexenyl.

47. The compound of claim 1 selected from:
5-(1-(2-aminoethyl)-3-pyridin-4-yl-1H-pyrazol-4-yl)-2,3-dihydroinden-1-one oxime;
5-(1-(3-aminopropyl)-3-pyridin-4-yl-1H-pyrazol-4-yl)-2,3-dihydroinden-1-one oxime;
5-(1-(4-aminobutyl)-3-pyridin-4-yl-1H-pyrazol-4-yl)-2,3-dihydroinden-1-one oxime;
5-(1-(pyrrolidin-3-yl)-3-pyridin-4-yl-1H-pyrazol-4-yl)-2,3-dihydroinden-1-one oxime;
5-(1-(piperidin-4-yl)-3-pyridin-4-yl-1H-pyrazol-4-yl)-2,3-dihydroinden-1-one oxime;
5-(1-(4-methylpiperidinyl)-3-pyridin-4-yl-1H-pyrazol-4-yl)-2,3-dihydroinden-1-one oxime;
5-(1-(3R-tetrahydrofuranyl)-3-pyridin-4-yl-1H-pyrazol-4-yl)-2,3-dihydroinden-1-one oxime;
5-(1-(3S-tetrahydrofuranyl)-3-pyridin-4-yl-1H-pyrazol-4-yl)-2,3-dihydroinden-1-one oxime;

5-(1-(4-tetrahydropyranyl)-3-pyridin-4-yl-1H-pyrazol-4-yl)-2,3-dihydroinden-1-one oxime;
5-(1-(2-hydroxyethyl)-3-pyridin-4-yl-1H-pyrazol-4-yl)-2,3-dihydroinden-1-one oxime;
5-(1-(3S-(1R-hydroxy)cyclohexyl)-3-pyridin-4-yl-1H-pyrazol-4-yl)-2,3-dihydroinden-1-one oxime;
5-(1-(2,3dihydroxypropyl)-3-pyridin-4-yl-1H-pyrazol-4-yl)-2,3-dihydroinden-1-one oxime;
5-(1-methyl-3-pyridin-4-yl-1H-pyrazol-4-yl)-2,3-dihydroinden -1-one oxime;
5-(1-(3-cyano-pyridin-2-yl)-3-pyridin-4-yl-1H-pyrazol-4-yl)-2,3-dihydroinden-1-one oxime;
5-(1-(3S-(1S-hydroxy)cyclohexyl)-3-pyridin-4-yl-1H-pyrazol-4-yl)-2,3-dihydroinden-1-one oxime;
5-(1-(3-aminomethyl-pyridin-2-yl)-3-pyridin-4-yl-1H-pyrazol-4-yl)-2,3-dihydroinden-1-one oxime;
5-(1-(5-(aminomethyl)pyridin-2-yl)-3-pyridin-4-yl-1H-pyrazol-4-yl)-2,3-dihydroinden-1-one oxime;
5-(1-(3S-(1S, 2R-dihydroxy)cyclohexyl)-3-pyridin-4-yl-1H-pyrazol-4-yl)-2,3-dihydroinden-1-one oxime;
5-(1-(3-methoxyacetamidopropyl)-3-pyridin-4-yl-1H-pyrazol-4-yl)-2,3-dihydroinden-1-one oxime;
5-(1-(4-aminomethylphenyl)-3-pyridin-4-yl-1H-pyrazol-4-yl)-2,3-dihydroinden-1-one oxime;
5-(1-(5-(acetamido)pyridin-2-yl)-3-pyridin-4-yl-1H-pyrazol-4-yl)-2,3-dihydroinden-1-one oxime;
5-(1-Methyl-5-pyridin-4-yl-1H-pyrazol-4-yl)-2,3-dihydroinden-1-one oxime;
5-(1-(2-hydroxyethyl)-5-pyridin-4-yl-1H-pyrazol-4-yl)-2,3-dihydroinden-1-one oxime;
5-(2-(pyridin-4-yl)pyrazolo[1.5-a]pyrimidin-3-yl)-2,3-dihydroinden-1-one oxime;
5-(1-(2S-(1S-hydroxy)cyclopentyl)-3-pyridin-4-yl-1H-pyrazol-4-yl)-2,3-dihydroinden-1-one oxime;
5-(3-pyridin-4-yl-1H-pyrazol-4-yl)-2,3-dihydroinden-1-one oxime;
5-(1-cyclopentyl-3-pyridin-4-yl-1H-pyrazol-4-yl)-2,3-dihydroinden-1-one oxime;
5-(1-(2-(4-methylpiperazinyl)ethyl)-3-pyridin-4-yl-1H-pyrazol-4-yl)-2,3-dihydroinden-1-one oxime;
5-(1-methyl-3-pyridin-4-yl-1H-pyrazol-4-yl)-2,3-dihydroinden -1-one;
5-(1-(2-(2-hydroxyethyl)aminoethyl)-3-pyridin-4-yl-1H-pyrazol-4-yl)-2,3-dihydroinden-1-one oxime;
5-(1-(2-(4-methylpiperazinyl)ethyl)-3-pyridin-4-yl-1H-pyrazol-4-yl)-2,3-dihydro-1H-inden-1-amine;
5-(2-hydroxyethyl-5-pyridin-4-yl-1H-pyrazol-4-yl)-2,3-dihydro-1H-inden-1-amine;
5-(1-(2S-(1S-hydroxy)cyclopentyl)-3-pyridin4-yl-1H-pyrazol-4-yl)-2,3-dihydro-1H-inden-1-amine;
5-(1-(2-(N-piperidyl)ethyl)-3-pyridin-4-yl-1H-pyrazol-4-yl)-2,3-dihydroinden-1-one oxime;
5-(1-(2-hydroxyethyl)-3-pyridin-4-yl-1H-pyrazol-4-yl)-2,3-dihydroinden-1-one;
5-(1-(4-(N-methylpiperidyl))-3-pyridin-4-yl-1H-pyrazol-4-yl)-2,3-dihydroinden-1-one oxime;
5-(3-pyridin-4-yl-1H-pyrazol-4-yl)-2,3-dihydroinden-1-one;
5-(1-acetic acid-3-pyridin-4-yl-1H-pyrazol-4-yl)-2,3-dihydroinden-1-one oxime; and
5-(1-(2-hydroxyethyl)-3-pyridin-4-yl-1H-pyrazol-4-yl)-2,3-dihydro-1H-inden-1-amine.

48. A pharmaceutical composition comprised of a compound of claim 1 and a pharmaceutically acceptable carrier.

49. A composition comprising the compound of claim 1 in an amount to detectably inhibit Raf kinase activity and a pharmaceutically acceptable carrier, adjuvant, or vehicle.

\* \* \* \* \*

UNITED STATES PATENT AND TRADEMARK OFFICE
CERTIFICATE OF CORRECTION

PATENT NO. : 7,491,829 B2
APPLICATION NO. : 11/345828
DATED : February 17, 2009
INVENTOR(S) : Ellen Laird et al.

It is certified that error appears in the above-identified patent and that said Letters Patent is hereby corrected as shown below:

On the Title page, Item 73, capitalize the letter "p" in the word "Biopharma".

On the Title page, Item (56) "Bellec et al." reference, line 30, delete "*Can.J.*" and replace with --*Can. J.*--.

Claim 1, column 96, line 34, insert a dash before the second "$NR^{20}R^{21}$" so that it appears as follows:

$NR^{20}R^{21}$, -$NR^{20}R^{21}$,

Claim 8, column 97, line 45, delete "$CH_2CH_2NHCH^2CH_2OH$." and replace with --$CH_2CH_2NHCH_2CH_2OH$.--.

Claim 38, column 103, line 49, delete "II" and replace with --H--; line 56, delete the space between "-$S(O)_2$" and "$R^{20}$" so that the formula appears as follows:

-$S(O)_2R^{20}$

Claim 38, column 103, line 57, delete "-$S(O)_d(OR^{20})$," and replace with -- -$S(O)_2(OR^{20})$,--.

Claim 41, column 104, line 7, delete "$C_1$-$C_8$alkyl." and replace with --$C_1$-$C_8$ alkyl.--.

Claim 47, column 107, line 27, italicize "H" so that the line appears as follows:

5-(1-Methyl-5-pyridin-4-yl-1*H*-pyrazol-4-yl)-2,3-dihy-

Signed and Sealed this

Thirtieth Day of November, 2010

David J. Kappos
*Director of the United States Patent and Trademark Office*

Claim 47, column 108, line 15, insert a dash between "pyridine" and "4" so that the line appears as follows:

5-(1-(2S-(1S-hydroxy)cyclopentyl)-3-pyridin-4-yl-1H-